(12) United States Patent
Brown et al.

(10) Patent No.: US 10,208,142 B2
(45) Date of Patent: *Feb. 19, 2019

(54) POLYMERS AND DNA COPOLYMER COATINGS

(71) Applicant: Illumina Cambridge Limited, Nr Saffron Walden, Essex (GB)

(72) Inventors: Andrew A. Brown, Nr Saffron Waldon (GB); Wayne N. George, Nr Saffron Walden (GB); Alexandre Richez, Nr Saffron Walden (GB); Anne-Cecile Dingwall, Nr Saffron Walden (GB); Xavier von Hatten, Nr Saffron Walden (GB)

(73) Assignee: Illumnia Cambridge Limited, Nr Saffron Walden, Essex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/809,656

(22) Filed: Nov. 10, 2017

(65) Prior Publication Data

US 2018/0155469 A1    Jun. 7, 2018

Related U.S. Application Data

(63) Continuation of application No. 14/927,252, filed on Oct. 29, 2015, now Pat. No. 9,815,916.

(60) Provisional application No. 62/073,764, filed on Oct. 31, 2014.

(51) Int. Cl.
| | |
|---|---|
| C08F 20/60 | (2006.01) |
| C12Q 1/6874 | (2018.01) |
| C08F 220/56 | (2006.01) |
| C08F 8/32 | (2006.01) |
| C08F 293/00 | (2006.01) |
| C40B 50/18 | (2006.01) |

(52) U.S. Cl.
CPC ............... *C08F 20/60* (2013.01); *C08F 8/32* (2013.01); *C08F 220/56* (2013.01); *C08F 293/005* (2013.01); *C12Q 1/6874* (2013.01); *B01J 2219/00637* (2013.01); *B01J 2219/00722* (2013.01); *C08F 2438/03* (2013.01); *C40B 50/18* (2013.01)

(58) Field of Classification Search
CPC ...... C08F 8/32; C08F 293/005; C08F 220/56; C08F 2438/03; C12Q 1/6874; C40B 50/18; B01J 2219/00637; B01J 2219/00722
See application file for complete search history.

(56) References Cited

U.S. PATENT DOCUMENTS

| | | | |
|---|---|---|---|
| 5,130,238 A | 7/1992 | Malek et al. | |
| 5,429,807 A | 7/1995 | Matson et al. | |
| 5,436,327 A | 7/1995 | Southern et al. | |
| 5,455,166 A | 10/1995 | Walker | |
| 5,561,071 A | 10/1996 | Hollenberg et al. | |
| 5,583,211 A | 12/1996 | Coassin et al. | |
| 5,599,675 A | 2/1997 | Brenner | |
| 5,641,658 A | 6/1997 | Adams et al. | |
| 5,658,734 A | 8/1997 | Brock et al. | |
| 5,750,341 A | 5/1998 | Macevicz | |
| 5,837,858 A | 11/1998 | Brennan | |
| 5,874,219 A | 2/1999 | Rava et al. | |
| 5,919,523 A | 7/1999 | Sundberg et al. | |
| 6,136,269 A | 10/2000 | Winkler et al. | |
| 6,210,891 B1 | 4/2001 | Nyren et al. | |
| 6,214,587 B1 | 4/2001 | Dattagupta et al. | |
| 6,258,568 B1 | 7/2001 | Nyren | |
| 6,274,320 B1 | 8/2001 | Rothberg et al. | |
| 6,287,768 B1 | 9/2001 | Chenchik et al. | |
| 6,287,776 B1 | 9/2001 | Hefti | |
| 6,288,220 B1 | 9/2001 | Kambara et al. | |
| 6,291,193 B1 | 9/2001 | Khodadoust | |
| 6,297,006 B1 | 10/2001 | Drmanac et al. | |
| 6,346,413 B1 | 2/2002 | Fodor et al. | |
| 6,355,431 B1 | 3/2002 | Chee et al. | |
| 6,416,949 B1 | 7/2002 | Dower et al. | |
| 6,482,591 B2 | 11/2002 | Lockhart et al. | |
| 6,514,751 B2 | 2/2003 | Johann et al. | |
| 6,524,793 B1 | 2/2003 | Chandler et al. | |
| 6,610,482 B1 | 8/2003 | Fodor et al. | |
| 6,890,741 B2 | 5/2005 | Fan et al. | |
| 6,913,884 B2 | 7/2005 | Stuelpnagel et al. | |
| 7,057,026 B2 | 6/2006 | Barnes et al. | |
| 7,115,400 B1 | 10/2006 | Adessi et al. | |
| 7,211,414 B2 | 5/2007 | Hardin et al. | |
| 7,244,559 B2 | 7/2007 | Rothberg et al. | |

(Continued)

FOREIGN PATENT DOCUMENTS

| | | |
|---|---|---|
| EP | 0 742 287 A2 | 11/1996 |
| EP | 0 799 897 A1 | 10/1997 |

(Continued)

OTHER PUBLICATIONS

Bains et al., A Novel Method for Nucleic Acid Sequence Determination, Journal of Theoretical Biology, 1988, 135(3): 303-7.
Barker et al., Tetrazine-Norbornene Click Reactions to Functionalize Degradable Polymers Derived From Lactide, Macromolecular Rapid Communications, 2011, 32(17):1362-1366.
Bentley et al., Accurate Whole Human Genome Sequencing Using Reversible Terminator Chemistry, Nature, 2008, 456: 53-59.
Chen, "Surface Modification with Polymers Using Living Radical Polymerisation and Click Chemistry", A Thesis Submitted for the Degree of PhD at the University of Warwick, 2007, Retrieved from the Internet on Apr. 11, 2016 at URL: http://wrap.warwick.ac.uk/4462/1/W RAP_THESIS_Chen_2007.pdf.

(Continued)

*Primary Examiner* — Robert S Jones
(74) *Attorney, Agent, or Firm* — Knobbe, Martens, Olson & Bear, LLP

(57) ABSTRACT

Some embodiments described herein relate to new polymer coatings for surface functionalization and new processes for grafting pre-grafted DNA-copolymers to surface(s) of substrates for use in DNA sequencing and other diagnostic applications.

22 Claims, 11 Drawing Sheets

Specification includes a Sequence Listing.

(56) References Cited

U.S. PATENT DOCUMENTS

| | | | |
|---|---|---|---|
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,582,420 | B2 | 9/2009 | Oliphant et al. |
| 7,595,883 | B1 | 9/2009 | El Gamal et al. |
| 7,622,294 | B2 | 11/2009 | Walt et al. |
| 8,778,848 | B2 | 7/2014 | Lin et al. |
| 8,778,849 | B2 | 7/2014 | Bowen et al. |
| 9,815,916 | B2 * | 11/2017 | Brown ............... C12Q 1/6874 |
| 2002/0055100 | A1 | 5/2002 | Kawashima et al. |
| 2002/0102578 | A1 | 8/2002 | Dickinson et al. |
| 2004/0002090 | A1 | 1/2004 | Mayer et al. |
| 2004/0096853 | A1 | 5/2004 | Mayer |
| 2005/0053980 | A1 | 3/2005 | Gunderson et al. |
| 2005/0064460 | A1 | 3/2005 | Holliger et al. |
| 2005/0130173 | A1 | 6/2005 | Leamon et al. |
| 2005/0181440 | A1 | 8/2005 | Chee et al. |
| 2005/0191698 | A1 | 9/2005 | Chee et al. |
| 2007/0099208 | A1 | 5/2007 | Drmanac et al. |
| 2007/0128624 | A1 | 6/2007 | Gormley et al. |
| 2008/0009420 | A1 | 1/2008 | Schroth et al. |
| 2008/0108082 | A1 | 5/2008 | Rank et al. |
| 2009/0026082 | A1 | 1/2009 | Rothberg et al. |
| 2009/0127589 | A1 | 5/2009 | Rothberg et al. |
| 2009/0186349 | A1 | 7/2009 | Gunderson et al. |
| 2010/0111768 | A1 | 5/2010 | Banerjee et al. |
| 2010/0137143 | A1 | 6/2010 | Rothberg et al. |
| 2010/0282617 | A1 | 11/2010 | Rothberg et al. |
| 2011/0059865 | A1 | 3/2011 | Smith et al. |
| 2011/0172118 | A1 | 7/2011 | Kain et al. |
| 2012/0270305 | A1 | 10/2012 | Reed et al. |
| 2014/0243224 | A1 | 8/2014 | Barnard et al. |

FOREIGN PATENT DOCUMENTS

| | | |
|---|---|---|
| WO | WO 89/10977 | 11/1989 |
| WO | WO 91/06678 | 5/1991 |
| WO | WO 93/17126 A1 | 9/1993 |
| WO | WO 95/11995 A1 | 5/1995 |
| WO | WO 95/35505 A1 | 12/1995 |
| WO | WO 00/63437 | 10/2000 |
| WO | WO 04/018497 | 3/2004 |
| WO | WO 05/010145 | 2/2005 |
| WO | WO 07/123744 | 11/2007 |
| WO | WO 2012/058096 | 5/2012 |
| WO | WO 2013/184796 | 12/2013 |

OTHER PUBLICATIONS

Chen et al., Clicking 1,2,4,5-tetrazine and Cyclooctynes with Tunable Reaction Rates, Chem. Commun., 2012, 48: 1736-1738.

Cheng et al., A Facile Method for the Preparation of Thermally Remendable Cross-Linked Polyphosphazenes, Journal of Polymer Science, Part A: Polymer Chemistry, 2013, 51: 1205-1214.

Dean et al., Comprehensive Human Genome Amplification Using Multipole Displacement Amplification, Proc. Natl. Acad. Sci., 2002, 99: 5261-66.

Dressman et al., Transforming Single DNA Molecules into Fluorescent Magnetic Particles for Detection and Enumeration of Genetic Variations, Proc. Natl. Acad. Sci., 2003, 100: 8817-8822.

Drmanac et al., Accurate Sequencing by Hybridization for DNA Diagnostics and Individual Genomics, Nature Biotechnology, 1998, 16: 54-58.

Fodor et al., Light-Directed, Spatially Addressable Parallel Chemical Synthesis, Science, 1991, 251(4995): 767-773.

Korlach et al., Selective Aluminum Passivation for Targeted Immobilization of Single DNA Polymerase Molecules in Zero-Mode Waveguide Nanostructures, Proc. Natl. Acad. Sci., 2008, 105, 1176-1181.

Lage et al., Whole Genome Analysis of Genetic Alterations in Small DNA Samples Using Hyperbranched Strand Displacement Amplification and Array—CGH, Genome Research, 2003, 13:294-307.

Levene et al., Zero-Mode Waveguides for Single-Molecule Analysis at High Concentrations, Science, 2003, 299: 682-686.

Lizardi et al., Mutation Detection and Single-Molecule Counting Using Isothermal Rolling-Circle Amplification, Nat. Genet., 1998, 19:225-232.

Lundquist et al., Parallel Confocal Detection of Single Molecules in Real Time, Opt. Lett., 2008, 33, 1026-1028.

Qiu et al., Reverse Self-Assemblies Based on Amphiphilic Polyphosphazenes for Encapsulation of Water-Soluble Molecules, Nanotechnology, 2007, 18, 475602.

Ronaghi, et al., Real-Time DNA Sequencing Using Detection of Pyrophosphate Release, Analytical Biochemistry, 1996, 242(1), 84-9.

Ronaghi et al., A Sequencing Method Based on Real-Time Pyrophosphate, Science, 1998, 281(5375), 363.

Ronaghi, Pyrosequencing Sheds Light on DNA Sequencing, Genome Res., 2001, 11(1), 3-11.

Shendure et al., Accurate Multiplex Polony Sequencing of an Evolved Bacterial Genome, Science, 2005, 309:1728-1732.

Sumerlin, et al., "Highly Efficient "Click" Functionalization of Poly(3-azidopropyl methacrylate) Prepared by ATRP", Macromolecules, 2005, vol. 38, pp. 7540-7545.

Walker et al., Strand Displacement Amplification—An Isothermal, In Vitro DNA Amplification Technique, Nucl. Acids Res., 1992, 20:1691-96.

Walker et al., (1995) A chemiluminescent DNA probe test based on strand displacement amplification. In Danny L. Wiedbrauk and Daniel H. Farkas (Eds.), *Molecular Methods for Virus Detection* (pp. 329-349). San Diego: Academic Press, Inc.

International Search Report and Written Opinion of the International Searching Authority issued in PCT/EP2015/074759, dated Apr. 20, 2016.

* cited by examiner

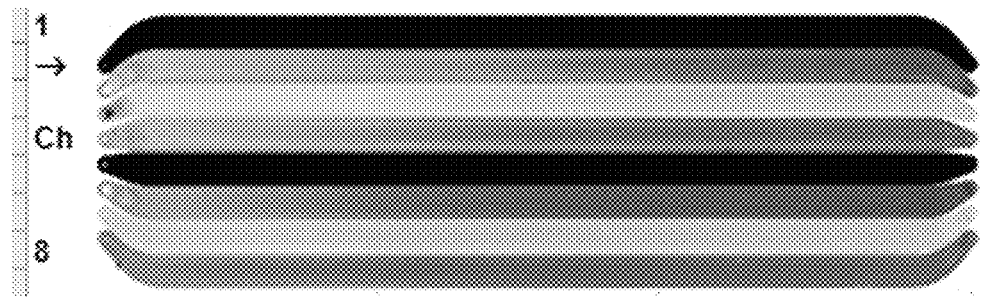
FIG. IA
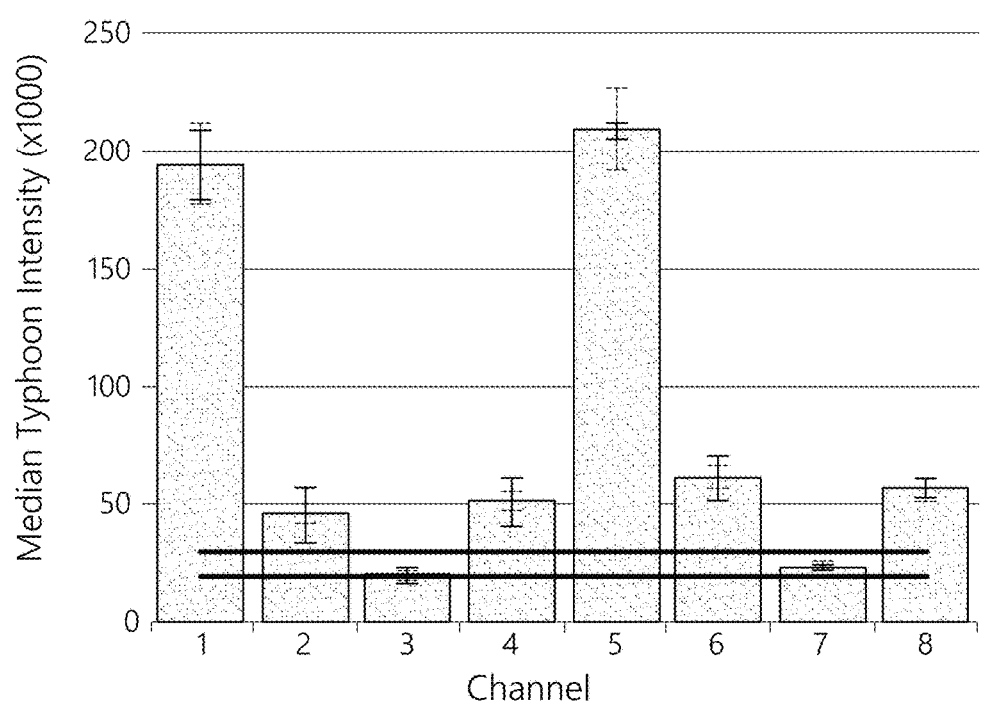
FIG. IB

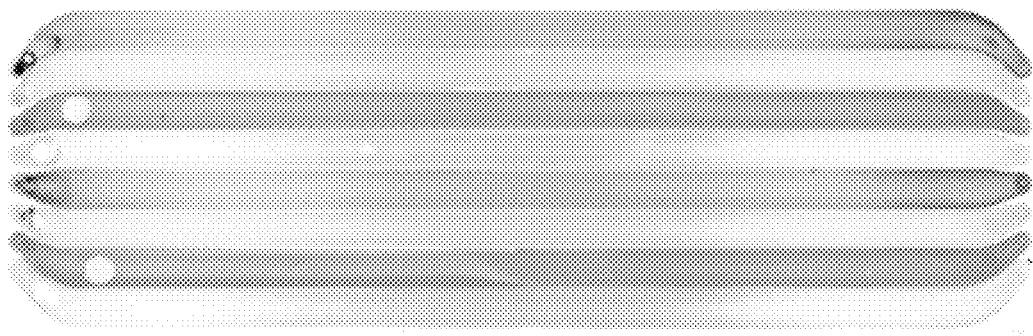
FIG. IC
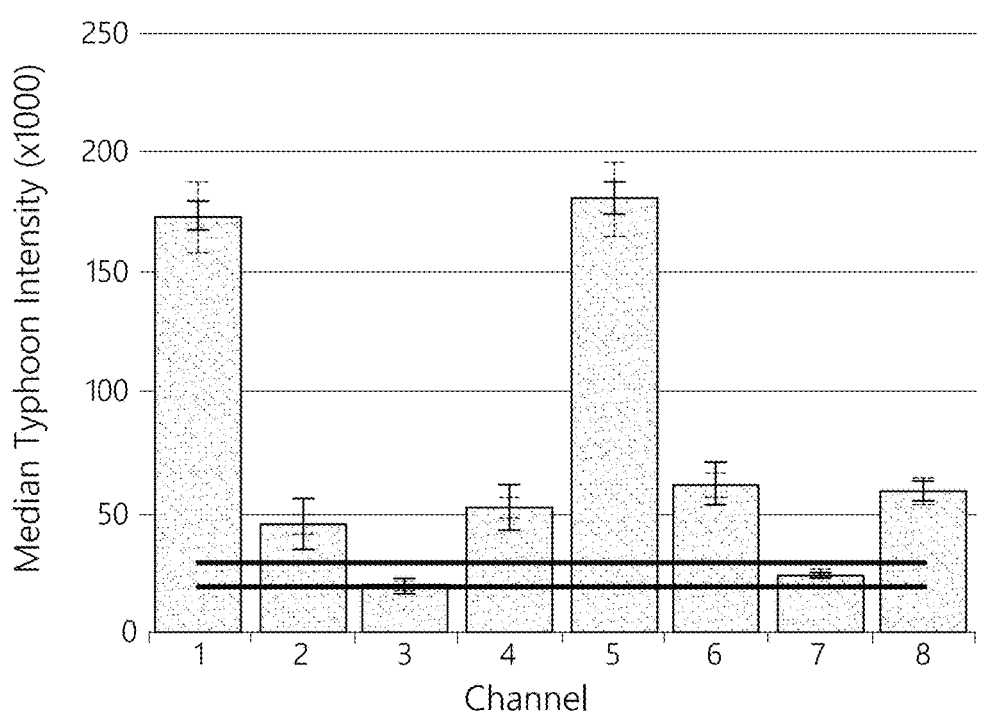
FIG. ID

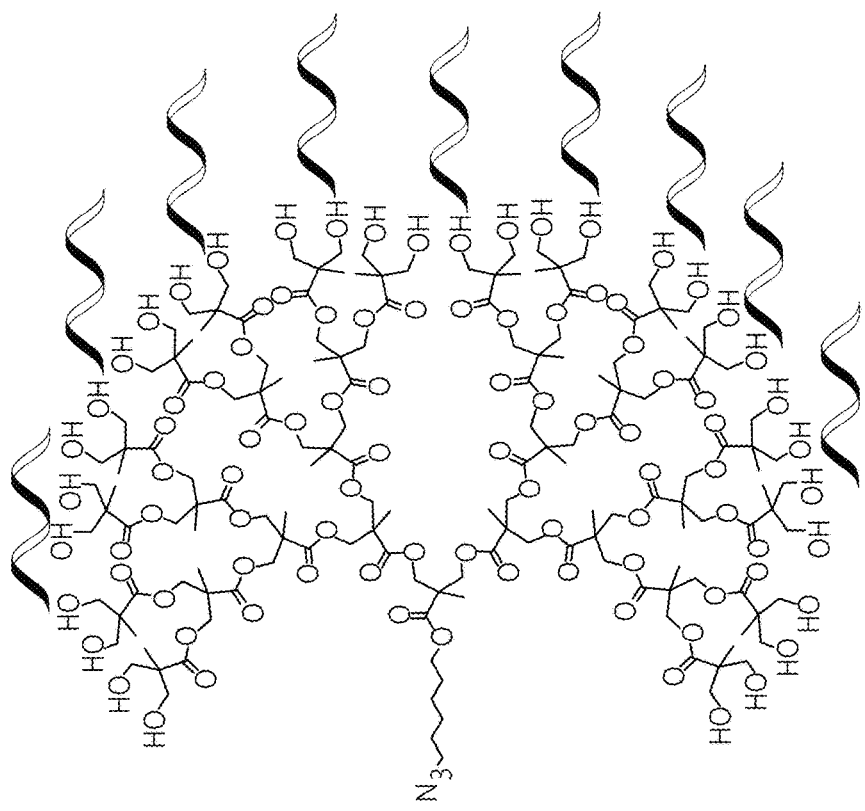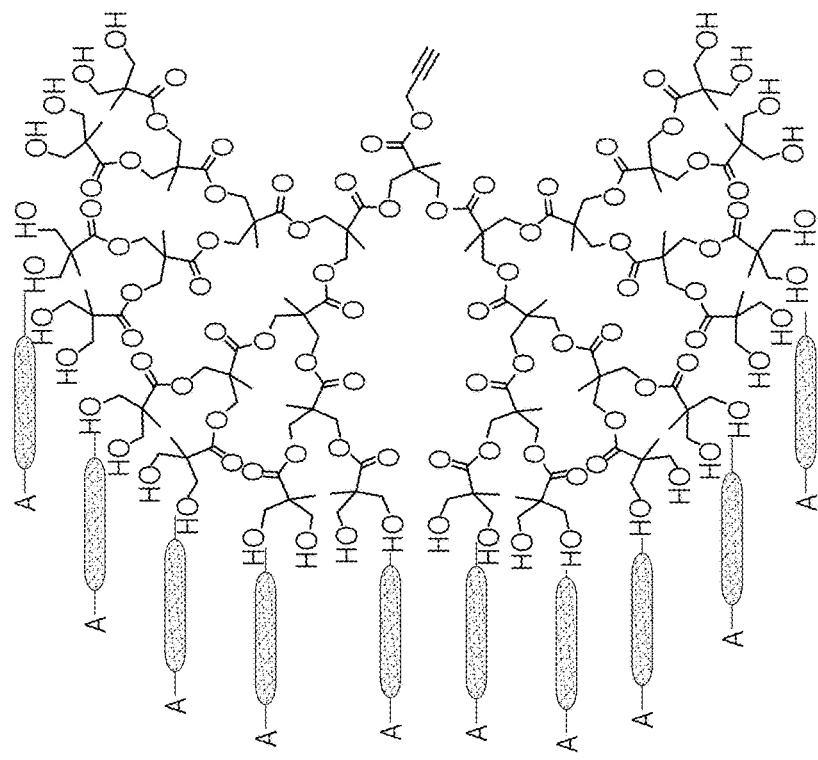
FIG. 7

SEQUENCE LISTING

<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: Artificially Synthesized Primer

<400> SEQUENCE: 1
aatgatacgg cgaccaccga gauctacac                               29

<210> SEQ ID NO 2
<211> LENGTH: 24
<212> TYPE: DNA
<213> ORGANISM: Artificial Sequence
<220> FEATURE:
<223> OTHER INFORMATION: Artificially Synthesized Primer

<400> SEQUENCE: 2
caagcagaag acggcatacg agat                                    24

<210> SEQ ID NO 3
<211> LENGTH: 20
<212> TYPE: DNA
<213> ORGANISM: Artificial Sequence
<220> FEATURE:
<223> OTHER INFORMATION: Artificially Synthesized Primer

<400> SEQUENCE: 3
aatgatacgg cgaccaccga                                         20

```
<210> SEQ ID NO 4
<211> LENGTH: 21
<212> TYPE: DNA
<213> ORGANISM: Artificial Sequence
<220> FEATURE:
<223> OTHER INFORMATION: Artifically Synthesized Primer

<400> SEQUENCE: 4
caagcagaag acggcatacg a                                              21
```

POLYMERS AND DNA COPOLYMER COATINGS

INCORPORATION BY REFERENCE TO PRIORITY APPLICATIONS

The present application is a continuation of U.S. patent application Ser. No. 14/927,252, filed Oct. 29, 2015, which claims the benefit of priority to U.S. Provisional Patent Application No. 62/073,764, filed on Oct. 31, 2014, each of which is hereby expressly incorporated by reference in its entirety.

REFERENCE TO SEQUENCE LISTING

The present application includes a sequence listing in Electronic format. The Sequence Listing is provided as a file entitled IP-1240A-US.txt, created Nov. 9, 2017, which is approximately 2 KB in size. The information in the electronic format of the sequence listing is incorporated herein by reference in its entirety.

FIELD

In general, the present application relates to the fields of chemistry, biology and material science. More specifically, the present application relates to novel polymer coatings and grafted DNA-copolymers to support substrate surface functionalization and downstream applications, such as DNA sequencing and other diagnostic applications. Methods for preparing such functionalized surface and the use thereof are also disclosed.

BACKGROUND

Polymer or hydrogel-coated substrates are used in many technological applications. For example, implantable medical devices can be coated with biologically inert polymers. In another example, polymer or hydrogel coated substrates are used for the preparation and/or analysis of biological molecules. Molecular analyses, such as certain nucleic acid sequencing methods, rely on the attachment of nucleic acid strands to a polymer or hydrogel-coated surface of a substrate. The sequences of the attached nucleic acid strands can then be determined by a number of different methods that are well known in the art.

In certain Sequencing-by-Synthesis ("SBS") processes, one or more surfaces of a flow cell are coated with a polymer or a hydrogel to which primers (single stranded DNA or ssDNA) are then grafted. However, there is an inherent cost associated with performing the coating, grafting and quality control steps.

SUMMARY

The present application discloses polymer coatings that are useful for SBS applications and processes of incorporating the primer polymer coupling steps into the initial polymer synthesis. This may eliminate some or all of the grafting process undertaken to manufacture a sequencing flow cell or other substrate used for SBS. These processes may maximize primer accessibility to the downstream biochemistry, minimize side reactions and yield a more efficient surface chemistry. The coatings and processes disclosed herein are useful for other analytical apparatus and processes including, but not limited to, those used for synthesis or detection of nucleic acids and other biologically active molecules.

Some embodiments described herein are related to a polymer for surface functionalization, comprising a recurring unit of Formula (I) and a recurring unit of Formula (II):

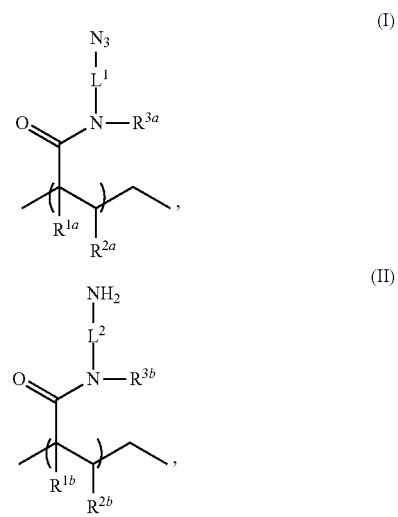

wherein each $R^{1a}$, $R^{2a}$, $R^{1b}$ and $R^{2b}$ is independently selected from hydrogen, optionally substituted alkyl or optionally substituted phenyl; each $R^{3a}$ and $R^{3b}$ is independently selected from hydrogen, optionally substituted alkyl, optionally substituted phenyl, or optionally substituted $C_{7-14}$ aralkyl; and each $L^1$ and $L^2$ is independently selected from an optionally substituted alkylene linker or an optionally substituted heteroalkylene linker. In some embodiments, the polymer may further comprise one or more recurring units selected from the group consisting of polyacrylamides, polyacrylates, polyurethanes, polysiloxanes, silicones, polyacroleins, polyphosphazenes, polyisocyanates, poly-ols, and polysaccharides, or combinations thereof. In some such embodiments, the polymer may further comprise one or more recurring units of polyacrylamide of Formula (IIIa) or (IIIb) or both:

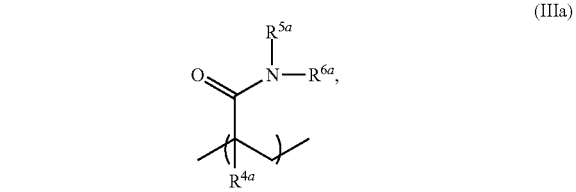

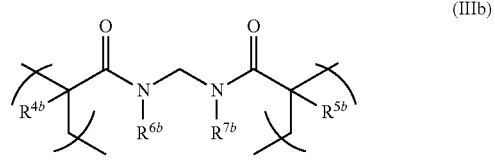

wherein each $R^{4a}$, $R^{4b}$ and $R^{5b}$ is selected from hydrogen or $C_{1-3}$ alkyl; and each $R^{5a}$, $R^{6a}$, $R^{6b}$ and $R^{7b}$ is independently selected from hydrogen, optionally substituted $C_{1-6}$ alkyl or optionally substituted phenyl.

Some embodiments described herein are related to a substrate having a first surface comprising a polymer with a recurring unit of Formula (I) and a recurring unit of Formula (II) as described herein. In some embodiments, the polymer may further comprise one or more recurring units of various different polymer backbones as described above, for example, one or more recurring units of polyacrylamide of Formula (IIIa) or (IIIb) or both.

In some embodiments, when the polymer is covalently attached to the first surface of the substrate, at least one covalent bond is formed between the amino group of the recurring unit of Formula (II) and the first surface of the substrate. Therefore, as described herein, a substrate having a first surface comprising a polymer with a recurring unit of Formula (I) and a recurring unit of Formula (II) covalently bonded thereto, should be understood to also include the polymer with a modified recurring unit of the structure

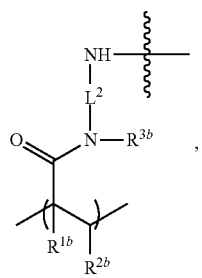

showing the covalent bonding position with the substrate surface.

Some embodiments described herein are related to a grafted polymer comprising functionalized oligonucleotides covalently bonded to a polymer with a recurring unit of Formula (I) and a recurring unit of Formula (II) as described herein. In some embodiments, the polymer may further comprise one or more recurring units of various different polymer backbones as described above, for example, one or more recurring units of polyacrylamide of Formula (IIIa) or (IIIb) or both.

In some embodiments, when functionalized oligonucleotides are covalently bonded to the polymer, at least two covalent bonds are formed as the result of a reaction between the azido group of the recurring unit of Formula (I) and a functionalized oligonucleotide. Therefore, as described herein, a grafted polymer comprising functionalized oligonucleotides covalently bonded to a polymer of a recurring unit of Formula (I) and a recurring unit of Formula (II), should be understood to also include the polymer with a modified recurring unit of the structure

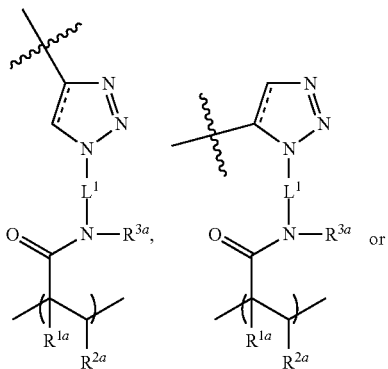

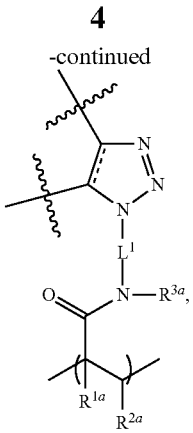

showing the covalent bonding position with functionalized oligonucleotide, wherein ----- is a single or double bond.

Some embodiments described herein are related to a polymer for surface functionalization, comprising a recurring unit of Formula (IV):

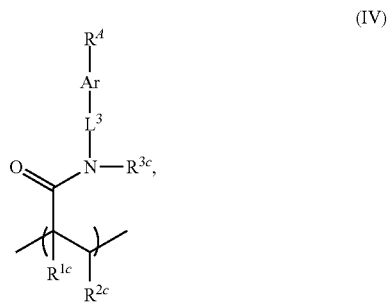

wherein each $R^{1c}$ and $R^{2c}$ is independently selected from hydrogen, optionally substituted alkyl or optionally substituted phenyl; $R^{3c}$ is selected from hydrogen, optionally substituted alkyl, optionally substituted phenyl, or optionally substituted $C_{7-14}$ aralkyl; Ar is selected from an optionally substituted $C_{6-10}$ aryl or an optionally substituted 5 or 6 membered heteroaryl; $R^A$ is optionally substituted tetrazine; and $L^3$ is selected from a single bond, an optionally substituted alkylene linker or an optionally substituted heteroalkylene linker. In some embodiments, the polymer may further comprise one or more recurring units selected from the group consisting of polyacrylamides, polyacrylates, polyurethanes, polysiloxanes, silicones, polyacroleins, polyphosphazenes, polyisocyanates, poly-ols, and polysaccharides, or combinations thereof. In some such embodiments, the polymer may further comprise one or more recurring units of polyacrylamide of Formula (IIIa) or (IIIb) or both, with the structure shown above.

Some embodiments described herein are related to a substrate having a first surface comprising a polymer with a recurring unit of Formula (IV) as described herein. In some embodiments, the polymer may further comprise one or more recurring units of various different polymer backbones as described above, for example, one or more recurring units of polyacrylamide of Formula (IIIa) or (IIIb) or both.

In some embodiments, when the polymer is covalently attached to the first surface of the substrate, at least two covalent bonds are formed as the result of a reaction between the tetrazine group of the recurring unit of Formula (IV) and the first surface of the substrate. In some other embodiments, at least two covalent bonds are formed between the tetrazine group of the recurring unit of Formula (IV). Therefore, as described herein, a substrate having a first surface comprising a polymer with a recurring unit of Formula (IV) as described herein, should be understood to also include the polymer with a modified recurring unit of the structure

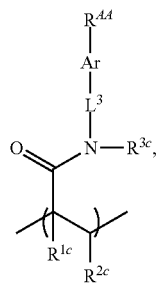

wherein the moiety Ar—$R^{AA}$ is selected from

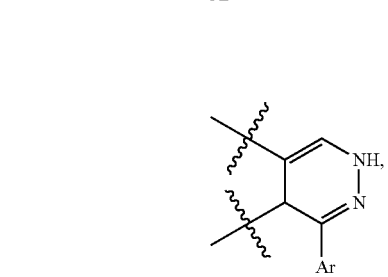

showing the covalent bonding position with the substrate surface; and wherein ----- is a single or double bond. $R^{AA}$ may be optionally substituted.

Some embodiments described herein are related to a grafted polymer comprising functionalized oligonucleotides covalently bonded to a polymer with a recurring unit of Formula (IV) as described herein. In some embodiments, the polymer may further comprise one or more recurring units of various different polymer backbones as described above, for example, one or more recurring units of polyacrylamide of Formula (IIIa) or (IIIb) or both.

In some embodiments, when functionalized oligonucleotides are covalently bonded to the polymer, at least two covalent bonds are formed as the result of a reaction between the tetrazine group of the recurring unit of Formula (IV) and a functionalized oligonucleotide. Therefore, as described herein, a grafted polymer comprising functionalized oligonucleotides covalently bonded to a polymer of a recurring unit of Formula (IV), should be understood to also include the polymer with a modified recurring unit of the structure

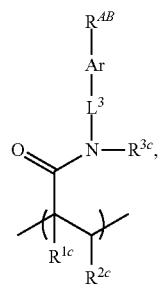

wherein the moiety Ar—$R^{AB}$ is selected from

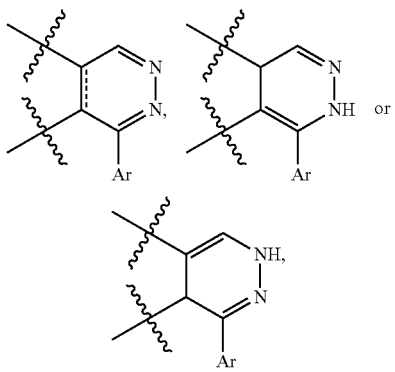

showing the covalent bonding position with the oligonucleotide; and wherein ----- is a single or double bond. $R^{AB}$ may be optionally substituted.

Some embodiments described herein are related to a polymer for surface functionalization, comprising a recurring unit of Formula (V):

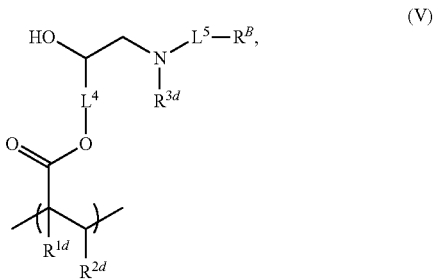

(V)

wherein each $R^{1d}$ and $R^{2d}$ is independently selected from hydrogen, optionally substituted alkyl or optionally substituted phenyl; each $R^{3d}$ is selected from hydrogen, optionally substituted alkyl, optionally substituted phenyl, or optionally substituted $C_{7-14}$ aralkyl; $R^B$ is selected from azido, optionally substituted amino, Boc-protected amino, hydroxy, thiol, alkynyl, alkenyl, halo, epoxy, tetrazinyl or aldehyde; each $L^4$ and $L^5$ is independently selected from an optionally substituted alkylene linker or an optionally substituted heteroalkylene linker. In some embodiments, the polymer may further comprise a recurring unit of Formula (VIa) or (VIb), or both:

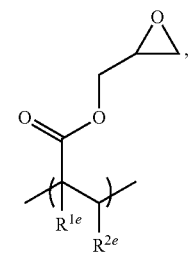
(VIa)

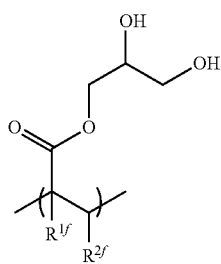
(VIb)

wherein each $R^{1e}$, $R^{2e}$, $R^{1f}$ and $R^{2f}$ is independently selected from hydrogen, optionally substituted alkyl or optionally substituted phenyl. In some embodiments, the polymer may further comprise one or more recurring units selected from the group consisting of polyacrylamides, polyacrylates, polyurethanes, polysiloxanes, silicones, polyacroleins, polyphosphazenes, polyisocyanates, poly-ols, and polysaccharides, or combinations thereof.

Some embodiments described herein are related to a substrate having a first surface comprising a polymer with a recurring unit of Formula (V) as described herein. In some embodiments, the polymer may further comprise a recurring unit of Formula (VIa) or (VIb), or both. In some embodiments, the polymer may further comprise one or more recurring units of various different polymer backbones as described above.

In some embodiments, when the polymer is covalently attached to the first surface of the substrate, at least two covalent bonds are formed as the result of a reaction between the azido group of the recurring unit of Formula (V) and the first surface of the substrate. Therefore, as described herein, a substrate having a first surface comprising a polymer with a recurring unit of Formula (V) covalently bonded thereto, should be understood to also include the polymer with a modified recurring unit of the structure

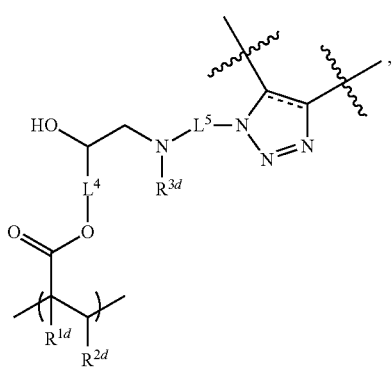

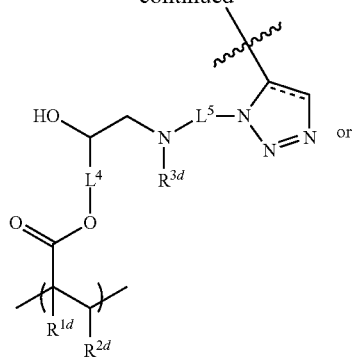

showing the covalent bonding position with the substrate surface.

In some other embodiments, when the polymer is covalently attached to the first surface of the substrate, at least one covalent bond is formed between the amino group of the recurring unit of Formula (V) and the first surface of the substrate. Therefore, as described herein, a substrate having a first surface comprising a polymer with a recurring unit of Formula (V) covalently bonded thereto, should be understood to also include the polymer with a modified recurring unit of the structure

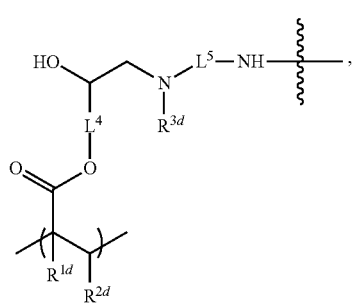

showing the covalent bonding position with the substrate surface.

Some embodiments described herein are related to a grafted polymer comprising functionalized oligonucleotides covalently bonded to a polymer with a recurring unit of Formula (V) as described herein. In some embodiments, the polymer may further comprise a recurring unit of Formula (VIa) or (VIb), or both. In some embodiments, the polymer may further comprise one or more recurring units of various different polymer backbones as described above.

In some embodiments, when functionalized oligonucleotides are covalently bonded to the polymer, at least one covalent bond is formed as the result of a reaction between the epoxy group of the recurring unit of Formula (VIa) and a functionalized oligonucleotide. Therefore, as described herein, a grafted polymer comprising functionalized oligonucleotides covalently bonded to a polymer of a recurring unit of Formula (V) and a recurring unit of Formula (VIa), should be understood to also include the polymer with a modified recurring unit of the structure

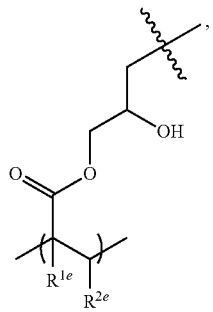

showing the covalent bonding position with the oligonucleotide.

Some embodiments described herein are related processes for immobilizing a grafted polymer to a first surface of a substrate, comprising:

providing a substrate having a first surface comprising a first plurality of functional groups covalently attached thereto;

providing a grafted polymer comprising functionalized oligonucleotides covalently bonded to a polymer, wherein the polymer comprises a second plurality of functional groups; and reacting the first plurality functional groups of the first surface with the second plurality of functional groups of the polymer such that the polymer is covalently bonded to the first surface of the substrate.

In some embodiments of the methods described herein, when the surface is treated with functionalized silane comprising unsaturated moieties selected from cycloalkenes, cycloalkynes, heterocycloalkenes, heterocycloalkynes; and the functionalized oligonucleotides comprise bicyclo[6.1.0] non-4-yne; then the polymer is not a poly(N-(5-azidoacetamidylpentyl) acrylamide-co-acrylamide) (PAZAM) of the following structure:

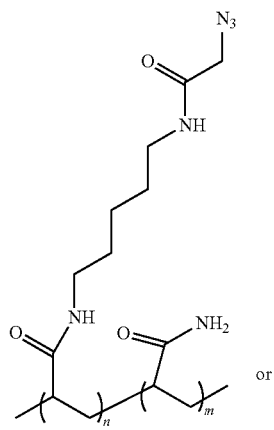

or

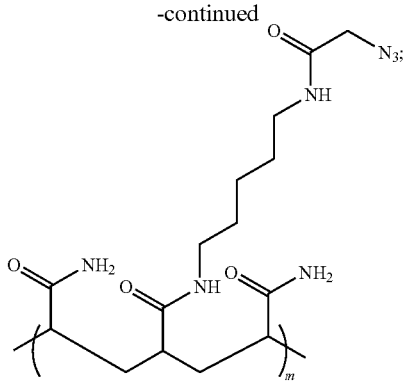

wherein n is an integer in the range of 1-20,000, and m is an integer in the range of 1-100,000. In some such embodiments, the unsaturated moieties of the functionalized silane comprise norbornene.

Some embodiments described herein are related processes or methods for immobilizing a polymer described herein to a first surface of a substrate, comprising: providing a substrate having a first surface comprising a first plurality of functional groups covalently attached thereto; providing a polymer described herein; and reacting the first plurality functional groups of the first surface with the polymer such that the polymer is covalently bonded to the first surface of the substrate.

BRIEF DESCRIPTION OF THE DRAWINGS

FIGS. 1A to 1D show the Typhoon florescence image of the polymers coated flow cell with norbornene silane monolayer surface and the related bar chart of median Typhoon intensity of the polymers of Example 1 (Table 2).

FIG. 7 shows the coupling reaction between a grafted dendrimer and a functionalized dendrimer with surface attachment groups.

DETAILED DESCRIPTION

Figure 2A:
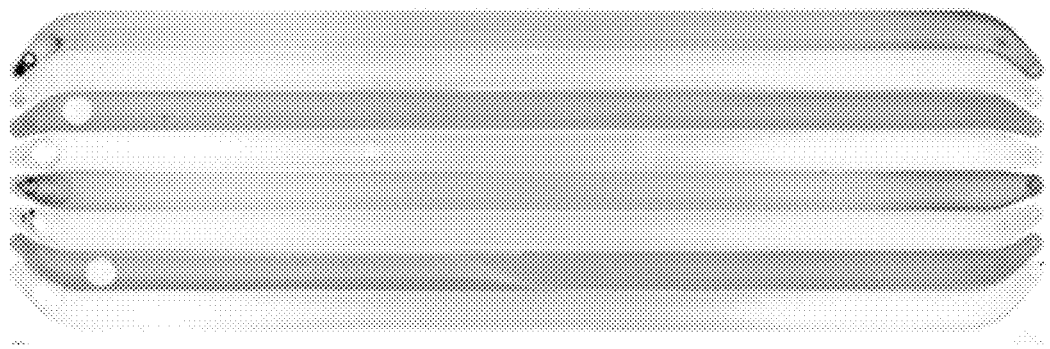
FIGS. 2A to 2D show the Typhoon florescence image of the polymers coated flow cell with norbornene silane monolayer surface and the related bar chart of median Typhoon intensity of the polymers of Example 1 (Table 3).
Figure 2B:
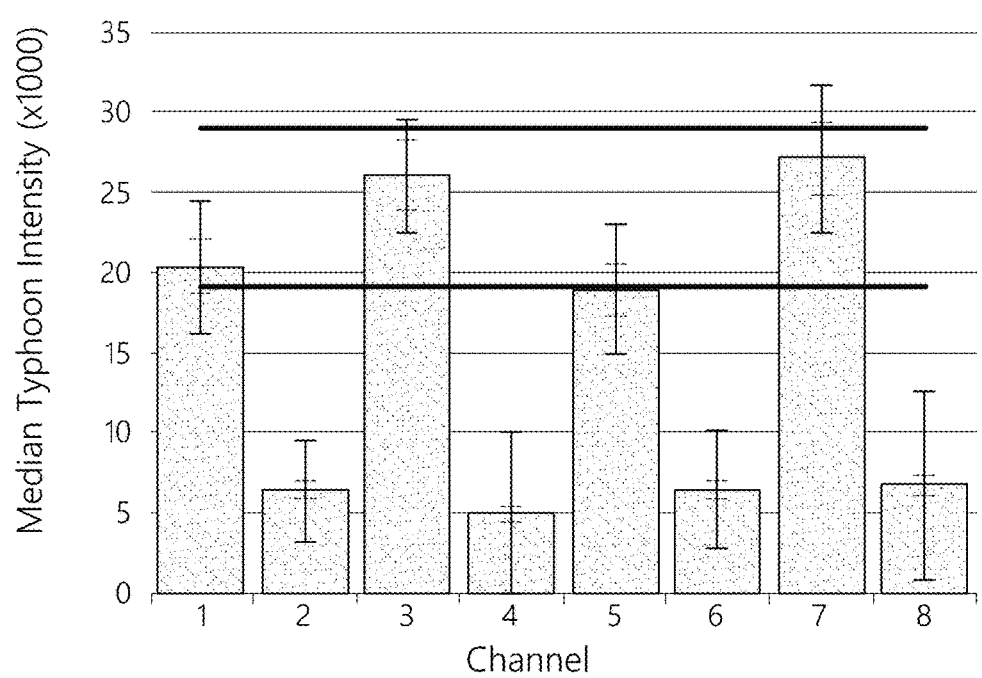
Figure 2C:
Figure 2D:
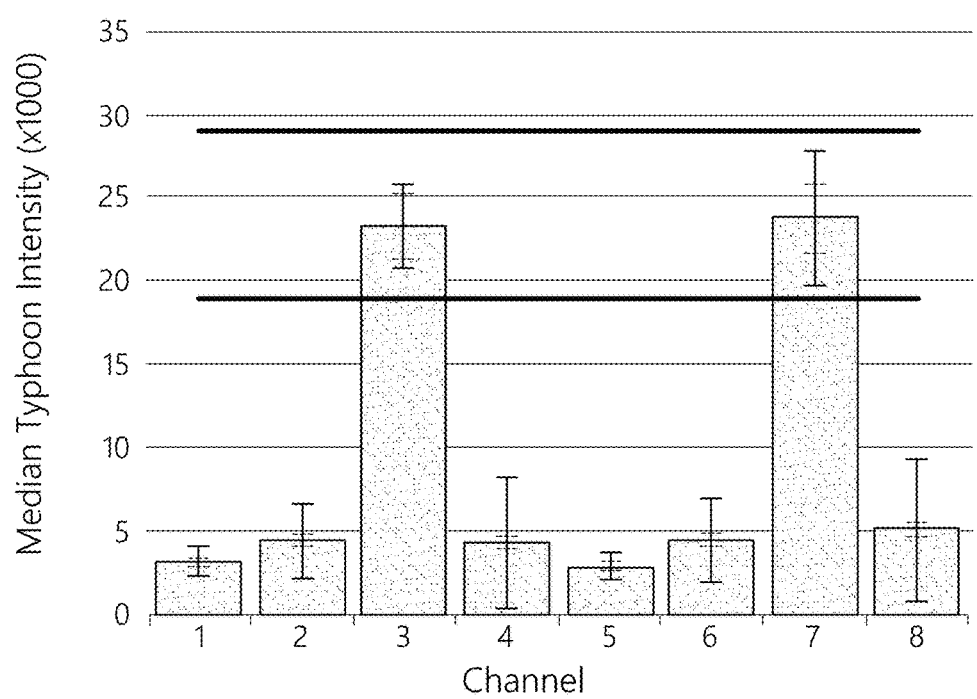

The present application relates to nucleic acid-copolymers (for example, DNA-copolymers and processes for grafting such nucleic acid-copolymers to the surface of a substrate. Some embodiments of polymers used for pre-conjugation with single stranded DNA ("ssDNA") primers include acrylamide/azido-acrylamide/aminoethyl-acrylamide ternary copolymers, tetrazine modified polyacrylamide, and the reaction products of poly(glycidyl methacrylate) with amino-PEG-azide or amino-PEG-Boc-amide. The nucleic acid-copolymer can then be covalently attached to a surface of a substrate, in some instances, a silane functionalized surface of a substrate, such as a surface of a flow cell or a surface of a molecular array. The present disclosure also relates to methods of preparing such nucleic acid-copolymer coated surfaces and methods of using substrates comprising such nucleic acid-copolymer coated surfaces in sequencing-by-synthesis reactions.

Some embodiments relate to flow cells for performing sequencing-by-synthesis reactions that include functionalized oligonucleotides pre-conjugated to a polymer described herein through one or more functional moieties, such as bicyclo[6.1.0]non-4-yne, alkyne, amido or azido derivatized linkage. In some embodiments, the primers are a P5 or P7 primer. The P5 and P7 primers are used on the surface of commercial flow cells sold by Illumina Inc. for sequencing on the HiSeq®, MiSeq®, NextSeq® and Genome Analyzer® platforms.

Further process and cost savings may be achieved by incorporating quality control (QC) markers within the polymer along with the primer attachment. Analytical tests may be used to determine the quality and consistency of the DNA-copolymer with or without QC markers, and used again to determine effectiveness of deposition when working with an open wafer format. These additional quality control checkpoints should reduce flow cell batch to batch variation to yield more consistent products, and also help narrow down where process deviation has occurred when failures during manufacturing appear.

Definitions

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

As used herein, common organic abbreviations are defined as follows:
Ac Acetyl
Ac$_2$O Acetic anhydride
APTS aminopropyl silane
APTES (3-aminopropyl)triethoxysilane
APTMS (3-aminopropyl)trimethoxysilane
aq. Aqueous
ATRP Atom-transfer radical polymerization
Azapa N-(5-azidoacetamidylpentyl) acrylamide
BCN Bicyclo[6.1.0] non-4-yne
Bn Benzyl
Brapa or BRAPA N-(5-bromoacetamidylpentyl) acrylamide
Bz Benzoyl
BOC or Boc tert-Butoxycarbonyl
Bu n-Butyl
cat. Catalytic
CMP Chemical mechanical polishing
CRP Controlled radical polymerization
CVD Chemical vapor deposition
° C. Temperature in degrees Centigrade
dATP Deoxyadenosine triphosphate
dCTP Deoxycytidine triphosphate
dGTP Deoxyguanosine triphosphate
dTTP Deoxythymidine triphosphate
DCA Dichloroacetic acid
DCE 1,2-Dichloroethane
DCM Methylene chloride
DIEA Diisopropylethylamine
DIPEA Diisopropylethylamine
DMA Dimethylacetamide
DME Dimethoxyethane
DMF N,N'-Dimethylformamide
DMSO Dimethylsulfoxide
DPPA Diphenylphosphoryl azide
Et Ethyl
EtOAc or EA Ethyl acetate
g Gramme(s)
h or hr Hour(s)
iPr Isopropyl
KPi 10 mM potassium phosphate buffer at pH 7.0
KPS Potassium persulfate
IPA Isopropyl Alcohol
IPHA.HCl N-Isopropylhydroxylamine hydrochloride
m or min Minute(s)
MeOH Methanol
MeCN Acetonitrile
mL Milliliter(s)
NaN$_3$ Sodium Azide
NHS N-hydroxysuccinimide
NMP Nitroxide-mediated radical polymerisation
PAZAM poly(N-(5-azidoacetamidylpentyl) acrylamide-co-acrylamide) of any acrylamide to Azapa ratio
PEG Polyethylene glycol
PG Protecting group
PGMA Poly(glycidyl methacrylate)
Ph Phenyl
ppt Precipitate
RAFT Reversible addition-fragmentation chain transfer polymerisation
rt Room temperature
SFA Silane Free Acrylamide as defined in U.S. Pat. Pub. No. 2011/0059865
Sulfo-HSAB or SHSAB N-Hydroxysulfosuccinimidyl-4-azidobenoate
TEA Triethylamine Tert, t tertiary
THF Tetrahydrofuran
TEMED Tetramethylethylenediamine
YES Yield Engineering Systems
μL Microliter(s)

As used herein, the term "array" refers to a population of different probe molecules that are attached to one or more substrates such that the different probe molecules can be differentiated from each other according to relative location. An array can include different probe molecules that are each located at a different addressable location on a substrate. Alternatively or additionally, an array can include separate substrates each bearing a different probe molecule, wherein the different probe molecules can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B1, US 2002/0102578 and PCT Publication No. WO 00/63437. Exemplary formats that can be used in the invention to distinguish beads in a liquid array, for example, using a microfluidic device, such as a fluorescent activated cell sorter (FACS), are described, for example, in U.S. Pat. No. 6,524,793. Further examples of arrays that can be used in the invention include, without limitation, those described in U.S. Pat Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like. The alkyl group can be optionally substituted.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like. The alkoxy group can be optionally substituted.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like. The alkenyl group can be optionally substituted.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like. The alkynyl group can be optionally substituted.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20,000 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, the term "heteroalkylene" refers to an alkylene chain in which one or more skeletal atoms of the alkylene are selected from an atom other than carbon, e.g., oxygen, nitrogen, sulfur, phosphorus or combinations thereof. The heteroalkylene chain can have a length of 2 to 20,000. Exemplary heteroalkylenes include, but are not limited to, —$OCH_2$—, —$OCH(CH_3)$—, —$OC(CH_3)_2$—, —$OCH_2CH_2$—, —$CH(CH_3)O$—, —$CH_2OCH_2$—, —$CH_2OCH_2CH_2$—, —$SCH_2$—, —$SCH(CH_3)$—, —$SC(CH_3)_2$—, —$SCH_2CH_2$—, —$CH_2SCH_2CH_2$—, —$NHCH_2$—, —$NHCH(CH_3)$—, —$NHC(CH_3)_2$—, —$NHCH_2CH_2$—, —$CH_2NHCH_2$—, —$CH_2NHCH_2CH_2$—, and the like.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20,000 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

As used herein, "alkynylene" means a straight or branched chain di-radical chemical group containing only carbon and hydrogen and containing at least one carbon-carbon triple bond that is attached to the rest of the molecule via two points of attachment.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl. The aryl group can be optionally substituted.

As used herein, "arylene" refers to an aromatic ring or ring system containing only carbon and hydrogen that is attached to the rest of the molecule via two points of attachment.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl. The heteroaryl group can be optionally substituted.

As used herein, "heteroarylene" refers to an aromatic ring or ring system containing one or more heteroatoms in the ring backbone that is attached to the rest of the molecule via two points of attachment.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3, 4, 5, 6, 7, 8, 9 or 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro [4.4]nonanyl.

As used herein, "cycloalkyl" means a fully saturated carbocyclyl ring or ring system. Examples include cyclopropyl, cyclobutyl, cyclopentyl, and cyclohexyl.

As used herein, "cycloalkylene" means a fully saturated carbocyclyl ring or ring system that is attached to the rest of the molecule via two points of attachment.

As used herein, "cycloalkenyl" or "cycloalkene" means a carbocyclyl ring or ring system having at least one double bond, wherein no ring in the ring system is aromatic. An example is cyclohexenyl or cyclohexene. Another example is norbornene or norbornenyl.

As used herein, "heterocycloalkenyl" or "heterocycloalkene" means a carbocyclyl ring or ring system with at least one heteroatom in ring backbone, having at least one double bond, wherein no ring in the ring system is aromatic. In some embodiments, heterocycloalkenyl or heterocycloalkene ring or ring system is 3-membered, 4-membered, 5-membered, 6-membered, 7-membered, 8-membered, 9 membered, or 10 membered.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne.

As used herein, "heterocycloalkynyl" or "heterocycloalkyne" means a carbocyclyl ring or ring system with at least one heteroatom in ring backbone, having at least one triple bond, wherein no ring in the ring system is aromatic. In some embodiments, heterocycloalkynyl or heterocycloalkyne ring or ring system is 3-membered, 4-membered, 5-membered, 6-membered, 7-membered, 8-membered, 9 membered, or 10 membered.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, "heterocyclylene" means a non-aromatic cyclic ring or ring system containing at least one heteroatom that is attached to the rest of the molecule via two points of attachment.

As used herein, "acyl" refers to —C(═O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(═O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-carboxy" group refers to a "—C(═O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(═O)OH).

An "acetal" group refers to $RC(H)(OR')_2$, in which R and R' are independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "cyano" group refers to a "—CN" group.

A "sulfinyl" group refers to an "—S(═O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—$SO_2R$" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—$N(R_A)SO_2R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(═O)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—$N(R_A)OC(═O)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —NH$_2$).

The term "hydrazine" or "hydrazinyl" as used herein refers to a —NHNH$_2$ group.

The term "hydrazone" or "hydrazonyl" as used herein refers to a

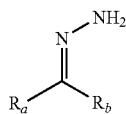

group.

The term "formyl" as used herein refers to a —C(O)H group.

The term "hydroxy" as used herein refers to a —OH group.

The term "azido" as used herein refers to a —N$_3$ group.
The term "thiol" as used herein refers to a —SH group.
The term "glycidyl ether" as used herein refers to

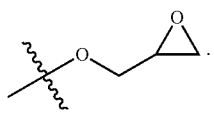

The term "epoxy" as used herein refers to

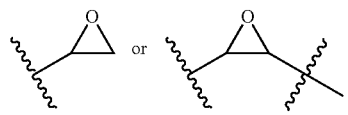

The term "ester" as used herein refers to R—C(=O)O—R', wherein R and R' can be independently alkyl, alkenyl, alkynyl, cycloalkyl, cycloalkenyl, cycloalkynyl, aryl, heteroaryl, heteroalicyclyl, aralkyl, (heteroalicyclyl)alkyl, or optionally substituted variants thereof.

The term "carboxylic acid" or "carboxyl" as used herein refers to —C(O)OH.

As used herein, the term "tetrazine" or "tetrazinyl" refers to six-membered heteroaryl group comprising four nitrogen atoms. Tetrazine can be optionally substituted.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —CF$_3$), halo($C_1$-$C_6$)alkoxy (e.g., —OCF$_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

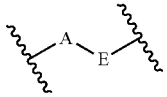

includes the substituent being oriented such that the A is attached at the leftmost attachment point of the molecule as well as the case in which A is attached at the rightmost attachment point of the molecule.

Where the compounds disclosed herein have at least one stereocenter, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

As used herein, a "nucleotide" includes a nitrogen containing heterocyclic base, a sugar, and one or more phosphate groups. They can be monomeric units (whether precursors or linked monomers) of a nucleic acid sequence. In RNA, the sugar is a ribose, and in DNA a deoxyribose, i.e. a sugar lacking a hydroxyl group that is present at the 2' position in ribose. The nitrogen containing heterocyclic base can be purine or pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but lacks any phosphate moieties at the 5' position. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

As used herein, the term "polynucleotide" refers to nucleic acids in general, including DNA (e.g. genomic DNA cDNA), RNA (e.g. mRNA), synthetic oligonucleotides and synthetic nucleic acid analogs. Polynucleotides may include natural or non-natural bases, or combinations thereof and natural or non-natural backbone linkages, e.g. phosphorothioates, PNA or 2'-O-methyl-RNA, or combinations thereof.

As used herein, the term "primer" is defined as a nucleic acid having a single strand with a free 3' OH group. A primer can also have a modification at the 5' terminus to allow a coupling reaction or to couple the primer to another moiety. The primer length can be any number of bases long and can include a variety of non-natural nucleotides. As used herein, "BCN primer" or "BCN modified primer" refers to a primer comprising covalently attached bicyclo[6.1.0] non-4-yne at the 5' terminus.

As used herein, the term "silane" refers to an organic or inorganic compound containing one or more silicon atoms. Non-limiting example of an inorganic silane compound is $SiH_4$, or halogenated $SiH_4$ where hydrogen is replaced by one or more halogen atoms. Non-limiting example of an organic silane compound is $X-R^C-Si(OR^D)_3$, wherein X is a non-hydrolyzable organic group, such as amino, vinyl, epoxy, methacrylate, sulfur, alkyl, alkenyl, alkynyl; $R^C$ is a spacer, for example $-(CH_2)_n-$, wherein n is 0 to 1000; $R^D$ is selected from hydrogen, optionally substituted alkyl, optionally substituted alkenyl, optionally substituted alkynyl, optionally substituted carbocyclyl, optionally substituted aryl, optionally substituted 5-10 membered heteroaryl, and optionally substituted 5-10 membered heterocyclyl, as defined herein. As used herein, the term "silane" can comprise mixtures of different silane compounds.

As used herein, the term "polymer" refers to a molecule composed of many repeated subunits or recurring units. Non-limiting examples of polymer structures include linear, branched, or hyper-branched polymers. Non-limiting examples of linear polymers comprising block copolymers or random copolymers. Non-limiting examples of branched polymers include star polymers, star-shaped or star-block polymers comprising both hydrophobic and hydrophilic segments, H-shaped polymers comprising both hydrophobic and hydrophilic segments, dumbbell shaped polymers, comb polymers, brush polymers, dendronized polymers, ladders, and dendrimers. The polymers described herein can also be in the form of polymer nanoparticles. Other examples of polymer architectures include, but not limited to ring block polymers, coil-cycle-coil polymers, etc.

As used herein, the prefixes "photo" or "photo-" mean relating to light or electromagnetic radiation. The term can encompass all or part of the electromagnetic spectrum including, but not limited to, one or more of the ranges commonly known as the radio, microwave, infrared, visible, ultraviolet, X-ray or gamma ray parts of the spectrum. The part of the spectrum can be one that is blocked by a metal region of a surface such as those metals set forth herein. Alternatively or additionally, the part of the spectrum can be one that passes through an interstitial region of a surface such as a region made of glass, plastic, silica, or other material set forth herein. In particular embodiments, radiation can be used that is capable of passing through a metal. Alternatively or additionally, radiation can be used that is masked by glass, plastic, silica, or other material set forth herein.

As used herein, the term "YES method" refers to the chemical vapor deposition tool provided by Yield Engineering Systems ("YES") with chemical vapor deposition process developed by Illumina, Inc. It includes three different vapor deposition systems. The automated YES-VertaCoat silane vapor system is designed for volume production with a flexible wafer handling module that can accommodate 200 or 300 mm wafers. The manual load YES-1224P Silane Vapor System is designed for versatile volume production with its configurable large capacity chambers. Yes-LabKote is a low-cost, tabletop version that is ideal for feasibility studies and for R&D.

As used herein, the term "percent surface remaining" can refer to the intensity measured using a TET QC to stain the P5/P7 surface primers. The P5 and P7 primers are used on the surface of commercial flow cells sold by Illumina Inc. for sequencing on the HiSeq®, MiSeq®, Genome Analyzer® and NextSeq® platforms. The primer sequences are described in U.S. Pat. Pub. No. 2011/0059865 A1, which is incorporated herein by reference. The P5 and P7 primer sequences comprise the following:

```
Paired end set:
P5: paired end 5' → 3'
                              SEQ ID NO: 1
AATGATACGGCGACCACCGAGAUCTACAC P7: paired end 5' → 3'
                              SEQ ID NO: 2
CAAGCAGAAGACGGCATACGAG*AT
```

```
-continued
Single read set:
P5: single read: 5' → 3'
                                       SEQ ID NO: 3
AATGATACGGCGACCACCGA P7: single read 5' → 3'
                                       SEQ ID NO: 4
CAAGCAGAAGACGGCATACGA
```

In some embodiments, the P5 and P7 primers may comprise a linker or spacer at the 5' end. Such linker or spacer may be included in order to permit cleavage, or to confer some other desirable property, for example to enable covalent attachment to a polymer or a solid support, or to act as spacers to position the site of cleavage an optimal distance from the solid support. In certain cases, 10 spacer nucleotides may be positioned between the point of attachment of the P5 or P7 primers to a polymer or a solid support. In some embodiments polyT spacers are used, although other nucleotides and combinations thereof can also be used. In one embodiment, the spacer is a 10T spacer. TET is a dye labeled oligonucleotide having complimentary sequence to the P5/P7 primers. TET can be hybridized to the P5/P7 primers on a surface; the excess TET can be washed away, and the attached dye concentration can be measured by fluorescence detection using a scanning instrument such as a Typhoon Scanner (General Electric).

Polymers and DNA-Copolymers

Polymers and Nucleic Acid-Copolymers with Recurring Units of Formulae (I) and (II)

Some embodiments described herein are related to a polymer for surface functionalization, comprising a recurring unit of Formula (I) and a recurring unit of Formula (II) as described above.

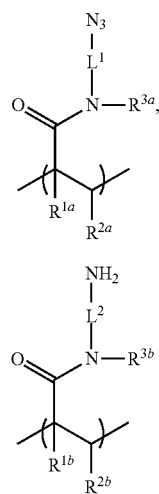

wherein each $R^{1a}$, $R^{2a}$, $R^{1b}$ and $R^{2b}$ is independently selected from hydrogen, optionally substituted alkyl or optionally substituted phenyl; each $R^{3a}$ and $R^{3b}$ is independently selected from hydrogen, optionally substituted alkyl, optionally substituted phenyl, or optionally substituted $C_{7-14}$ aralkyl; and each $L^1$ and $L^2$ is independently selected from an optionally substituted alkylene linker or an optionally substituted heteroalkylene linker.

In some embodiments, $R^{1a}$ is hydrogen. In some embodiments, $R^{2a}$ is hydrogen. In some embodiments, $R^{3a}$ is hydrogen. In some embodiments, $R^{1a}$ is selected from hydrogen or optionally substituted alkyl, preferably $C_{1-6}$ alkyl and each of $R^{2a}$ and $R^{3a}$ is hydrogen. In some embodiments, each of $R^{1a}$, $R^{2a}$ and $R^{3a}$ is hydrogen. In some embodiments, $R^{1b}$ is hydrogen. In some embodiments, $R^{2b}$ is hydrogen. In some embodiments, $R^{3b}$ is hydrogen. In some embodiments, $R^{1b}$ is selected from hydrogen or optionally substituted alkyl, preferably $C_{1-6}$ alkyl and each of $R^{2b}$ and $R^{3b}$ is hydrogen. In some embodiments, each of $R^{1b}$, $R^{2b}$ and $R^{3b}$ is hydrogen. In some embodiments, $L^1$ is an optionally substituted alkylene. In some such embodiments, $L^1$ is optionally substituted methylene. In some other embodiments, $L^1$ is optionally substituted ethylene. In some further embodiments, $L^1$ is optionally substituted propylene. In some embodiments, $L^1$ is an optionally substituted heteroalkylene linker. In some such embodiments, $L^1$ is —(CH$_2$)m-NH—(CH$_2$)$_n$-optionally substituted with one or more oxo groups, and wherein each m and n is an integer independently selected from 1 to 10. In some embodiments, $L^2$ is an optionally substituted alkylene. In some such embodiments, $L^2$ is optionally substituted methylene. In some other embodiments, $L^2$ is optionally substituted ethylene. In some further embodiments, $L^2$ is optionally substituted propylene. In some embodiments, the recurring unit of Formula (I) is also represented by Formula (Ia) or (Ib) and Formula (II) is also represented by Formula (IIa):

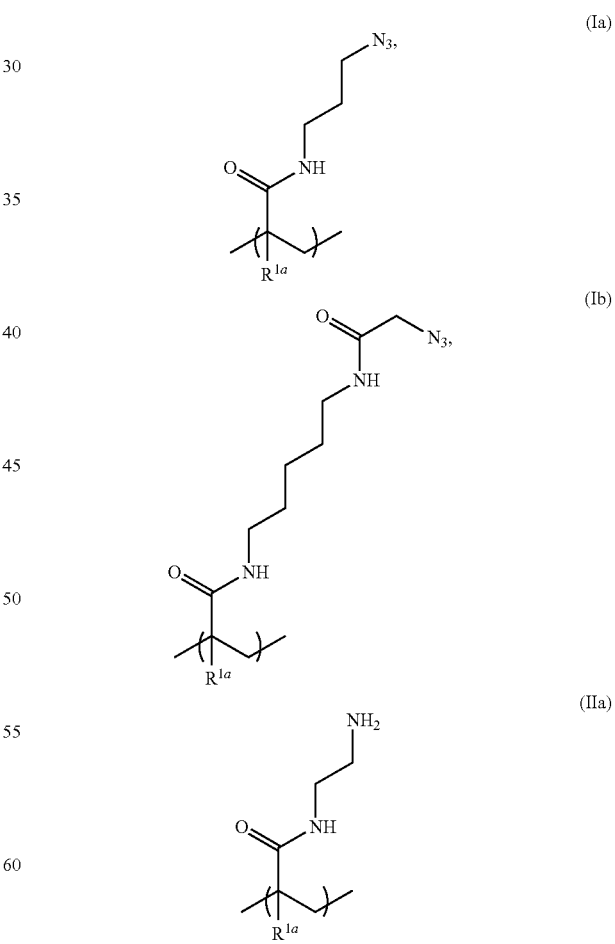

wherein each $R^{1a}$ and $R^{1b}$ is selected from hydrogen or methyl. In some embodiments, the polymer comprises recurring units of Formula (Ia) and (IIa). In some other embodiments, the polymer comprises recurring units of Formula (Ib) and (IIa). In some embodiments of the recurring unit of Formula (II) or (IIa), the amino functional group is in the form of an inorganic salt, for example, hydrochloride salt. In some embodiments, the recurring units of Formulae (I) and (II) are about 1:1 in molar ratio. In some such embodiments, the recurring units of Formulae (Ia) and (IIa) are about 1:1 in molar ratio. In some such embodiments, the recurring units of Formulae (Ib) and (IIa) are about 1:1 in molar ratio.

In some embodiments, the polymer may further comprise one or more recurring units selected from the group consisting of polyacrylamides, polyacrylates, polyurethanes, polysiloxanes, silicones, polyacroleins, polyphosphazenes, polyisocyanates, poly-ols, and polysaccharides, or combinations thereof. In some such embodiments, the polymer may further comprising one or more recurring units of polyacrylamide of Formula (IIIa) or (IIIb) or both:

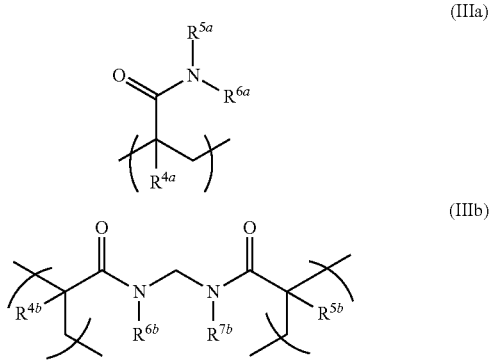

wherein each $R^{4a}$, $R^{4b}$ and $R^{5b}$ is selected from hydrogen or $C_{1-3}$ alkyl; and each $R^{5a}$, $R^{6a}$, $R^{6b}$ and $R^{7b}$ is independently selected from hydrogen, optionally substituted $C_{1-6}$ alkyl or optionally substituted phenyl. In some embodiments, each $R^{4a}$, $R^{4b}$ and $R^{5b}$ is selected from hydrogen or methyl. In some embodiments, $R^{6b}$ and $R^{7b}$ are both hydrogen. In some embodiments, at least one of $R^{5a}$ or $R^{6a}$ is hydrogen. In some such embodiments, both $R^{5a}$ and $R^{6a}$ are hydrogen. In some other embodiments, at least one of $R^{5a}$ or $R^{6a}$ is methyl. In some such embodiments, both $R^{5a}$ and $R^{6a}$ are methyl. In some such embodiments, the recurring units of Formula (IIIa) is also represented by (IIIa1), (IIIa2) or (IIIa3):

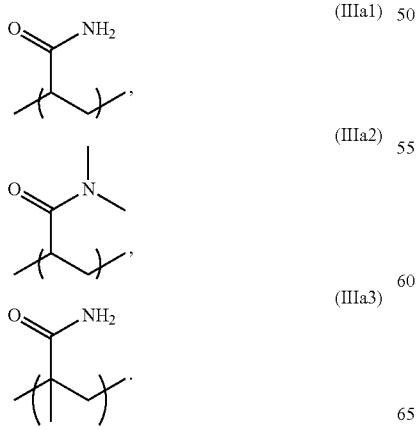

In some such embodiments, the recurring unit of Formula (IIIb) is also represented by (IIIb1):

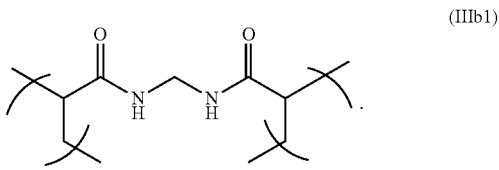

In some specific embodiments, the polymer comprises recurring units of Formulae (Ib), (IIa) and (IIIa). In some further embodiments, the polymer comprises recurring units of Formulae (Ib), (IIa), (IIIa) and (IIIb). In some such embodiments, the mole percent of Formula (IIIa) is from about 85% to about 90%. In some such embodiments, the mole percent of Formulae (Ib) and (IIa) is about 5% each. In one embodiment, the polymer comprises recurring units of Formulae (IIIa1), (Ib) and (IIa) in the mole percent of about 90% to about 5% to about 5%. In another embodiment, the polymer comprises recurring units of Formulae (IIIa1), (Ib) and (IIa) in the molar percent ratio of about 85% to about 5% to about 10%. In yet another embodiment, the polymer comprises recurring units of Formulae (IIIa2), (Ib) and (IIa) in the molar percent ratio of about 90% to about 5% to about 5%. In some further embodiments, the polymer may further comprise about 0.5 mol % to about 2 mol % of a recurring unit of Formula (IIIb1).

Some embodiments described herein are related to a grafted polymer comprising functionalized oligonucleotides covalently bonded to a polymer with a recurring unit of Formula (I) and a recurring unit of Formula (II) as described herein. In some embodiments, the polymer may further comprise one or more recurring units of various different polymer backbones as described above, for example, one or more recurring units of polyacrylamide of Formula (IIIa) or (IIIb) or both. In some embodiments, the covalent bonding between the functionalized oligonucleotide and the polymer comprises the structure moiety

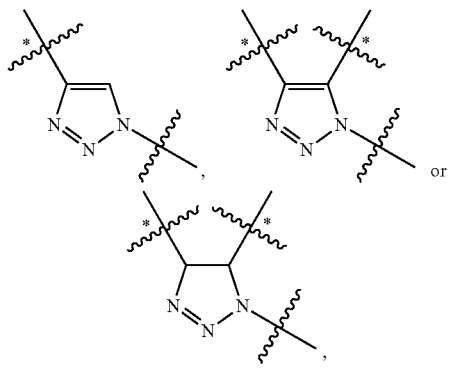

or combinations thereof, wherein * indicates the point of connection with the functionalized oligonucleotide. In some such embodiments, the covalent bonding between the functionalized oligonucleotide and the polymer comprises structure moiety

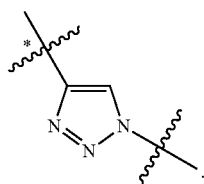 [SMILES: *c1cn(*)nn1]

In some other such embodiments, the covalent bonding between the functionalized oligonucleotide and the polymer comprises structure moiety

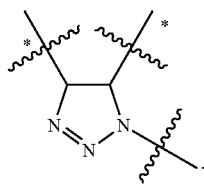 [SMILES: *C1N=NN(*)C1*]

In some such embodiments, the covalent bonding between the functionalized oligonucleotide and the polymer comprises structure moiety

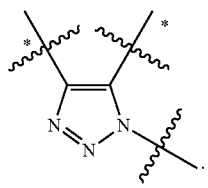 [SMILES: *c1nnn(*)c1*]

In some embodiments, the grafted polymer is prepared by reacting one or more functional moieties of the functionalized oligonucleotide with the polymer, said one or more functional moieties comprise or are selected from alkynes, cycloalkenes, cycloalkynes, heterocycloalkenes, heterocycloalkynes, or optionally substituted variants or combinations thereof. In some such embodiments, said one or more functional moieties comprise alkyne or are selected from alkyne. In some other embodiments, said one or more functional moieties comprise or are selected from norbornene, cyclooctyne, or bicyclononyne, or optionally substituted variants or combinations thereof. In one embodiment, the bicyclononyne is bicyclo[6.1.0]non-4-yne. In some such embodiments, the grafted polymer is prepared by reacting the azido groups of the polymer with said one or more functional moieties of the functionalized oligonucleotides, for example, bicyclo[6.1.0]non-4-yne.

Polymers and Nucleic Acid-Copolymers with Recurring Units of Formula (IV)

Some embodiments described herein are related to a polymer for surface functionalization, comprising a recurring unit of Formula (IV) as described above:

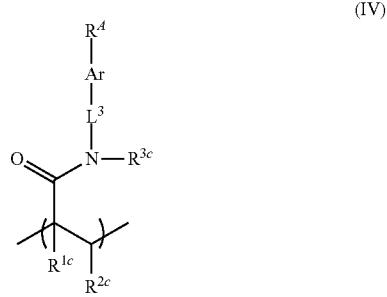

wherein each $R^{1c}$ and $R^{2c}$ is independently selected from hydrogen, optionally substituted alkyl or optionally substituted phenyl; $R^{3c}$ is selected from hydrogen, optionally substituted alkyl, optionally substituted phenyl, or optionally substituted $C_{7-14}$ aralkyl; Ar is selected from an optionally substituted $C_{6-10}$ aryl or an optionally substituted 5 or 6 membered heteroaryl; $R^4$ is optionally substituted tetrazine; and $L^3$ is selected from a single bond, an optionally substituted alkylene linker or an optionally substituted heteroalkylene linker.

In some embodiments, $R^{1c}$ is hydrogen. In some embodiments, $R^{2c}$ is hydrogen. In some embodiments, $R^{3c}$ is hydrogen. In some embodiments, $R^{1c}$ is selected from hydrogen or optionally substituted alkyl, preferably $C_{1-6}$ alkyl and each $R^{2c}$ and $R^{3c}$ is hydrogen. In some embodiments, each $R^{1c}$, $R^{2c}$ and $R^{3c}$ is hydrogen. In some embodiments, Ar is an optionally substituted phenyl. In some embodiments, $L^3$ is a single bond. In some embodiments, the recurring unit of Formula (IV) is also represented by Formula (IVa):

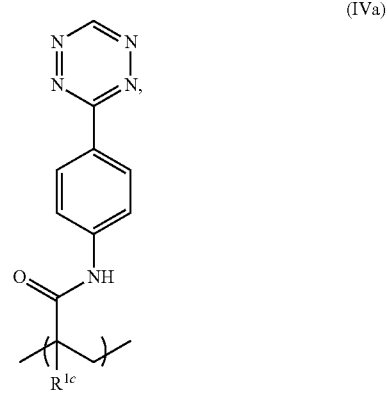

wherein $R^{1c}$ is selected from hydrogen or methyl.

In some embodiments, the polymer may further comprise one or more recurring units selected from the group consisting of polyacrylamides, polyacrylates, polyurethanes, polysiloxanes, silicones, polyacroleins, polyphosphazenes, polyisocyanates, poly-ols, and polysaccharides, or combinations thereof. In some such embodiments, the polymer may further comprising one or more recurring units of polyacrylamide of Formula (IIIa) or (IIIb) with the structure shown above.

Some embodiments described herein are related to a grafted polymer comprising functionalized oligonucleotides covalently bonded to a polymer with a recurring unit of Formula (IV) as described herein. In some embodiments, the polymer may further comprise one or more recurring units of various different polymer backbones as described above, for example, one or more recurring units of polyacrylamide of Formula (IIIa) or (IIIb) or both. In some embodiments, the covalent bonding between the functionalized oligonucleotide and the polymer comprises the structure moiety

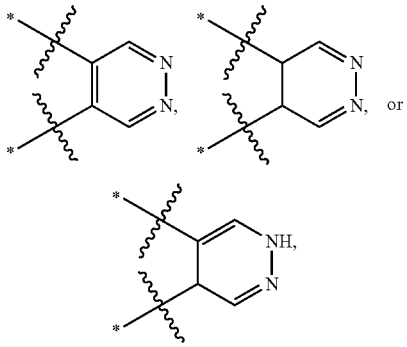

or combinations thereof, and wherein * indicates the point of connection of the polymer with the functionalized oligonucleotide. In some such embodiments, the covalent bonding between the functionalized oligonucleotide and the polymer comprises structure moiety

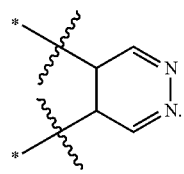 [SMILES: *C1C=NN=CC1*]

In some other such embodiments, the covalent bonding between the functionalized oligonucleotide and the polymer comprises structure moiety

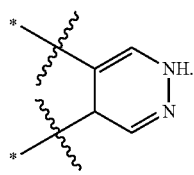 [SMILES: *C1=CNN=CC1*]

In some embodiments, the grafted polymer is prepared by reacting one or more functional moieties of the functionalized oligonucleotide with the polymer, said one or more functional moieties comprise, or are selected from, alkynes, cycloalkenes, cycloalkynes, heterocycloalkenes, heterocycloalkynes, or optionally substituted variants or combinations thereof. In some such embodiments, the one or more functional moieties may include or be selected from norbornene, cyclooctyne, or bicyclononyne, or optionally substituted variants or combinations thereof. In one embodiment, the bicyclononyne is bicyclo[6.1.0]non-4-yne. In some such embodiments, the grafted polymer is prepared by reacting the tetrazine groups of the polymer with said one or more functional moieties of the functionalized oligonucleotides, for example, bicyclo[6.1.0]non-4-yne.

Polymers and Nucleic Acid-Copolymers with Recurring Units of Formula (V)

Some embodiments described herein are related to a polymer for surface functionalization, comprising a recurring unit of Formula (V) as described above:

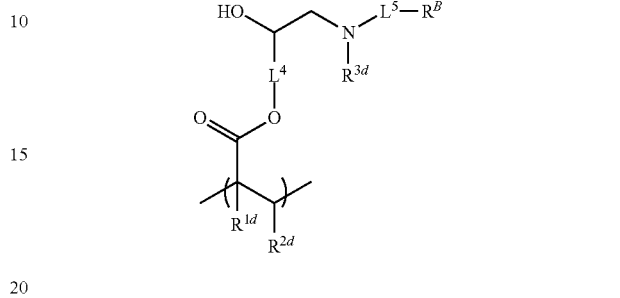

wherein each $R^{1d}$ and $R^{2d}$ is independently selected from hydrogen, optionally substituted alkyl or optionally substituted phenyl; each $R^{3d}$ is selected from hydrogen, optionally substituted alkyl, optionally substituted phenyl, or optionally substituted $C_{7-14}$ aralkyl; $R^B$ is selected from azido, optionally substituted amino, Boc-protected amino, hydroxy, thiol, alkynyl, alkenyl, halo, epoxy, tetrazine or aldehyde; each $L^4$ and $L^5$ is independently selected from an optionally substituted alkylene linker or an optionally substituted heteroalkylene linker.

In some embodiments, $R^{1d}$ is alkyl group, preferably $C_{1-6}$ alkyl. In some such embodiments, $R^{1d}$ is methyl. In some other embodiments, $R^{1d}$ is hydrogen. In some embodiments, e$R^{2d}$ is hydrogen. In some embodiments, $R^{3d}$ is hydrogen. In some embodiments, each $R^{2d}$ and $R^{3d}$ is hydrogen. In some embodiments, $R^B$ is selected from azido, amino or Boc-protected amino, or combinations thereof. In some embodiments, $L^4$ is an optionally substituted alkylene linker. In some such embodiments, $L^4$ is a methylene linker. In some embodiments $L^5$ is an optionally substituted heteroalkylene linker. In some such embodiments, $L^5$ is

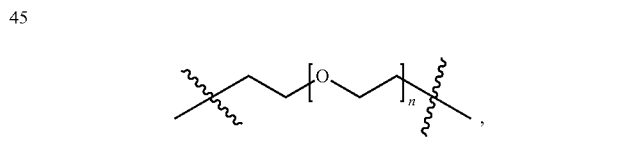

and wherein n is an integer of 1 to 50. In some embodiments, the recurring unit of Formula (V) is also represented by Formula (Va) or (Vb):

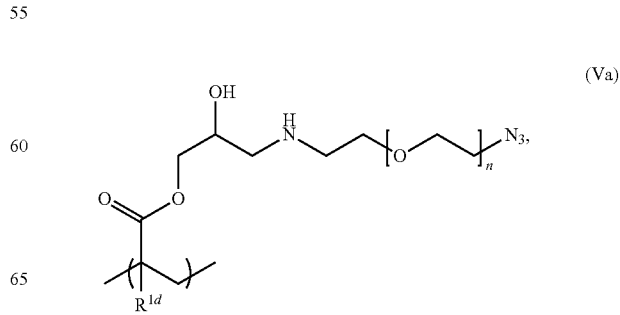

(Vb)

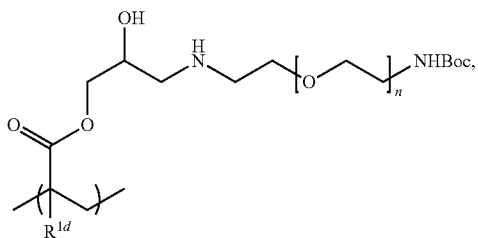

wherein each $R^{1d}$ is independently selected from hydrogen or methyl. In some such embodiments, n is an integer of 1 to 20. In some such embodiments, n is an integer of 1 to 10. In some such embodiments, n is an integer of 1 to 5. In one embodiment, n is 3. In some embodiments, the polymer comprises both Formulae (Va) and (Vb).

In some embodiments, the polymer may further comprise a recurring unit of Formula (VIa) or (VIb), or both:

(VIa)

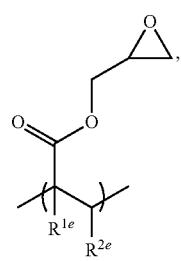

(VIb)

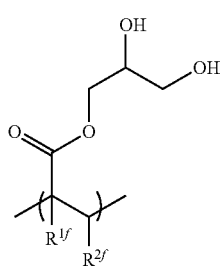

wherein each $R^{1e}$, $R^{2e}$, $R^{1f}$ and $R^{2f}$ is independently selected from hydrogen, optionally substituted alkyl or optionally substituted phenyl. In some such embodiments, $R^{1e}$ is alkyl, preferably $C_{1-6}$ alkyl, for example, methyl. In some other embodiments, $R^{1e}$ is hydrogen. In some embodiments, $R^{2e}$ is hydrogen. In some such embodiments, $R^{1f}$ is alkyl, preferably $C_{1-6}$ alkyl, for example, methyl. In some other embodiments, $R^{1f}$ is hydrogen. In some embodiments, $R^{2f}$ is hydrogen.

In some embodiments, the polymer may further comprise one or more recurring units selected from the group consisting of polyacrylamides, polyacrylates, polyurethanes, polysiloxanes, silicones, polyacroleins, polyphosphazenes, polyisocyanates, poly-ols, and polysaccharides, or combinations thereof. In some such embodiments, the polymer may further comprising one or more recurring units of polyacrylamide of Formula (IIIa) or (IIIb) with the structure shown above.

Some embodiments described herein are related to a grafted polymer comprising functionalized oligonucleotides covalently bonded to a polymer with a recurring unit of Formula (V) as described herein. In some embodiments, the polymer may further comprise a recurring unit of Formula (VIa) or (VIb), or both. In some embodiments, the covalent bonding between the functionalized oligonucleotide and the polymer comprises the structure moiety

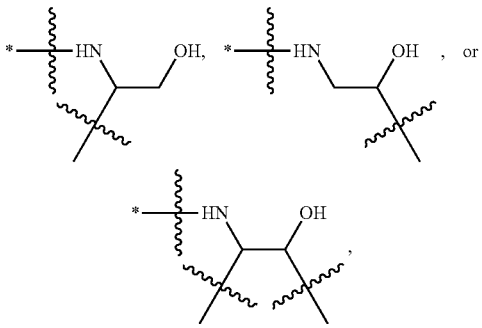

or combinations thereof, wherein * indicates the polymer's point of connection with the functionalized oligonucleotide. In some such embodiments, the covalent bonding between the functionalized oligonucleotide and the polymer comprises structure moiety

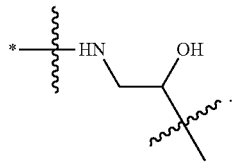

In some embodiments, the grafted polymer is prepared by reacting one or more functional moieties of the functionalized oligonucleotide with the polymer, said one or more functional moieties comprise or are selected from optionally substituted amino, hydroxy, thiol, carboxyl, acid anhydride, or combinations thereof. In one embodiment, the functionalized oligonucleotide comprises one or more optionally substituted amino groups. In some such embodiments, the amino group is unsubstituted. In some such embodiments, the grafted polymer is prepared by reacting the glycidyl ether or epoxy groups of the polymer with said one or more amino groups of the functionalized oligonucleotides. In some such embodiments, the epoxy groups of the polymer are derived from recurring unit of Formula (VIa).

Substrates

Some embodiments described herein are related to a substrate having a first surface comprising a polymer with a recurring unit of Formula (I) and a recurring unit of Formula (II) covalently bonded thereto as described herein. In some embodiments, the polymer may further comprise one or more recurring units selected from the group consisting of polyacrylamides, polyacrylates, polyurethanes, polysiloxanes, silicones, polyacroleins, polyphosphazenes, polyisocyanates, poly-ols, and polysaccharides, or combinations thereof. In some such embodiments, the polymer may further comprising one or more recurring units of polyacrylamide of Formula (IIIa) or (IIIb) with the structure shown above. In some embodiments, the covalent bonds between the polymer and the substrate are formed by amine epoxy ring opening reaction. In some embodiments, the covalent bonding between the polymer and the first surface of the substrate comprises the structure moiety

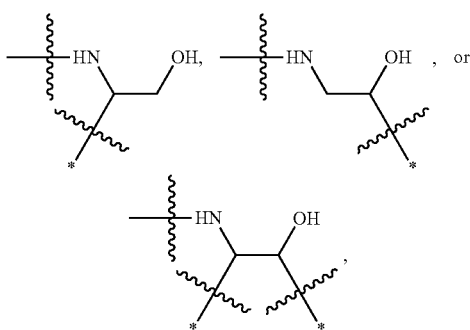

or combinations thereof, wherein the substituted amino is derived from the recurring unit of Formula (II) and * indicates the polymer's point of connection with the first surface of the substrate. In some such embodiment, the covalent bonding between the polymer and the first surface comprises structure moiety

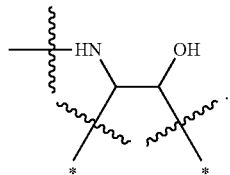

In some embodiments, the substrate is prepared by reacting the polymer with a first plurality of functional groups covalently attached thereto the first surface, wherein the first plurality of functional groups comprise or are selected from vinyl, acryloyl, alkenyl, cycloalkenyl, heterocycloalkenyl, alkynyl, cycloalkynyl, heterocycloalkynyl, nitrene, aldehyde, hydrazinyl, glycidyl ether, epoxy, carbene, isocyanate or maleimide, or optionally substituted variants or combinations thereof. In some such embodiments, the first plurality of functional groups comprises or are selected from epoxy groups. In one embodiment, said epoxy group has the structure

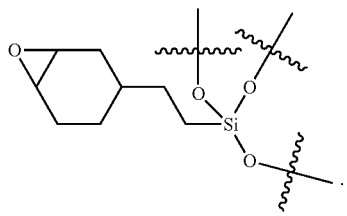 [SMILES: *O[Si](CCC1CCC2OC2C1)(O*)O*]

In some embodiments, the substrate is prepared by reacting the amino groups of the polymer with the epoxy groups of the first surface. In some embodiments, the surface is pretreated with a functionalized silane comprising said first plurality of the functional groups described above, and the polymer is covalently bonded to the first surface through reaction with the first plurality of the functional groups of the functionalized silane.

In some embodiments, the substrate further comprises functionalized oligonucleotides covalently bonded to the polymer. In some embodiment, the covalent bond between the oligonucleotide and the polymer is formed by azide click cycloaddition reaction. In some embodiments, the covalent bonding between the functionalized oligonucleotide and the polymer comprises the structure moiety

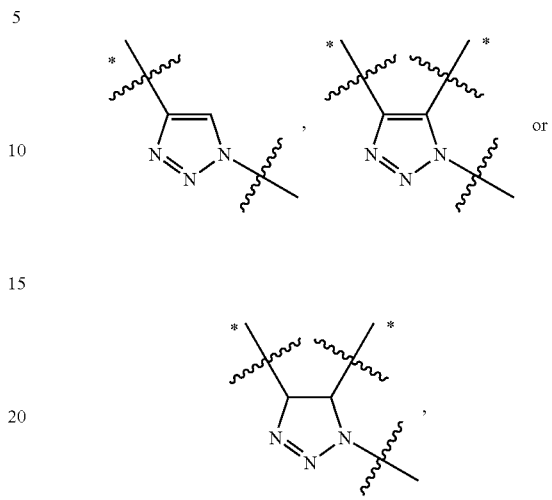

or combinations thereof, wherein * indicates the polymer's point of connection with the functionalized oligonucleotide. In some such embodiments, the functionalized oligonucleotides are covalently bonded to the polymer by reacting one or more functional moieties of the functionalized oligonucleotides with the azido groups of the polymer, said one or more functional moieties comprise or are selected from alkynes, cycloalkenes, cycloalkynes, heterocycloalkenes, heterocycloalkynes, or optionally substituted variants or combinations thereof. In some such embodiments, said one or more functional moieties comprise alkyne. In some other embodiments, said one or more functional moieties comprise or are selected from norbornene, cyclooctyne, or bicyclononyne, or optionally substituted variants or combinations thereof. In one embodiment, the bicyclononyne is bicyclo[6.1.0]non-4-yne. In some embodiments, the functionalized oligonucleotides are covalently bonded to the polymer by reacting the azido groups of the polymer with one or more alkyne moieties of the functionalized oligonucleotides. In some other embodiments, the functionalized oligonucleotides are covalently bonded to the polymer by reacting the azido groups of the polymer with one or more bicyclo[6.1.0]non-4-yne moieties of the functionalized oligonucleotides.

Some embodiments described herein are related to a substrate having a first surface comprising a polymer with a recurring unit of Formula (IV) covalently bonded thereto as described herein. In some embodiments, the polymer may further comprise one or more recurring units selected from the group consisting of polyacrylamides, polyacrylates, polyurethanes, polysiloxanes, silicones, polyacroleins, polyphosphazenes, polyisocyanates, poly-ols, and polysaccharides, or combinations thereof. In some such embodiments, the polymer may further comprising one or more recurring units of polyacrylamide of Formula (IIIa) or (IIIb) with the structure shown above. In some embodiments, the covalent bonds between the polymer and the substrate are formed by tetrazine Diels-Alder reactions, which results in the elimination of nitrogen gas. In some embodiments, wherein the covalent bonding between the polymer and the first surface of the substrate comprises the structure moiety

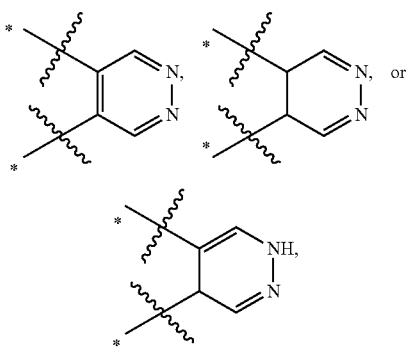

or combinations thereof, wherein * indicates the polymer's point of connection with the first surface. In some such embodiments, the covalent bonding between the polymer and the first surface comprises structure moiety

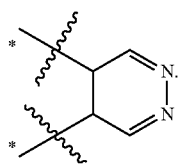 [SMILES: *C1C=NN=CC1*]

In some other such embodiments, the covalent bonding between the polymer and the first surface comprises structure moiety

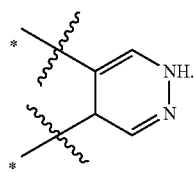 [SMILES: *C1=CNN=CC1*]

In some embodiments, the substrate is prepared by reacting the polymer with a first plurality of functional groups covalently attached thereto the first surface, wherein the first plurality of functional groups comprise or are selected from vinyl, acryloyl, alkenyl, cycloalkenyl, heterocycloalkenyl, alkynyl, cycloalkynyl, heterocycloalkynyl, nitrene, aldehyde, hydrazinyl, glycidyl ether, epoxy, carbene, isocyanate or maleimide, or optionally substituted variants or combinations thereof. In some such embodiments, the first plurality of functional groups comprises, or are selected from, optionally substituted cycloalkenyl groups. In one embodiment, said cycloalkenyl is norbornene. In some embodiments, the substrate is prepared by reacting the tetrazine groups of the polymer with the norbornene groups of the first surface. In some embodiments, the surface is pretreated with a functionalized silane comprising said first plurality of the functional groups described above, and the polymer is covalently bonded to the first surface through reaction with the first plurality of the functional groups of the functionalized silane.

In some embodiments, the substrate further comprises functionalized oligonucleotides covalently bonded to the polymer. In some embodiments, the covalent bonding between the oligonucleotide and the polymer is formed by a tetrazine Diels-Alder reaction, which results in the elimination of nitrogen gas. In some embodiments, the covalent bonding between the functionalized oligonucleotide and the polymer comprises the structure moiety

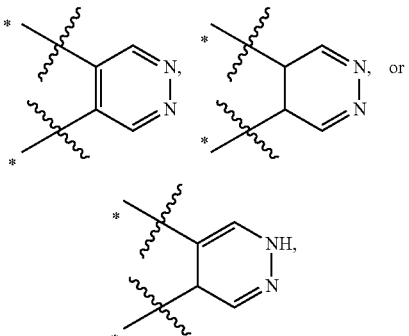

or combinations thereof, and wherein * indicates the polymer's point of connection with the functionalized oligonucleotide. In some such embodiments, the covalent bonding between the functionalized oligonucleotide and the polymer comprises structure moiety

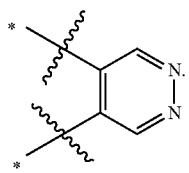

In some such embodiments, the functionalized oligonucleotides are covalently bonded to the polymer by reacting one or more functional moieties of the functionalized oligonucleotides with the tetrazine groups of the polymer, said one or more functional moieties comprise or are selected from alkynes, cycloalkenes, cycloalkynes, heterocycloalkenes, heterocycloalkynes, or optionally substituted variants or combinations thereof. In some such embodiments, said one or more functional moieties comprise or are selected from norbornene, cyclooctyne, or bicyclononyne, or optionally substituted variants or combinations thereof. In one embodiment, the bicyclononyne is bicyclo[6.1.0]non-4-yne. In some such embodiments, the functionalized oligonucleotides are covalently bonded to the polymer by reacting the tetrazine groups of the polymer with one or more bicyclo[6.1.0]non-4-yne moieties of the functionalized oligonucleotides.

Some embodiments described herein are related to a substrate having a first surface comprising a polymer with a recurring unit of Formula (V) covalently bonded thereto as described herein. In some embodiments, the polymer may further comprise one or more recurring units selected from the group consisting of polyacrylamides, polyacrylates, polyurethanes, polysiloxanes, silicones, polyacroleins, polyphosphazenes, polyisocyanates, poly-ols, and polysaccharides, or combinations thereof. In some embodiments, the polymer may further comprise a recurring unit of Formula (VIa) or (VIb), or both. In some embodiments, the covalent bonds between the polymer and the substrate are formed by amine epoxy ring opening reaction. In some other embodiments, the covalent bonds between the polymer and the substrate are formed by azide click cycloaddition reaction. In some embodiments, the covalent bonding between the polymer and the first surface of the substrate comprises the structure moiety

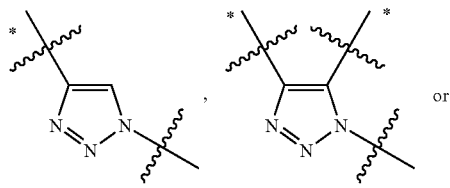

or combinations thereof, wherein * indicates the point of connection of polymer with the first surface. In some such embodiments, the covalent bonding between the polymer and the first surface comprises structure moiety

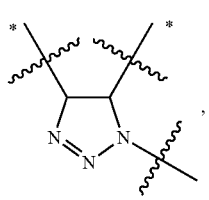

In some other embodiments, the covalent bonding between the polymer and the first surface comprises the structure moiety

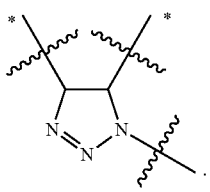 [SMILES: *C1N=NN(*)C1*]

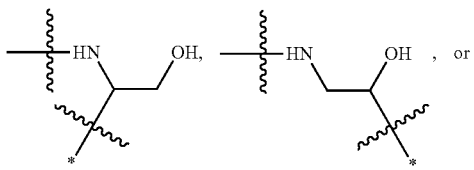

or combinations thereof, wherein * indicates the point of connection of polymer with the first surface. In some such embodiments, the covalent bonding between the polymer and the first surface comprises structure moiety

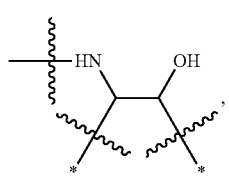

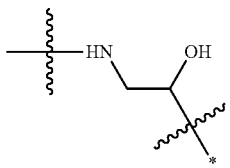

In some other such embodiments, the covalent bonding between the polymer and the first surface comprises structure moiety

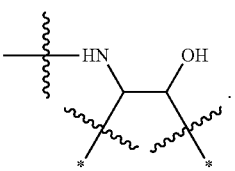

In some embodiments, the substrate is prepared by reacting the polymer with a first plurality of functional groups covalently attached thereto the first surface, wherein the first plurality of functional groups comprise or are selected from vinyl, acryloyl, alkenyl, cycloalkenyl, heterocycloalkenyl, alkynyl, cycloalkynyl, heterocycloalkynyl, nitrene, aldehyde, hydrazinyl, glycidyl ether, epoxy, carbene, isocyanate or maleimide, or optionally substituted variants or combinations thereof. In some such embodiments, the first plurality of functional groups comprises or are selected from optionally substituted cycloalkenyl groups. In one embodiment, said cycloalkenyl is norbornene. In some embodiments, the substrate is prepared by reacting the azido groups of the polymer with the norbornene groups of the first surface. In some other embodiments, the first plurality of functional groups comprises or are selected from glycidyl ether or epoxy groups. In some embodiments, the substrate is prepared by deprotecting the Boc-protected amino of the polymer and then reacting the amino groups of the polymer with the glycidyl ether or epoxy groups of the first surface. In some embodiments, the surface is pretreated with a functionalized silane comprising said first plurality of the functional groups described above, and the polymer is covalently bonded to the first surface through reaction with the first plurality of the functional groups of the functionalized silane.

In some embodiments, the substrate further comprises functionalized oligonucleotides covalently bonded to the polymer. In some embodiments, the covalent bonding between the oligonucleotide and the polymer is formed by amine epoxy ring opening reaction. In some embodiments, the covalent bonding between the functionalized oligonucleotide and the polymer comprises the structure moiety

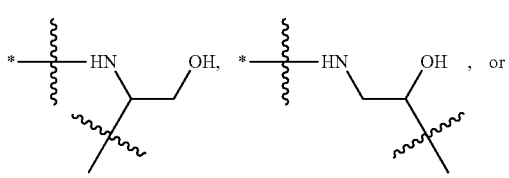

-continued

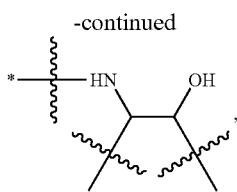

or combinations thereof, wherein * indicates the point of connection of polymer with the functionalized oligonucleotide. In some embodiments, the covalent bonding between the functionalized oligonucleotide and the polymer comprises structure moiety

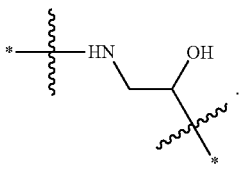

In some such embodiments, the functionalized oligonucleotides are covalently bonded to the polymer by reacting one or more functional moieties of the functionalized oligonucleotides with the epoxy groups of the polymer, said one or more functional moieties comprise or are selected from optionally substituted amino, hydroxy, thiol, carboxyl, acid anhydride, or combinations thereof. In some such embodiments, said one or more functional moieties comprise or are selected from optionally substituted amino groups. In some such embodiments, the functionalized oligonucleotides are covalently bonded to the polymer by reacting the epoxy groups of the polymer with the amino groups of the functionalized oligonucleotides.

In embodiments described herein, the substrate material may comprise glass, silica, plastic, quartz, metal, metal oxide, or combinations thereof. In some embodiments, the substrate comprises glass. In some embodiments, the first surface of the substrate comprises both polymer coated regions and inert regions.

Substrate Surface Preparations

Some embodiments described herein are related to processes or methods for immobilizing a grafted polymer to a first surface of a substrate by providing a substrate having a first surface having a first plurality of functional groups covalently attached thereto; providing a grafted polymer having functionalized oligonucleotides covalently bonded to a polymer, wherein the polymer comprises a second plurality of functional groups; and reacting the first plurality functional groups of the first surface with the second plurality of functional groups of the polymer such that the polymer is covalently bonded to the first surface of the substrate.

In some embodiments of the methods described herein, the first surface of the substrate is pretreated with a functionalized silane, wherein said functionalized silane comprises the first plurality of the functional groups. In some embodiments, the functionalized silane is deposited onto the surface by Chemical Vapor Deposition (CVD) method. In some such embodiments, functionalized silane can be applied onto the first surface by CVD method using Yield Engineering Systems (YES) oven.

In some embodiments of the methods described herein, the grafted polymer is formed by reacting a third plurality of functional groups of the polymer with one or more functional moieties of the functionalized oligonucleotides. In some other embodiments, the grafted polymer is formed by reacting said one or more functional moieties of functionalized oligonucleotides with monomers comprising a third plurality of functional groups; polymerizing the reacted monomers to form the polymer such that the functionalized oligonucleotides are covalently bonded to the polymer.

In some embodiments of the methods described herein, the second plurality of functional groups of the polymer are the same as the third plurality of functional groups of the polymer. For example, the second plurality and the third plurality of functional groups of the polymer can both be tetrazines. In some other embodiments, the functional groups in the second plurality of functional groups of the polymer are different from the functional groups in the third plurality of functional groups of the polymer.

The polymer backbone used in the methods described herein can be linear, branched, hyper-branched or dendritic. The final polymer structure can be in different architectures, including, for example, random copolymer, block copolymer, comb-shaped polymer or star-shaped polymer architectures. Different classes of polymer backbones can be used in the methods described herein, including but not limited to polyacrylamides, polyacrylates, polyurethanes, polysiloxanes, silicones, polyacroleins, polyphosphazenes, polyisocyanates, poly-ols, polysaccharides, etc. In some embodiments, the polymer comprises polyacrylamide backbone. In some other embodiments, the polymer comprises polyacrylate backbone. In still some other embodiments, the polymer comprises polyurethane backbone. In still some other embodiments, the polymer comprises polyphosphazenes backbone. In still some other embodiments, the polymer comprises a dendrimer backbone.

In some embodiments of the methods described herein, the first plurality of functional groups of the first surface comprise or are selected from vinyl, acryloyl, alkenyl, cycloalkenyl, heterocycloalkenyl, alkynyl, cycloalkynyl, heterocycloalkynyl, nitrene, aldehyde, hydrazinyl, glycidyl ether, epoxy, carbene, isocyanate or maleimide, or optionally substituted variants or combinations thereof. In some such embodiments, the first plurality of functional groups comprises or is selected from cycloalkenyl, glycidyl ether, epoxy, or optionally substituted variants or combinations thereof. In some further embodiments, the first plurality of functional groups comprises or is selected from norbornene. In some other embodiments, the first plurality of functional groups comprises an epoxy. In still some other embodiments, the first plurality of functional groups comprises glycidyl ether.

In some embodiments of the method described herein, the functional groups of the polymer may comprise or are selected from amino, tetrazinyl, azido, carboxyl, hydroxy, thiol, aldehyde, halo, alkenyl, alkynyl, epoxy, glycidyl ether, etc. In some embodiments of the methods described herein, the second plurality of functional groups of the polymer comprise or are selected from amino, tetrazinyl, azido, carboxyl, hydroxy, thiol, aldehyde, or optionally substituted variants or combinations thereof. In some such embodiments, the second plurality of functional groups comprise or are selected from amino or protected amino, for example, Boc-protected amino. In some other embodiments, the second plurality of functional groups comprises optionally substituted tetrazinyl. In still some other embodiments, the second plurality of functional groups comprises azido.

In some embodiments of the methods described herein, the third plurality of functional groups of the polymer comprises or is selected from azido, tetrazinyl, glycidyl, epoxy, alkynyl, or optionally substituted variants or combinations thereof. In some such embodiments, the third plurality of functional groups comprises azido. In some other embodiments, the third plurality of functional groups comprises optionally substituted tetrazinyl. In yet some other embodiments, the third plurality of functional groups comprises alkynyl. In yet some other embodiments, the third plurality of functional groups comprises optionally substituted glycidyl ether.

In some embodiments of the methods described herein, said one or more functional moieties of the functionalized oligonucleotides comprise or are selected from amino, azido, carboxyl, acid anhydride, tetrazine, epoxy, glycidyl ether, vinyl, acryloyl, alkenyl, cycloalkenyl, alkynyl, cycloalkynyl, nitrene, aldehyde, hydrazinyl, or maleimide or optionally substituted variants or combinations thereof. In some further embodiments, said one or more functional moieties of the functionalized oligonucleotides comprise or are selected from alkynyl, cycloalkenyl, cycloalkynyl, amino, azido, hydroxy, thiol, carboxyl, acid anhydride, or optionally substituted variants or combinations thereof. In some such embodiments, said one or more functional moieties comprise cycloalkynyl, for example, bicyclo[6.1.0]non-4-yne (BCN). In some other embodiments, said one or more functional moieties comprise alkynyl. In still some other embodiments, said one or more functional moieties comprise azido. In still some other embodiments, said one or more functional moieties comprise optionally substituted amino.

In some embodiments of the methods described herein, the grafted polymer comprises functionalized oligonucleotides covalently bonded to a polymer with a recurring unit of Formula (I) and a recurring unit of Formula (II) as described herein. In some such embodiments, the first plurality of functional groups of the first surface comprise epoxy groups. In one embodiment, said epoxy group is

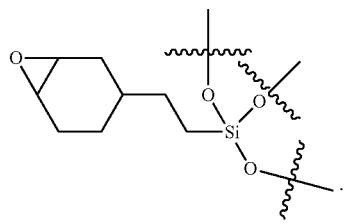

In some such embodiments, the grafted polymer is covalently bonded to the first surface by reacting the amino groups of the polymer with the epoxy groups of the first surface.

In some embodiments of the methods described herein, the grafted polymer comprises functionalized oligonucleotides covalently bonded to a polymer with a recurring unit of Formula (IV) as described herein. In some such embodiments, the first plurality of functional groups of the first surface comprises optionally substituted cycloalkenyl groups, for example, optionally substituted norbornene. In some such embodiments, the grafted polymer is covalently bonded to the first surface by reacting the tetrazine groups of the polymer with the norbornene groups of the first surface.

In some embodiments of the methods described herein, the grafted polymer comprises functionalized oligonucleotides covalently bonded to a polymer with a recurring unit of Formula (V) as described herein. In some embodiments, the polymer may further comprise a recurring unit of Formula (VIa) or (VIb), or both, as described herein. In some such embodiments, the first plurality of functional groups comprises optionally substituted cycloalkenyl groups, for example, optionally substituted norbornene. In some such embodiments, the grafted polymer is covalently bonded to the first surface by reacting the azido groups of the polymer with the norbornene groups of the first surface. In some other embodiments, the first plurality of functional groups comprises glycidyl ether or epoxy groups. In some other embodiments, the grafted polymer is covalently bonded to the first surface by deprotecting the Boc-protected amino groups of the polymer; and reacting the amino groups of the polymer with the glycidyl ether or epoxy groups of the first surface.

Some embodiments described herein are related to processes or methods for immobilizing a polymer described herein to a first surface of a substrate, comprising: providing a substrate having a first surface comprising a first plurality of functional groups covalently attached thereto; providing a polymer with recurring units of Formulae (I) and (II), Formula (IV), or Formula (V) as described herein; and reacting the first plurality functional groups of the first surface with the polymer such that the polymer is covalently bonded to the first surface of the substrate. In some such embodiments, the processes or methods further comprises providing functionalized oligonucleotides comprising one or more functionalized moieties; and reacting said one or more functionalized moieties with the polymer such that the functionalized oligonucleotides are covalently bonded to the polymer. In some such embodiments, the first plurality of functional groups of the first surface comprises or are selected from vinyl, acryloyl, alkenyl, cycloalkenyl, heterocycloalkenyl, alkynyl, cycloalkynyl, heterocycloalkynyl, nitrene, aldehyde, hydrazinyl, glycidyl ether, epoxy, carbene, isocyanate or maleimide, or optionally substituted variants or combinations thereof. In some such embodiments, said one or more functionalized moieties comprise or are selected from amino, azido, carboxyl, acid anhydride, tetrazine, epoxy, glycidyl ether, vinyl, acryloyl, alkenyl, cycloalkenyl, alkynyl, cycloalkynyl, nitrene, aldehyde, hydrazinyl, or maleimide or optionally substituted variants or combinations thereof.

In any embodiments of the methods described herein, the polymer or grafted polymer with recurring units of Formulae (I) and (II), Formula (IV), or Formula (V) may further comprise one or more recurring units selected from the group consisting of polyacrylamides, polyacrylates, polyurethanes, polysiloxanes, silicones, polyacroleins, polyphosphazenes, polyisocyanates, poly-ols, and polysaccharides, or combinations thereof. In some such embodiments, the polymer may further comprise one or more recurring units of polyacrylamide of Formula (IIIa) or (IIIb) with the structure shown above.

In any embodiments of the methods described herein, the method further comprises a washing step to remove excess unbounded functionalized oligonucleotides. In some embodiments, the method further comprises a drying step.

In any of the embodiments described herein, the substrate can comprise a material selected from glass, silica, quartz, plastic, metal, metal oxide, patterned or not or combinations thereof. In one embodiment, the surface of the substrate comprises glass. In some embodiments, the surface of the substrate can comprise both functionalized silane coated regions and inert regions. In some embodiments, the inert regions are selected from glass regions, metal regions, mask regions and interstitial regions, or combinations thereof. In one embodiment, the inert regions comprise glass.

In any of the embodiments described herein, QC markers can be included in the polymer and/or primer structures.

In any embodiments described herein, the polymer or grafted polymer may be applied to the surface of the substrate via various surface application techniques known to one skilled in the art, for example, spin coating, spray coating, dip coating, ink-jet coating, etc.

Substrates Materials and Design

In some embodiments, substrates used in the present application include silica-based substrates, such as glass, fused silica and other silica-containing materials. In some embodiments, silica-based substrates can also be silicon, silicon dioxide, silicon nitride, silicone hydrides. In some embodiments, substrates used in the present application include plastic materials such as polyethylene, polystyrene, poly(vinyl chloride), polypropylene, nylons, polyesters, polycarbonates and poly(methyl methacrylate). Preferred plastics material is poly(methyl methacrylate), polystyrene and cyclic olefin polymer substrates. In some embodiments, the substrate is a silica-based material or plastic material. In particular embodiments, the substrate has at least one surface comprising glass.

In some embodiments, the substrates can be, or can contain, a metal. In some such embodiments, the metal is gold. In some embodiments, the substrate has at least one surface comprising a metal oxide. In one embodiment, the surface comprises a tantalum oxide or tin oxide.

Acrylamide, enone, or acrylate may also be utilized as a substrate material. Other substrate materials can include, but are not limited to gallium aresnide, indium phosphide, aluminum, ceramics, polyimide, quartz, resins, polymers and copolymers. The foregoing lists are intended to be illustrative of, but not limiting to the present application.

In some embodiments, the substrate and/or the substrate surface can be quartz. In some other embodiments, the substrate and/or the substrate surface can be semiconductor, i.e. GaAs or ITO.

Substrates can comprise a single material or a plurality of different materials. Substrates can be composites or laminates. Substrate can be flat, round, textured and patterned. Patterns can be formed, for example, by metal pads that form features on non-metallic surfaces, for example, as described in U.S. Pat. No. 8,778,849, which is incorporated herein by reference. Another useful patterned surface is one having well features formed on a surface, for example, as described in U.S. Pat. App. Pub. No. 2014/0243224 A1, U.S. Pat. App. Pub. No. 2011/0172118 A1 or U.S. Pat. No. 7,622,294, each of which is incorporated herein by reference in its entirety. For embodiments that use a patterned substrate, a gel can be selectively attached to the pattern features (e.g. gel can be attached to metal pads or gel can be attached to the interior of wells) or alternatively the gel can be uniformly attached across both the pattern features and the interstitial regions.

Advantages in using plastics-based substrates in the preparation and use of molecular arrays include cost: the preparation of appropriate plastics-based substrates by, for example injection-molding, is generally cheaper than the preparation, e.g. by etching and bonding, of silica-based substrates. Another advantage is the nearly limitless variety of plastics allowing fine-tuning of the optical properties of the support to suit the application for which it is intended or to which it may be put.

Where metals are used as substrates or as pads on a substrate, this may be because of the desired application: the conductivity of metals can allow modulation of the electric field in DNA-based sensors. In this way, DNA mismatch discrimination may be enhanced, the orientation of immobilized oligonucleotide molecules can be affected, or DNA hybridization kinetics can be accelerated.

In some embodiments, the substrate is silica-based but the shape of the substrate employed may be varied in accordance with the application for which the present application is practiced. Generally, however, slides of support material, such as silica, e.g. fused silica, are of particular utility in the preparation and subsequent integration of molecules. Of particular use in the practice of the present application are fused silica slides sold under the trade name SPECTRA-SIL™. This notwithstanding, it will be evident to the skilled person that the present application is equally applicable to other presentations of substrate (including silica-based supports), such as beads, rods and the like.

In some embodiments, the surface of the substrate comprises both functional molecules-coated regions and inert regions with no coatings. In some such embodiments, the functionalized molecule coatings are hydrogel or polymer coatings. The functional molecules-coated regions can comprise reactive sites, and thus, can be used to attach molecules through chemical bonding or other molecular interactions. In some embodiments, the functional molecules-coated regions (e.g. reactive features, pads, beads, posts or wells) and the inert regions (referred to as interstitial regions) can alternate so as to form a pattern or a grid. Such patterns can be in one or two dimensions. In some embodiments, the inert regions can be selected from glass regions, metal regions, mask regions, or combinations thereof. Alternatively these materials can form reactive regions. Inertness or reactivity will depend on the chemistry and processes used on the substrate. In one embodiment, the surface comprises glass regions. In another embodiment, the surface comprises metal regions. In still another embodiment, the surface comprises mask regions. In some embodiments of the compositions described herein, the substrate can be a bead. Non-limiting exemplary substrate materials that can be coated with a polymer of the present disclosure or that can otherwise be used in a composition or method set forth herein are described in U.S. Pat. Nos. 8,778,848 and 8,778,849, each of which is incorporated herein by reference.

In some embodiments, a substrate described herein forms at least part of a flow cell or is located in a flow cell. In some such embodiments, the flow cells further comprise polynucleotides attached to the surface of the substrate via the functional molecules coating, for example, a polymer coating. In some embodiments, the polynucleotides are present in the flow cells in polynucleotide clusters, wherein the polynucleotides of the polynucleotide clusters are attached to a surface of the flow cell via the polymer coating. In such embodiments, the surface of the flow cell body to which the polynucleotides are attached is considered the substrate. In other embodiments, a separate substrate having a polymer coated surface is inserted into the body of the flow cell. In preferred embodiments, the flow cell is a flow chamber that is divided into a plurality of lanes or a plurality of sectors, wherein one or more of the plurality of lanes or plurality of sectors comprises a surface that is coated with a covalently attached polymer coating described herein. In some embodiments of the flow cells described herein, the attached polynucleotides within a single polynucleotide cluster have the same or similar nucleotide sequence. In some embodiments of the flow cells described herein, the attached polynucleotides of different polynucleotide clusters have different or nonsimilar nucleotide sequences. Exemplary flow cells and substrates for manufacture of flow cells that can be used in method or composition set forth herein include, but are not limited to, those commercially available from Illumina, Inc. (San Diego, Calif.) or described in US 2010/0111768 A1 or US 2012/0270305, each of which is incorporated herein by reference.

Sequencing Application

A composition, apparatus or method set forth herein can be used with any of a variety of amplification techniques. Exemplary techniques that can be used include, but are not limited to, polymerase chain reaction (PCR), rolling circle amplification (RCA), multiple displacement amplification (MDA), or random prime amplification (RPA). In particular embodiments, one or more primers used for amplification can be attached to a polymer coating. In PCR embodiments, one or both of the primers used for amplification can be attached to a polymer coating. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference in its entirety. PCR amplification can also be carried out with one of the amplification primers attached to a polymer coating and the second primer in solution. An exemplary format that uses a combination of one attached primer and soluble primer is emulsion PCR as described, for example, in Dressman et al., *Proc. Natl. Acad. Sci. USA* 100:8817-8822 (2003), WO 05/010145, or U.S. Patent Publ. Nos. 2005/0130173 or 2005/0064460, each of which is incorporated herein by reference. Emulsion PCR is illustrative of the format and it will be understood that for purposes of the methods set forth herein the use of an emulsion is optional and indeed for several embodiments an emulsion is not used. Furthermore, primers need not be attached directly to substrate or solid supports as set forth in the ePCR references and can instead be attached to a polymer coating as set forth herein.

RCA techniques can be modified for use with a method, composition or apparatus of the present disclosure. Exemplary components that can be used in an RCA reaction and principles by which RCA produces amplicons are described, for example, in Lizardi et al., *Nat. Genet.* 19:225-232 (1998) and US 2007/0099208 A1, each of which is incorporated herein by reference. Primers used for RCA can be in solution or attached to a polymer coating.

MDA techniques can be modified for use with a method, composition or apparatus of the present disclosure. Some basic principles and useful conditions for MDA are described, for example, in Dean et al., *Proc. Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., *Nucl. Acids Res.* 20:1691-96 (1992); U.S. Pat. No. 5,455,166; U.S. Pat. No. 5,130,238; and U.S. Pat. No. 6,214,587, each of which is incorporated herein by reference. Primers used for MDA can be in solution or attached to a polymer coating.

In particular embodiments a combination of the above-exemplified amplification techniques can be used. For example, RCA and MDA can be used in a combination wherein RCA is used to generate a concatameric amplicon in solution (e.g. using solution-phase primers). The amplicon can then be used as a template for MDA using primers that are attached to a polymer coating. In this example, amplicons produced after the combined RCA and MDA steps will be attached to the polymer coating.

In some embodiments, the functionalized hydrogel or polymer-coated substrate described herein can be used in a method for determining a nucleotide sequence of a polynucleotide. In such embodiments, the method can comprise the steps of (a) contacting a polynucleotide polymerase with polynucleotide clusters attached to a surface of a substrate via any one of the polymer or hydrogel coatings described herein; (b) providing nucleotides to the polymer-coated surface of the substrate such that a detectable signal is generated when one or more nucleotides are utilized by the polynucleotide polymerase; (c) detecting signals at one or more polynucleotide clusters; and (d) repeating steps (b) and (c), thereby determining a nucleotide sequence of a polynucleotide present at the one or more polynucleotide clusters.

Nucleic acid sequencing can be used to determine a nucleotide sequence of a polynucleotide by various processes known in the art. In a preferred method, sequencing-by-synthesis (SBS) is utilized to determine a nucleotide sequence of a polynucleotide attached to a surface of a substrate via any one of the polymer coatings described herein. In such process, one or more nucleotides are provided to a template polynucleotide that is associated with a polynucleotide polymerase. The polynucleotide polymerase incorporates the one or more nucleotides into a newly synthesized nucleic acid strand that is complementary to the polynucleotide template. The synthesis is initiated from an oligonucleotide primer that is complementary to a portion of the template polynucleotide or to a portion of a universal or non-variable nucleic acid that is covalently bound at one end of the template polynucleotide. As nucleotides are incorporated against the template polynucleotide, a detectable signal is generated that allows for the determination of which nucleotide has been incorporated during each step of the sequencing process. In this way, the sequence of a nucleic acid complementary to at least a portion of the template polynucleotide can be generated, thereby permitting determination of the nucleotide sequence of at least a portion of the template polynucleotide.

Flow cells provide a convenient format for housing an array that is produced by the methods of the present disclosure and that is subjected to a sequencing-by-synthesis (SBS) or other detection technique that involves repeated delivery of reagents in cycles. For example, to initiate a first SBS cycle, one or more labeled nucleotides, DNA polymerase, etc., can be flowed into/through a flow cell that houses a nucleic acid array made by methods set forth herein. Those sites of an array where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., *Nature* 456: 53-59 (2008), WO 04/018497; U.S. Pat. No. 7,057,026; WO 91/06678; WO 07/123744; U.S. Pat. No. 7,329,492; U.S. Pat. No. 7,211,414; U.S. Pat. No. 7,315,019; U.S. Pat. No. 7,405,281, and US 2008/0108082, each of which is incorporated herein by reference in its entirety.

Other sequencing procedures, including for example those that use cyclic reactions, can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. No. 6,210,891; U.S. Pat. No. 6,258,568 and U.S. Pat. No. 6,274,320, each of which is incorporated herein by reference in its entirety). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WO 12/058096 A1, US 2005/0191698 A1, U.S. Pat. No. 7,595,883, and U.S. Pat. No. 7,244,559, each of which is incorporated herein by reference in its entirety.

Sequencing-by-ligation reactions are also useful including, for example, those described in Shendure et al. *Science* 309:1728-1732 (2005); U.S. Pat. No. 5,599,675; and U.S. Pat. No. 5,750,341, each of which is incorporated herein by reference in its entirety. Some embodiments can include sequencing-by-hybridization procedures as described, for example, in Bains et al., *Journal of Theoretical Biology* 135(3), 303-7 (1988); Drmanac et al., *Nature Biotechnology* 16, 54-58 (1998); Fodor et al., *Science* 251(4995), 767-773 (1995); and WO 1989/10977, each of which is incorporated herein by reference in its entirety. In both sequencing-by-ligation and sequencing-by-hybridization procedures, nucleic acids that are present at sites of an array are subjected to repeated cycles of oligonucleotide delivery and detection. Fluidic systems for SBS methods as set forth herein or in references cited herein can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. Science 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference in its entirety.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference in its entirety.

Another useful application for an array of the present disclosure, for example, having been produced by a method set forth herein, is gene expression analysis. Gene expression can be detected or quantified using RNA sequencing techniques, such as those, referred to as digital RNA sequencing. RNA sequencing techniques can be carried out using sequencing methodologies known in the art such as those set forth above. Gene expression can also be detected or quantified using hybridization techniques carried out by direct hybridization to an array or using a multiplex assay, the products of which are detected on an array. An array of the present disclosure, for example, having been produced by a method set forth herein, can also be used to determine genotypes for a genomic DNA sample from one or more individual. Exemplary methods for array-based expression and genotyping analysis that can be carried out on an array of the present disclosure are described in U.S. Pat. Nos. 7,582,420; 6,890,741; 6,913,884 or 6,355,431 or U.S. Pat. Pub. Nos. 2005/0053980 A1; 2009/0186349 A1 or US 2005/0181440 A1, each of which is incorporated herein by reference in its entirety.

In some embodiments of the above-described method which employ a flow cell, only a single type of nucleotide is present in the flow cell during a single flow step. In such embodiments, the nucleotide can be selected from the group consisting of dATP, dCTP, dGTP, dTTP and analogs thereof. In other embodiments of the above-described method which employ a flow cell, a plurality of different types of nucleotides are present in the flow cell during a single flow step. In such methods, the nucleotides can be selected from dATP, dCTP, dGTP, dTTP and analogs thereof.

Determination of the nucleotide or nucleotides incorporated during each flow step for one or more of the polynucleotides attached to the polymer coating on the surface of the substrate present in the flow cell is achieved by detecting a signal produced at or near the polynucleotide template. In some embodiments of the above-described methods, the detectable signal comprises and optical signal. In other embodiments, the detectable signal comprises a non-optical signal. In such embodiments, the non-optical signal comprises a change in pH at or near one or more of the polynucleotide templates.

EXAMPLES

Additional embodiments are disclosed in further detail in the following examples, which are not in any way intended to limit the scope of the claims.

Example 1

Scheme 1. Synthesis of Orthogonally Bifunctionalized Polyacrylamides

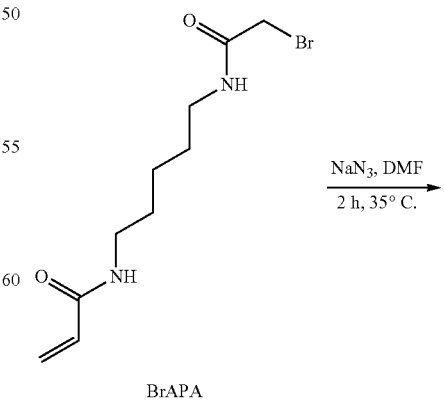

BrAPA

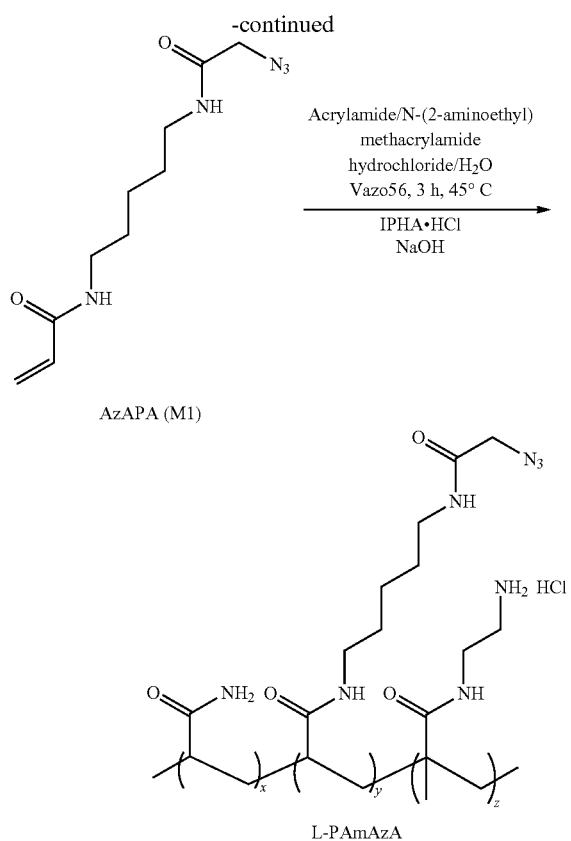

AzAPA (M1)

L-PAmAzA

Scheme 1 illustrates a synthetic scheme for the preparation of poly-acrylamide-co-AzAPA-co-aminoethylacrylamide (L-PAmAzA). In the first step, N-(5-azidoacetamidylpentyl) acrylamide (AzAPA) was synthesized from reacting N-(5-bromoacetamidylpentyl) acrylamide (BrAPA) with sodium azide in DMF at 35° C. for 2 hours. Then, L-PAmAzA was synthesized using an AIBN-type polymer initiation system (Vazo56) by reacting AzAPA with acrylamide and N-(2-aminoethyl)methacrylamide HCl. The resulting L-PAmAzA has the three recurring units in the molar ratio x:y:z of about 90% to about 5% to about 5%.

In addition, crosslinking of the L-PAmAzA was achieved by the introduction of N,N'-methylenebisacrylamide monomers into the polymerization reaction, which resulted in a crosslinked polymer (XL-PAmAzA) with exemplary structure shown as follows:

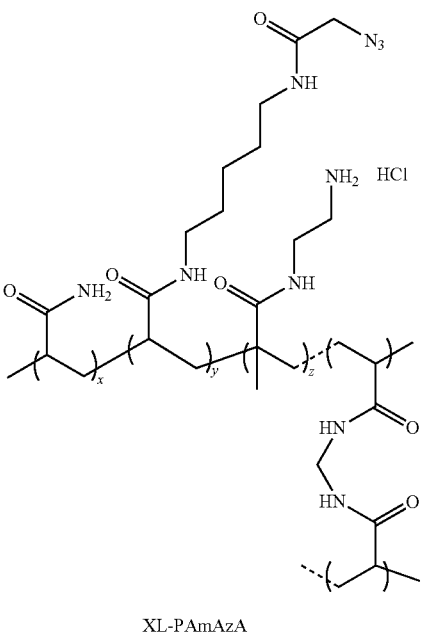

XL-PAmAzA x:y:z = ~90:~5:~5

A series of linear polyacrylamides bearing orthogonal functionalities were prepared using the thermal initiator Vazo56 following the similar procedure described above. The reaction time was about 1.5 hours to about 3 hours, followed by a purification step through precipitation into MeCN. Table 1 below summarizes the amounts of the monomers for the polymerization reactions.

TABLE 1

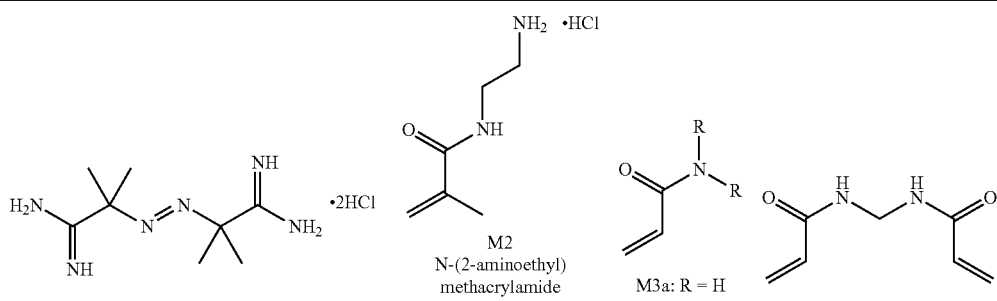

| Polymer | M1 (mol %) | M2 (mol %) | M3a/b (mol %) | M4 (mol %) |
|---|---|---|---|---|
| 1 | 5 | 5 | a: 90 | 0 |
| 2 | 5 | 5 | a: 90 | 1 |
| 3 | 5 | 10 | a: 85 | 1 |
| 4 | 5 | 5 | b: 90 | 1 |
| 5 | 5 | 5 | a: 90 | 2 |
| 6 | 5 | 5 | a: 90 | 0.5 |

In order to demonstrate the orthogonal reactivity of the bifunctional polyacrylamides, the coating performance of three new polyacrylamides in Table 1 (Polymer 1, "P1"; Polymer 4, "P4"; Polymer 6, "P6") containing 5 mol % aminoethyl functionality on epoxy monolayer surface was assessed against the standard norbornene monolayer surface. Polymer 1 and Polymer 6 are L-PAmAzA and XL-PAmAzA with the structures illustrated above. The simplified structure of Polymer 4 is shown below.

Standard PAZAM polymer was used as control. The flow cell layout for the norbornene monolayer surface and the epoxy monolayer surface are summarized in Table 2 and Table 3 respectively.

TABLE 2

| Channel | Polymer coupling Temperature (° C.) | Polymer coupling time (min) | Vol. std. PAZAM (uL) | Polymer | [Final PAZAM]/ w/v % | [P5/P7]/ uM |
| --- | --- | --- | --- | --- | --- | --- |
| 1 | 60 | 60 | 420 | PAZAM control | 0.5 | 18 |
| 2 | 60 | 60 | 420 | P1 | 0.5 | 18 |
| 3 | 60 | 60 | 420 | P4 | 0.5 | 18 |
| 4 | 60 | 60 | 420 | P6 | 0.5 | 18 |
| 5 | 60 | 60 | 420 | PAZAM control | 0.5 | 18 |
| 6 | 60 | 60 | 420 | P1 | 0.5 | 18 |
| 7 | 60 | 60 | 420 | P4 | 0.5 | 18 |
| 8 | 60 | 60 | 420 | P6 | 0.5 | 18 |

TABLE 3

| Channel | Polymer coupling temperature (° C.) | Polymer coupling time (min) | Vol. std. PAZAM (uL) | Polymer | [Final PAZAM]/ w/v % | [P5/P7]/uM |
| --- | --- | --- | --- | --- | --- | --- |
| 1 | 60 | 60 | 420 | PAZAM control | 0.5 | 18 |
| 2 | 60 | 60 | 420 | P1 | 0.5 | 18 |
| 3 | 60 | 60 | 420 | P4 | 0.5 | 18 |
| 4 | 60 | 60 | 420 | P6 | 0.5 | 18 |
| 5 | 60 | 60 | 420 | PAZAM control | 0.5 | 18 |
| 6 | 60 | 60 | 420 | P1 | 0.5 | 18 |
| 7 | 60 | 60 | 420 | P4 | 0.5 | 18 |
| 8 | 60 | 60 | 420 | P6 | 0.5 | 18 |

Polymer 4

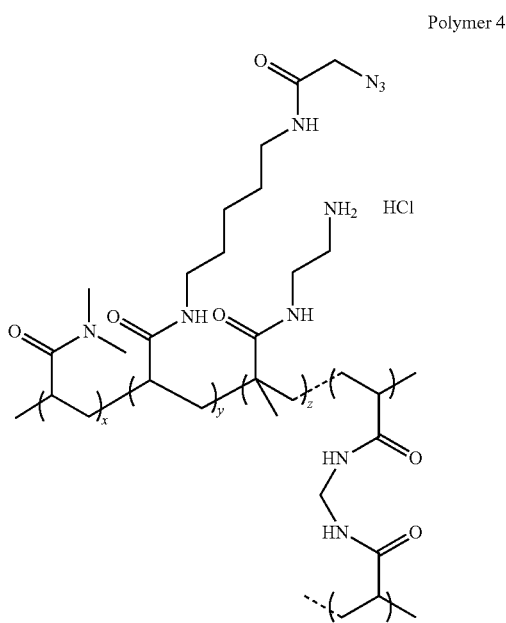

x:y:z = ~90:~5:~5

HiSeq substrates (provided by ILLUMINA, San Diego, Calif.) were used for this initial screening and the CVD process was performed using a desiccator. The bifunctional polyacrylamides polymers reacted with norbornene via strain-promoted azide click reaction to covalently bond to the norbornene monolayer surface at 60° C. Similarly, bifunctional polyacrylamides polymers were coated onto the epoxy monolayers via epoxy ring opening reaction with amine functional groups which results in covalent bonding of the polymers to the surface. Two QC metrics were used to measure the success of the method. Both QC1 and QC3 utilize green laser, with PMT at 450V and filter emission at 555 BP. The TET QC oligo mix for QC1 is 1.6 mM: 100 mL oligos at 16 μM+0.9 mL HT1. The TET QC oligo mix for QC3 is 0.6 mM (each): 35 mL oligos at 16 μM+0.9 mL HT1. The Typhoon florescence image of the polymers coated flow cell and the related chart of median Typhoon intensity of the polymers on the norbornene silane monolayer surface for TET QC1 and TET QC3 are illustrated in FIGS. 1A, 1B, 1C and 1D respectively. The Typhoon florescence image of the polymers coated flow cell and the related chart of median Typhoon intensity of the polymers on the epoxy silane monolayer surface for TET QC1 and TET QC3 are illustrated in FIGS. 2A, 2B, 2C and 2D respectively.

TET QC measurements for the norbornene surface and the epoxy surface are summarized in Table 4 and Table 5 respectively.

TABLE 4

| Lanes | % Intensity change, QC1->QC3 | % Surface Loss | Polymer |
|---|---|---|---|
| 1 | 11% | −11% | PAZAM control |
| 2 | −1% | 1% | P1 |
| 3 | 0% | 0% | P4 |
| 4 | −3% | 3% | P6 |
| 5 | 13% | −13% | PAZAM control |
| 6 | −2% | 2% | P1 |
| 7 | −6% | 6% | P4 |
| 8 | −5% | 5% | P6 |

TABLE 5

| Lanes | % Intensity change, QC1->QC3 | % Surface Loss | Polymer |
|---|---|---|---|
| 1 | 84% | −84% | PAZAM control |
| 2 | 31% | −31% | P1 |
| 3 | 11% | −11% | P4 |
| 4 | 13% | −13% | P6 |
| 5 | 84% | −84% | PAZAM control |
| 6 | 32% | −32% | P1 |
| 7 | 12% | −12% | P4 |
| 8 | 24% | −24% | XL-PAAm3 |

Figure 3A:
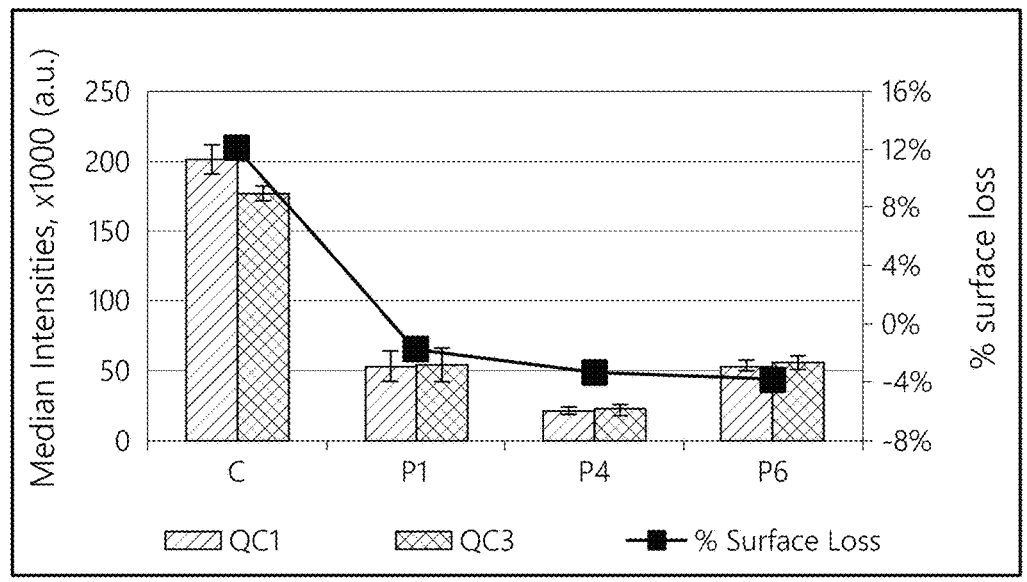
FIG. 3A is a line and bar chart that illustrates the TET QC intensity data (Table 4) after coating a norbornene surface with different polymers as listed in Example 1 (Table 2) and surface loss percentage as measured after a thermal Stress Test.
Figure 3B:
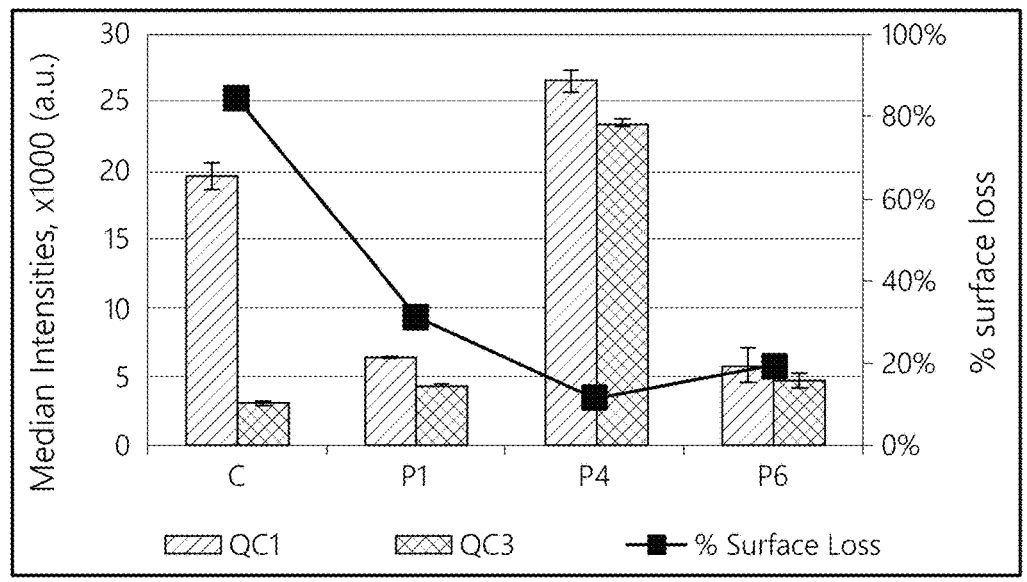
FIG. 3B is a line and bar chart that illustrates the TET QC intensity data (Table 5) after coating an epoxy surface with different polymers as listed in Example 1 (Table 3) and surface loss percentage as measured after a thermal Stress Test.

The results from the above noted pair of flow cells provided evidence supporting the use of orthogonal reactivity of the polyacrylamide materials to support Sequencing-by-Synthesis. First, all the azido-functionalized materials tested were capable of adhering securely to a norbornene surface. This means that the azide incorporation into the polymer structure was such that a stable surface could be obtained, as measured by a thermal stress test. Second, all of the amine-functionalized polymers were capable of coating the epoxy surface that was generated by the use of a desiccator. The surface primer densities were approximately 20-30 k. In these experiments, the control polymer (i.e., the standard PAZAM), which contained no amine functionality, showed the largest surface loss after the thermal stress test. This is the expected result. The bifunctionalized polyacrylamide polymers P1, P4 and P6, each with 5% amine functionality, showed reasonable surface stability. The results indicated that these polyacrylamide coated surfaces were robust (surface losses ranging from about 20% to 30% after subjecting the polymer coated surface to the standard Stress test). The results of TET QC signal changes of the norbornene monolayer surface and the epoxy monolayer surface are shown in FIG. 3A and FIG. 3B respectively. Of the three bifunctionalized polyacrylamides tested, Polymer 4 demonstrates the best surface robustness.

The orthogonal polyacrylamides prepared by the procedure described above are generally random copolymers. It may be desirable to separate different functional parts of the polymer architecture, for example, separating all the azide functional groups from all the amine functional groups to different segments of the polymer chain. This alternative synthesis is readily achievable using controlled radical polymerization (CRP) methods (e.g., RAFT, ATRP). Scheme 2.1 and 2.2 demonstrate two synthetic routes for preparing a block copolymer AEMA-b-AzAPA (Polymer 7).

Scheme 2.1.

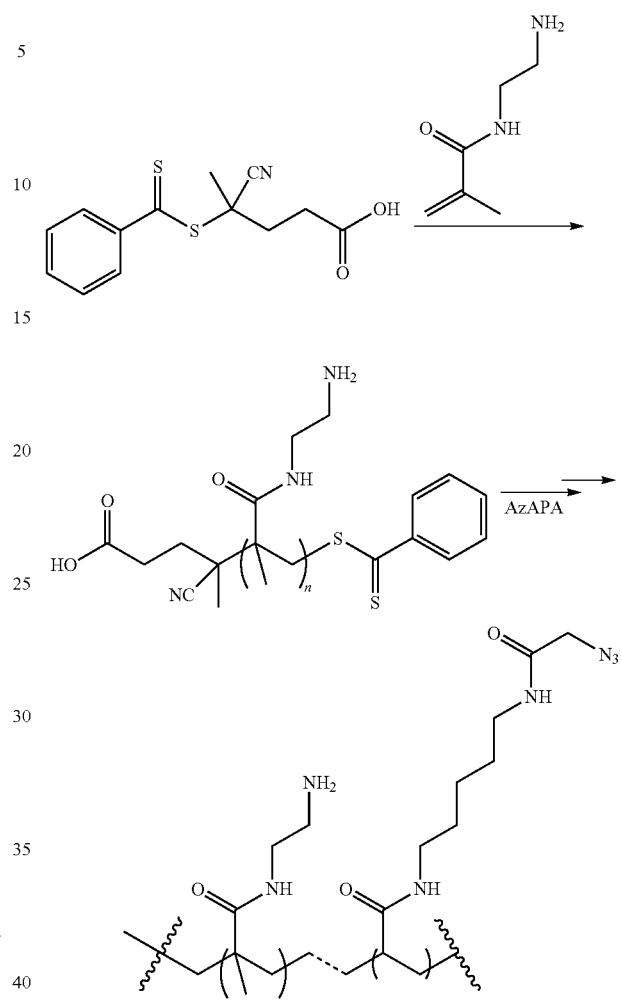

Scheme 2.2.

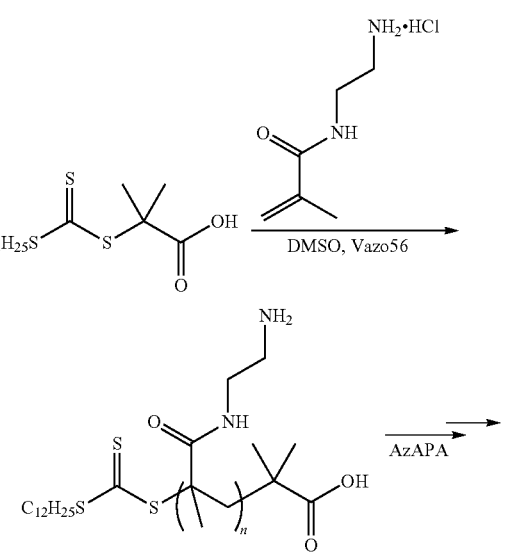

-continued

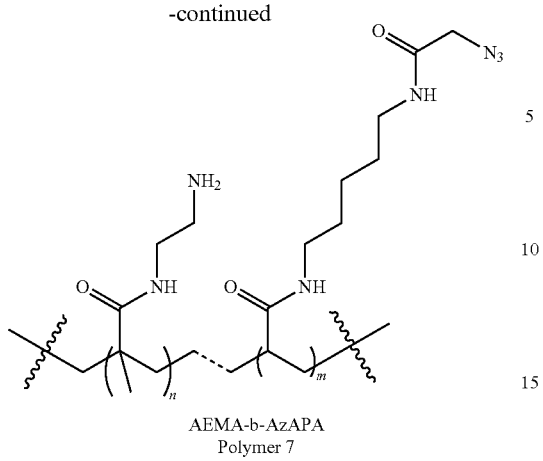

AEMA-b-AzAPA
Polymer 7

The coating performance of a block copolymer AEMA-b-AzAPA prepared by a RAFT technique according to Scheme 2.2 was compared to that of a random copolymer Polymer 4 on epoxy silane monolayer surface. The CVD process was performed on the flow cell using a desiccator in an oven at 60° C. and the flow cell was incubated overnight. The flow cell layout is summarized in Table 6. The coupling reaction between the amino functional groups of Polymer 7 and Polymer 4 with the epoxy surface was performed at 60° C. for an hour.

TABLE 6

| Channel | Polymer coupling temp. (° C.) | Polymer/Epoxy surface coupling time (min) | Vol. of polymer used for coating (μL) | Polymer | Approx. [polymer]/ w/v % | [P5/P7]/ μM |
|---|---|---|---|---|---|---|
| 1 | 60 | 60 | 450 | Polymer 7 | 0.3* | 10 |
| 2 | 60 | 60 | 450 | Polymer 7 | 0.3* | 10 |
| 3 | 60 | 60 | 450 | Polymer 7 | 0.3* | 10 |
| 4 | 60 | 60 | 450 | Polymer 7 | 0.3* | 10 |
| 5 | 60 | 60 | 450 | Polymer 4 | 0.5 | 10 |
| 6 | 60 | 60 | 450 | Polymer 4 | 0.5 | 10 |
| 7 | 60 | 60 | 450 | Polymer 4 | 0.5 | 10 |
| 8 | 60 | 60 | 450 | Polymer 4 | 0.5 | 10 |

*The solids content of this batch, as measured by RI, was very high (4.9% Brix @ 0.3% w/v)

Figure 4A:
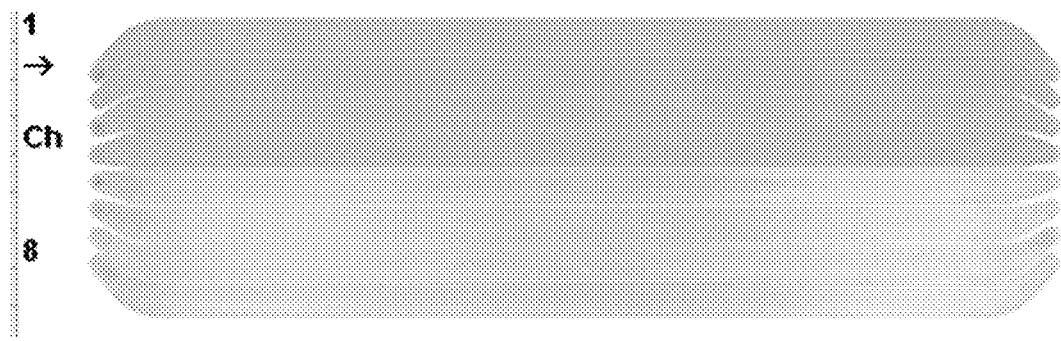
FIGS. 4A to 4D show the Typhoon florescence image of the polymers coated flow cell with norbornene silane monolayer surface and the related bar chart of median Typhoon intensity of the polymers of Example 1 (Table 6).
Figure 4B:
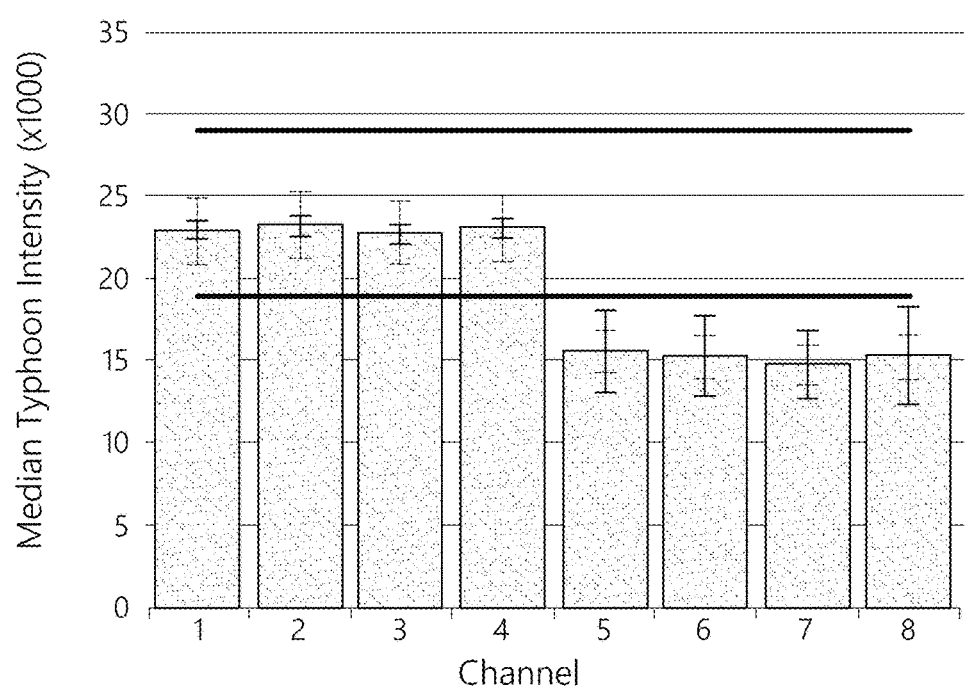
Figure 4C:
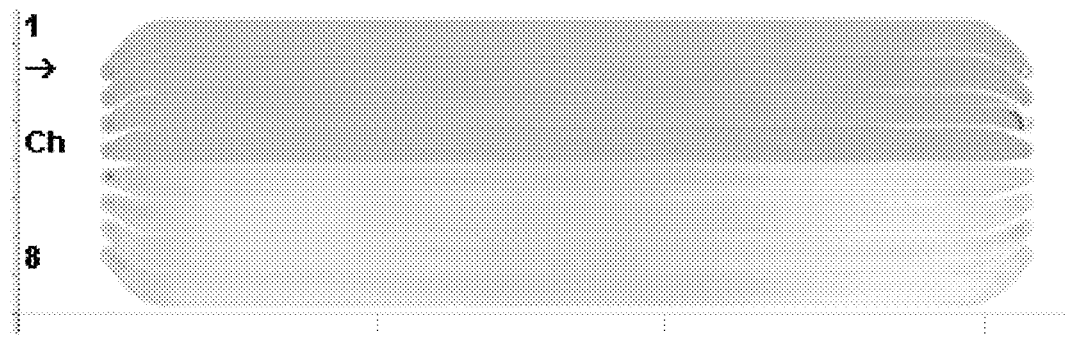
Figure 4D:
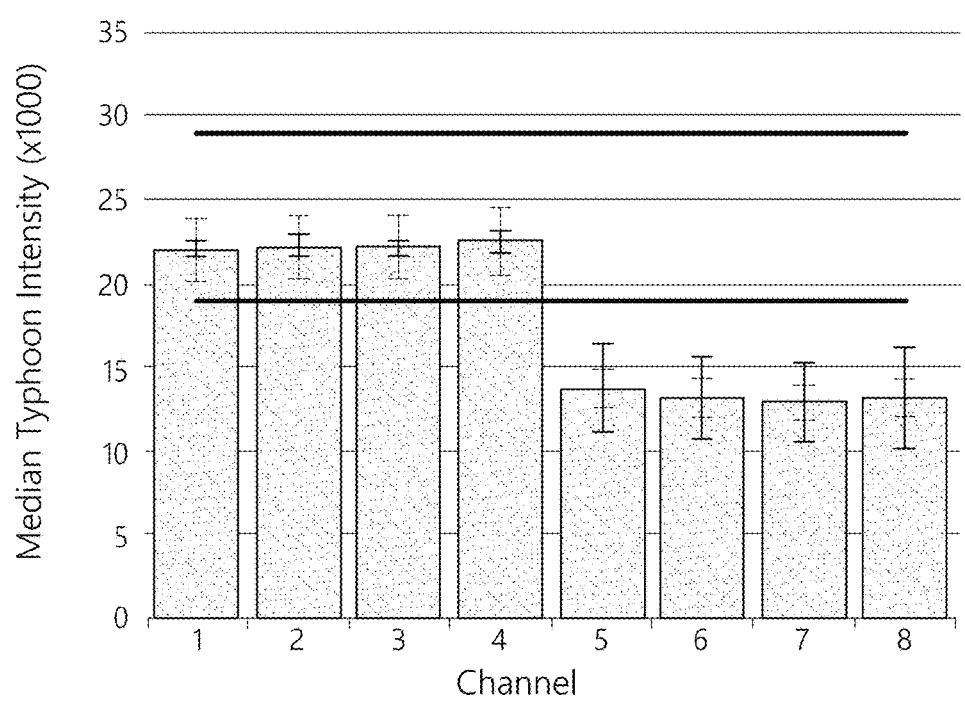
Figure 4E:
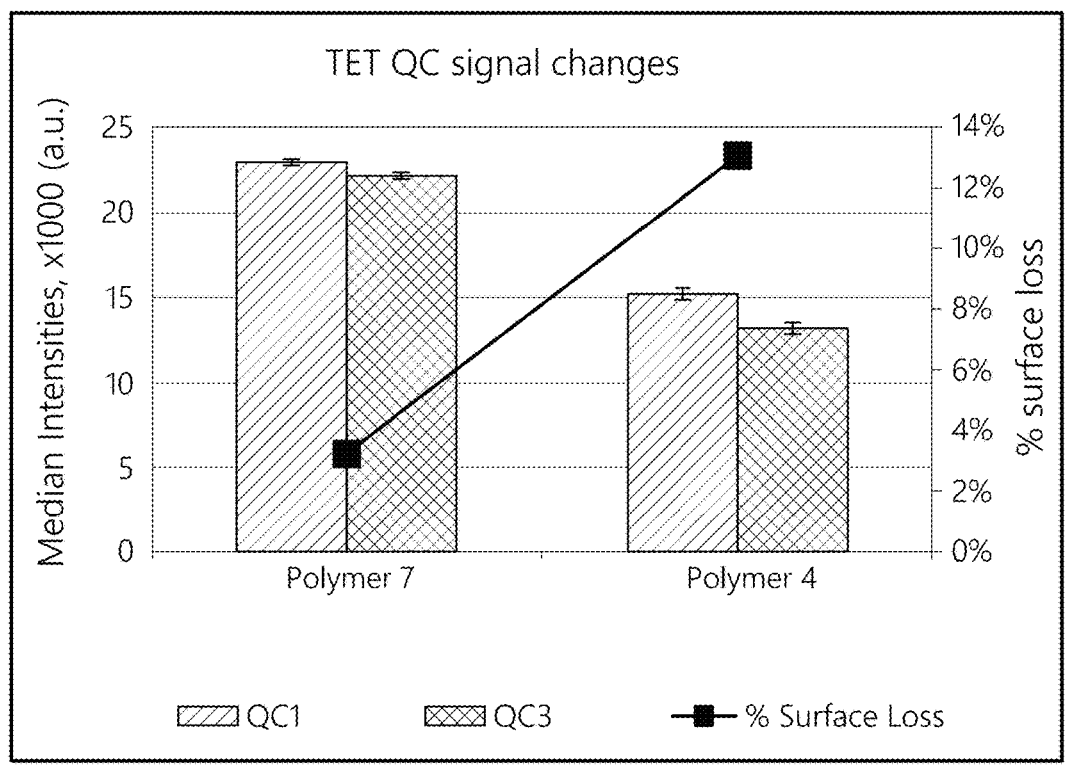
FIG. 4E is a line and bar chart that illustrates the TET QC intensity data (Table 7) after coating a norbornene surface with different polymers as listed Example 1 (Table 6) and surface loss percentage as measured after a thermal Stress Test.

Two QC metrics (QC1 and QC3) were used to measure the success of the method. The Typhoon florescence image of the polymers coated flow cell and the related chart of median Typhoon intensity of the polymers on the epoxy silane monolayer surface for TET QC1 and TET QC3 are illustrated in FIGS. 4A, 4B, 4C and 4D respectively. The results of TET QC signal change are shown in FIG. 4E. TET QC measurements for the epoxy surface are summarized in Table 7 below. Both materials yielded stable surfaces as measured by TET QC performed after a thermal Stress Test. In each case, the coatings were very uniform.

TABLE 7

| Lanes | Polymer | % Intensity change, QC1->QC3 | % Surface Loss |
|---|---|---|---|
| 1 | Polymer 7 | 4% | −4% |
| 2 | Polymer 7 | 4% | −4% |
| 3 | Polymer 7 | 3% | −3% |
| 4 | Polymer 7 | 2% | −2% |
| 5 | Polymer 4 | 12% | −12% |
| 6 | Polymer 4 | 13% | −13% |
| 7 | Polymer 4 | 13% | −13% |
| 8 | Polymer 4 | 14% | −14% |

Example 2
Scheme 3.
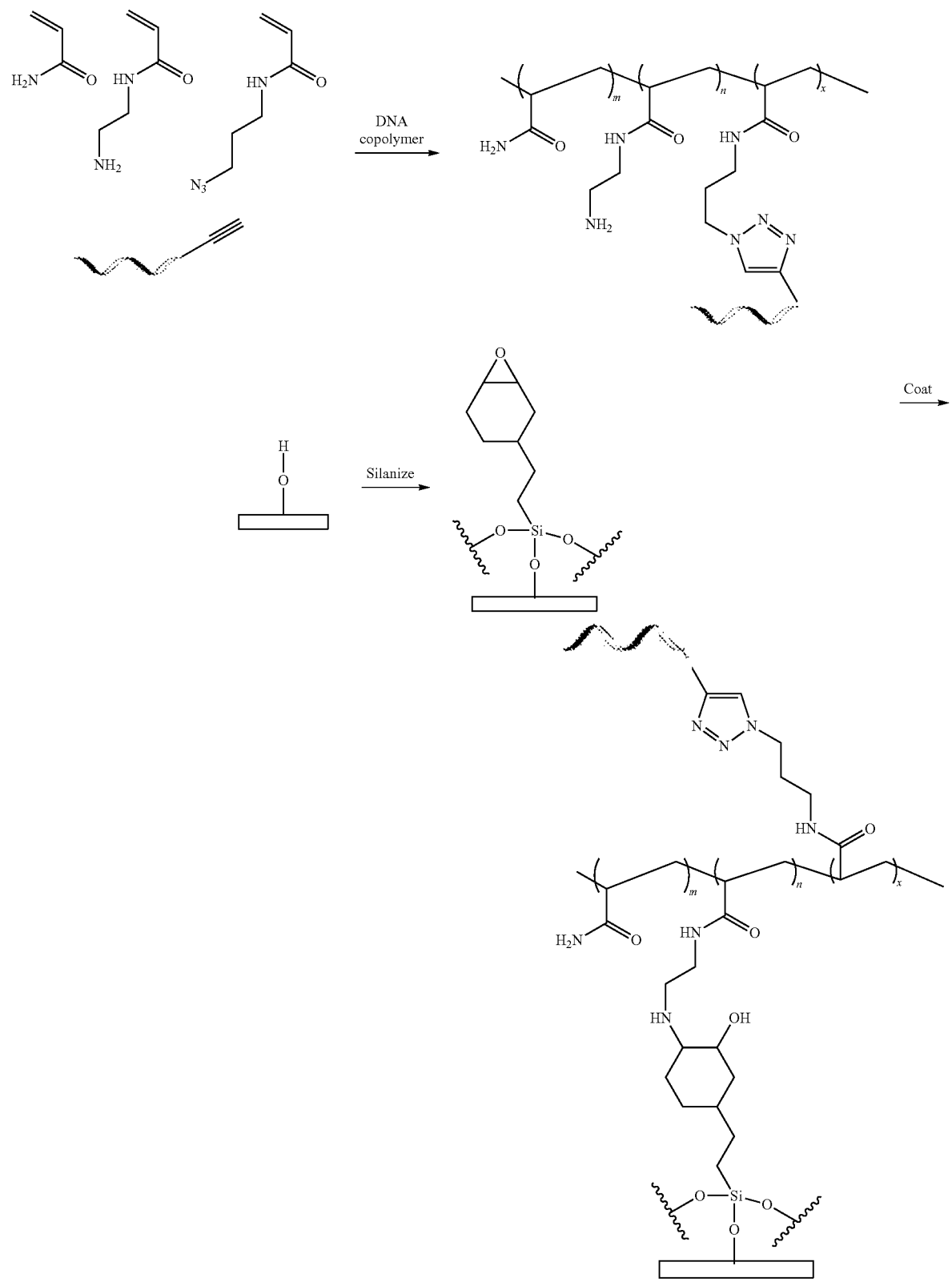

Scheme 3 illustrates a flow chart of substrate preparation by immobilizing a DNA copolymer to a silanized substrate surface. First, DNA copolymer is formed by reacting alkyne functionalized primers with acrylamide, azido-acrylamide and amino-acrylamide monomers to form a pre-grafted ternary copolymer (DNA copolymer). The substrate surface is first treated with a silane comprising epoxy groups. Then the DNA copolymer is immobilized to the substrate surface by reacting the primary amino groups of the polymer with the epoxy groups of the silane. The architecture of the DNA copolymer prepared by this process may be modified by addition of other monomers, for example, N,N-methylenebisacrylamide can be added to introduce crosslinking in a defined manner, or inimers (or monomer-initiators) can be added to introduce branching points in a defined manner. Controlled polymerization techniques such as RAFT, ATRP, or NMP may also be used to create block copolymer structures separating out the functional parts of the polymer to be more effective, if needed.

Example 3

Scheme 4. Oligo Reaction with Tetrazine-Functionalized Polymer

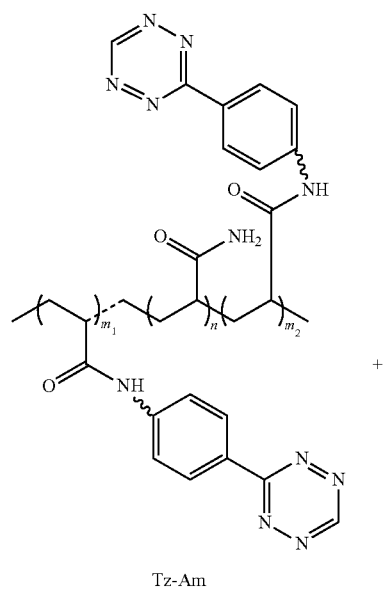

Tz-Am

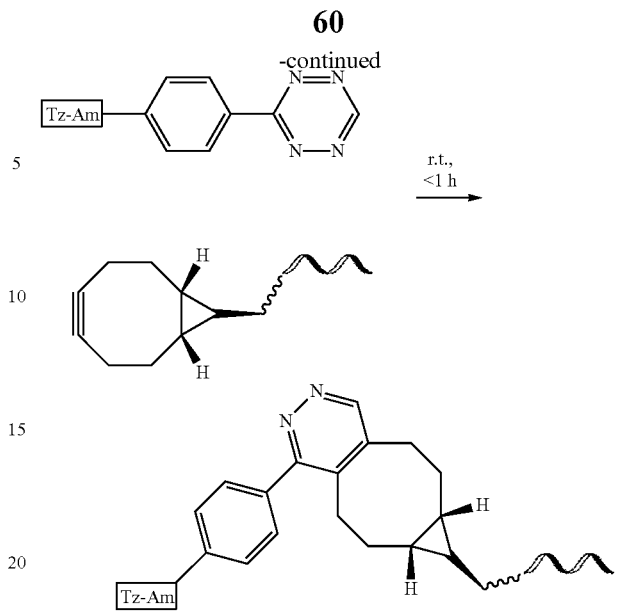

Scheme 4 illustrates the reaction between bicyclo[6.1.0] non-4-yne ("BCN") functionalized P5 or P7 primers with tetrazine modified acrylamide polymer ("Tz-Am") to form a grafted polymer. This catalyst-free, strain promoted click reaction can be performed at room temperature and it is compatible with aqueous environment. The resulting grafted polymer can be purified using a number of methods, e.g. precipitation or tangential flow filtration ("TFF") etc. Other non-limiting possible polymer backbones that can be used in this process include polyacrylates or polyphosphazenes.

Scheme 5. Attachment of Pre-grafted Tetrazine Polymer to Surface

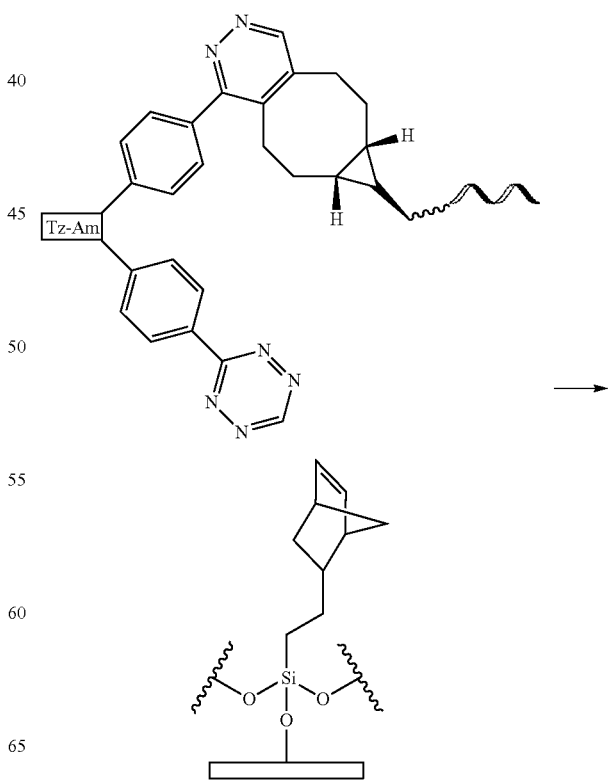

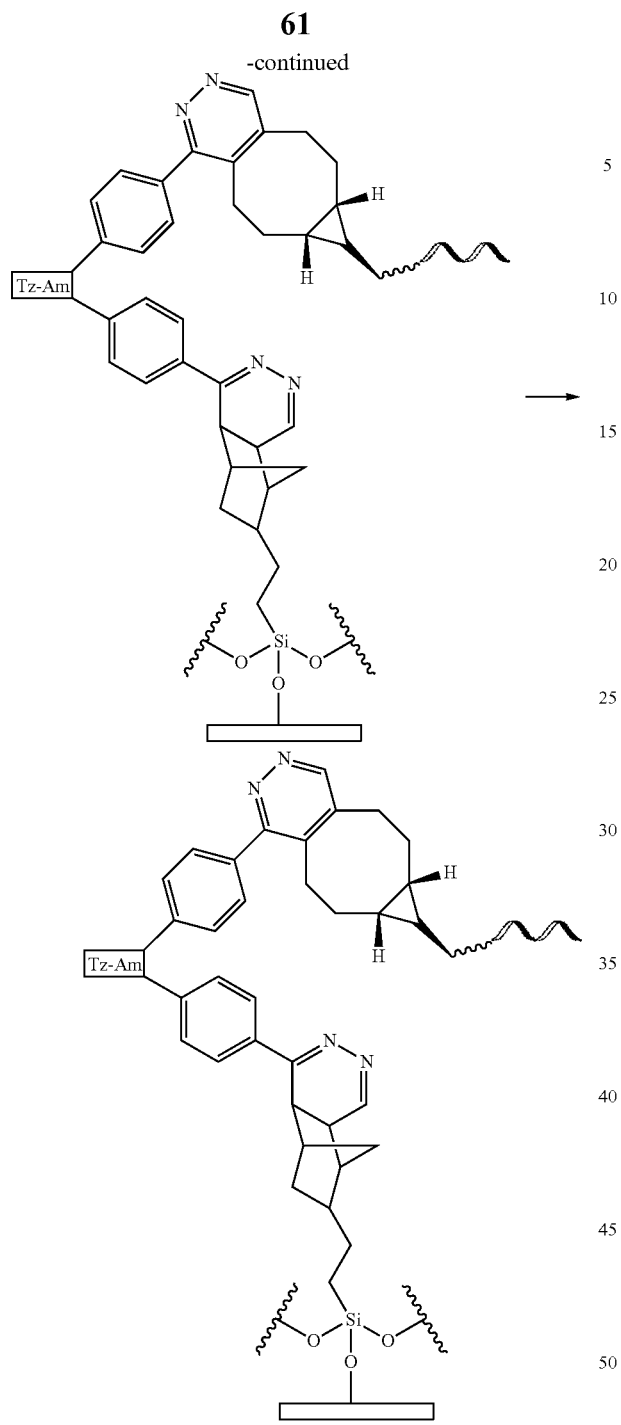

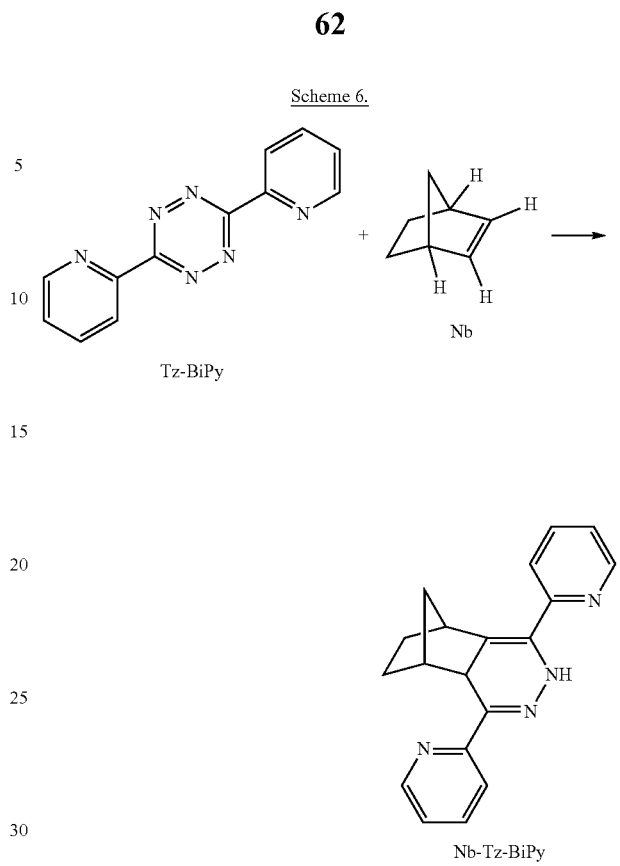

Scheme 6.

Figure 5:
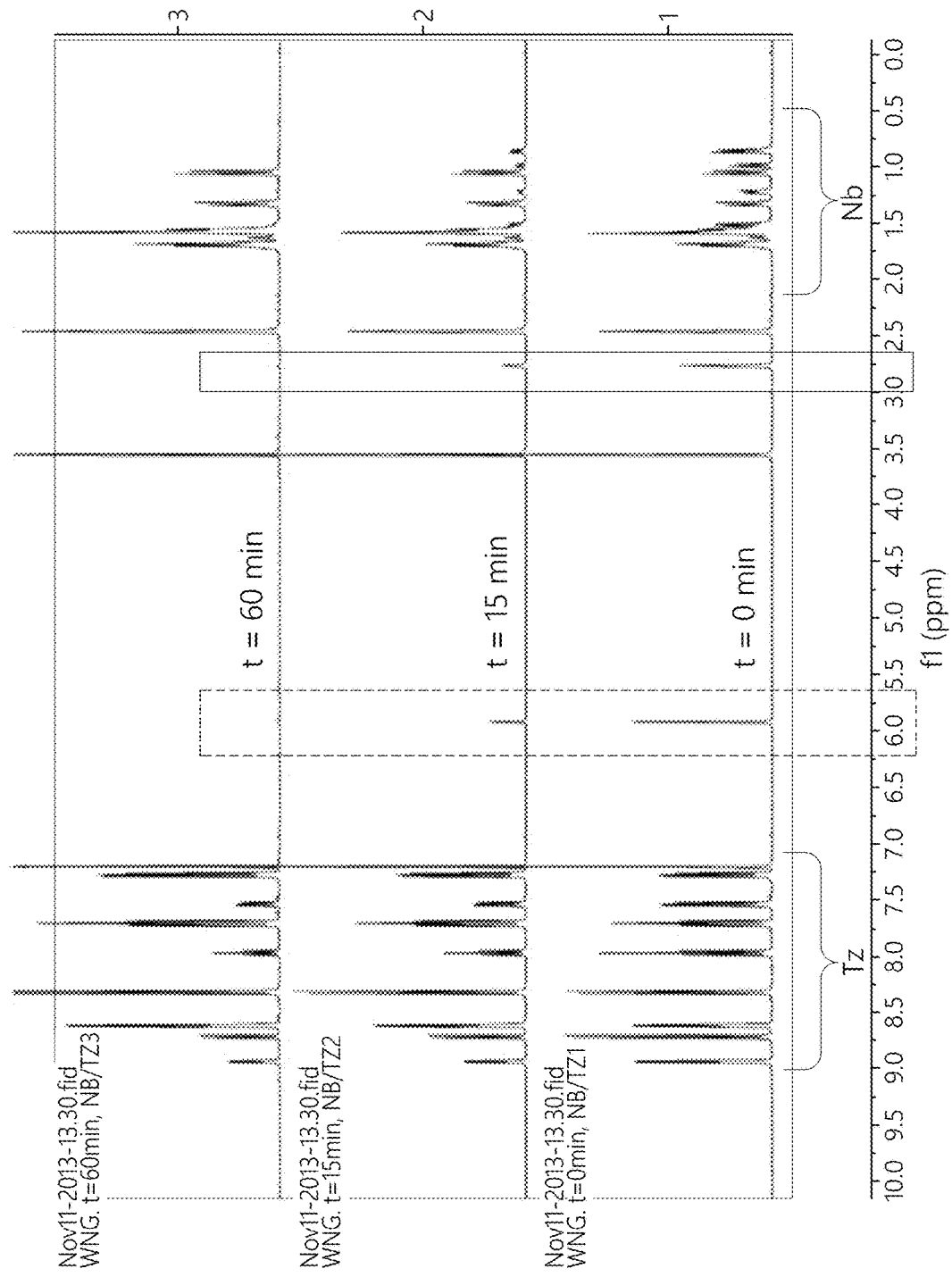
FIG. 5 shows a series of NMR images of a reaction between norbornene and a bipyridyl tetrazine at different time points.

Scheme 6 demonstrates the reaction between norbornene (Nb) and a commercially available bipyridyl tetrazine (BiPy) at 1:1 mole ratio. The reaction was carried out at room temperature in an NMR tube, using $CDCl_3$ as solvent with mild agitation. A NMR spectrum of the reaction mixture was taken at three different time points, one at the beginning of the reaction (t=0), one at 15 minutes and one at 60 minutes. The NMR spectra showed that the peak of the two alkene hydrogens of norbornene (with chemical shift at about 5.8 ppm) was disappearing and became almost invisible after one hour (See FIG. 5). This indicates the rapid kinetics of the reaction between tetrazine and norbornene.

Scheme 7.

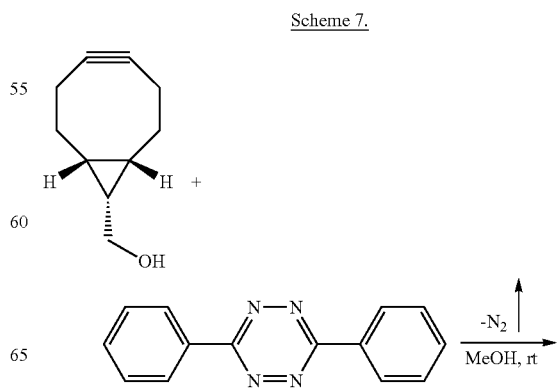

Scheme 5 illustrates the attachment of the pre-grafted tetrazine acrylamide polymer to norbornene functionalized surface of a substrate. The norbornene silanized surface is a standard part of the NextSeq® platform of Illumina. Alternatively, tetrazine functionalized polymer and BCN primers may be attached to the substrate surface in situ instead of forming the grafted polymer.

To assess the feasibility of this approach, initial experiments were carried out using a model system in a small scale solution reaction (Scheme 6).

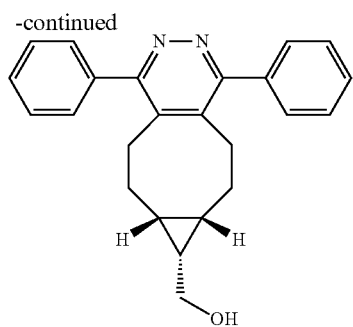

Figure 6:
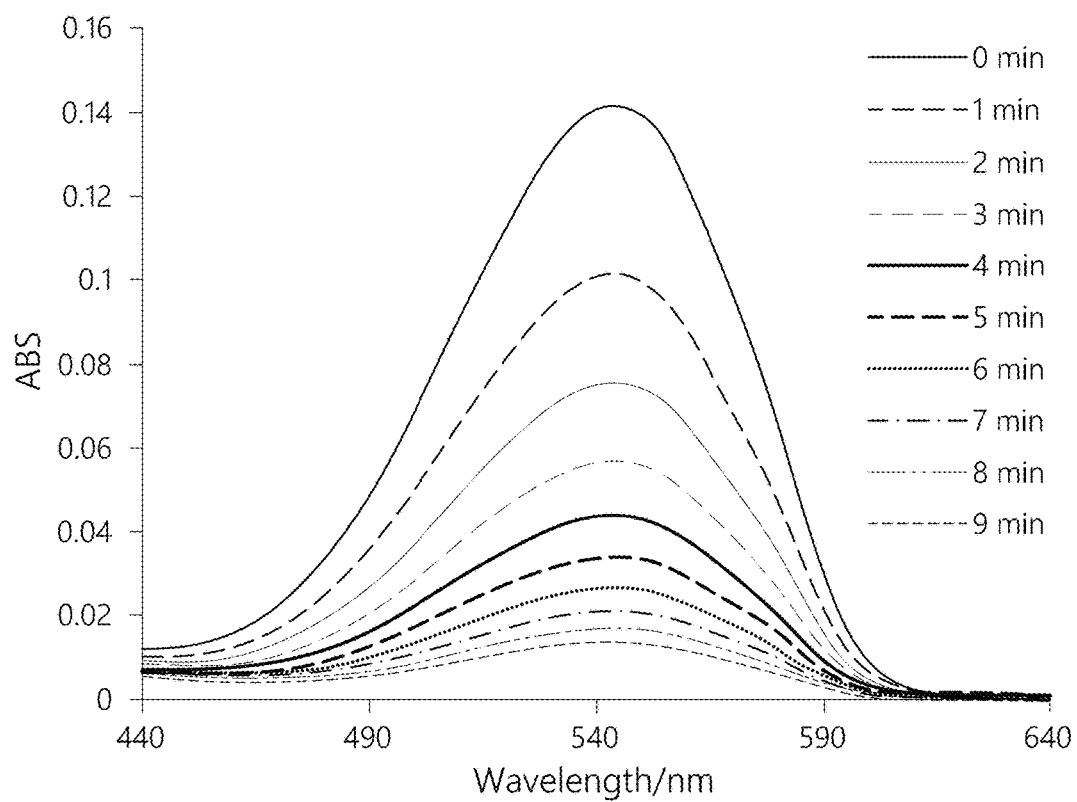
FIG. 6 shows a line graph of aUV-Vis absorption pattern of a reaction between bipyridyl tetrazine and bicyclo[6.1.0] non-4-yn-9-yl methanol.

In a separate experiment, Scheme 7 demonstrates a facile strain promoted [4+2] cycloaddition of cyclooctyne (10 mM) with a bisphenyl substituted 1,2,4,5-tetrazine (1 mM). The reaction was carried out at room temperature in dried MeOH. FIG. 6 shows the pattern of UV-vis absorption decrease of cyclooctyne which indicates the reaction was nearly completed after only 9 minutes. See W. Chen, D. Wang, C. Dai, D. Hamelberg B. Wang, *Chem. Commun.*, 2012, 48, 1736-1738.

Example 4

Scheme 8. Preparation of Pre-grafted Poly(Glycidyl Methacrylate)

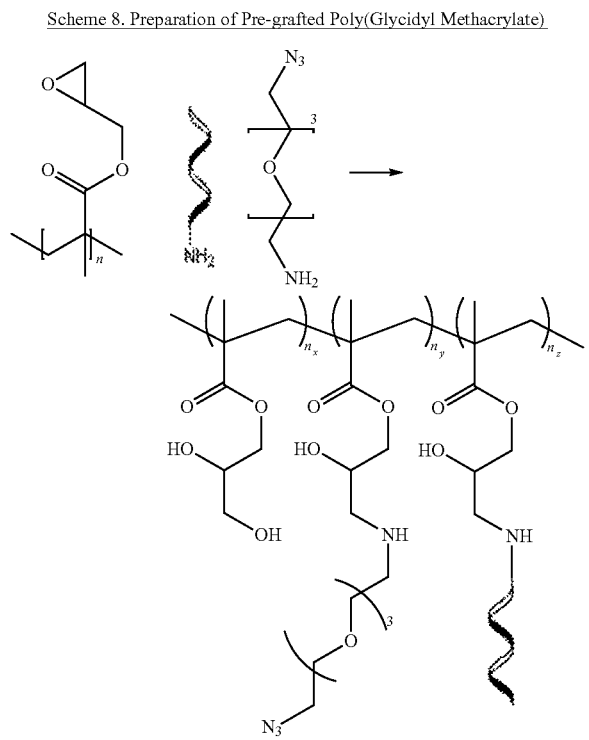

Scheme 8 illustrates the preparation of a pre-grafted poly(glycidyl methacrylate) comb polymer by reacting the glycidyl ether groups of the poly(glycidyl methacrylate) with the amino groups of the functionalized primers and amino-PEG-azide. This grafted polymer can be attached to a standard norbornene surface via catalyst-free, strain promoted click reaction between the side chain azido groups of the polymer and the norbornenes. A number of commercially available amino azides can be used and the azido groups may also be replaced with other orthogonal functional groups.

Example 5

Scheme 9. Preparation of Pre-grafted Poly(Glycidyl Methacrylate)

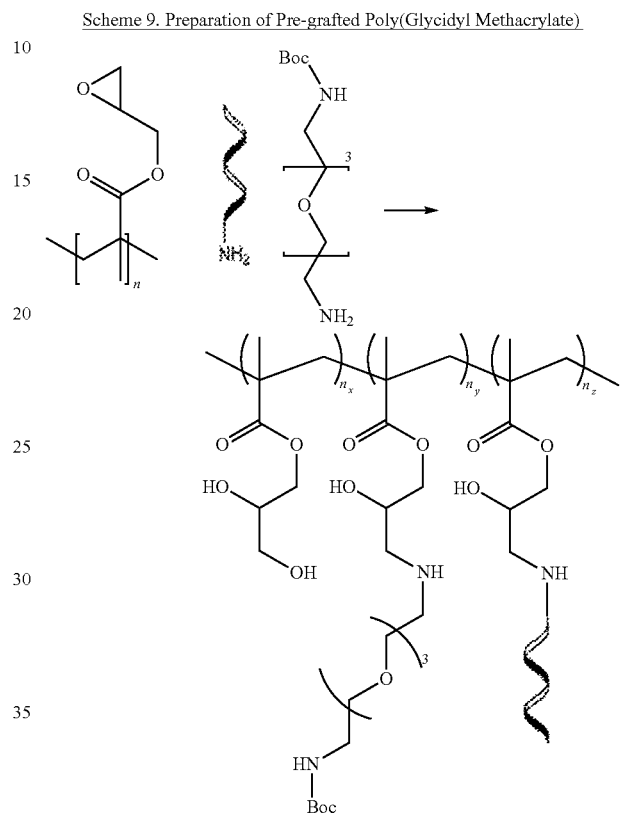

Scheme 9 illustrates the preparation of a pre-grafted poly(glycidyl methacrylate) comb polymer by reacting the glycidyl groups of the poly(glycidyl methacrylate) with the amino groups of the functionalized primers and amino-PEG-Boc-amide. This grafted polymer is then subject to Boc-deprotection to generate the primary amino functionalized side chain, which be attached to a glycidyl or epoxy functionalized surface.

Example 6

FIG. 7 illustrates the possible surface chemistry of a pre-grafted dendrimer with oligonucleotides bonded external surface. The origin point of the dendrimer can be functionalized with an azido group for direct surface attachment. Alternatively, the azido group can react with an alkyne group in the center point of a second dendrimer, wherein the second dendrimer has substrate attachment groups "A" covered external surface to create a Janus type particle for self-assembly.

Example 7

Orthogonal polymers with polyphosphazene backbone can also be used in the present application. Polyphosphazenes can serve as linear scaffolds for possible branching of the polymer architecture, building dendronized polymers, or for subsequent polymer attachment. Scheme 10.1 illustrates a synthetic route utilizing the cyclic hexachlorophosphazene core for the construction of modified acrylamide monomers.

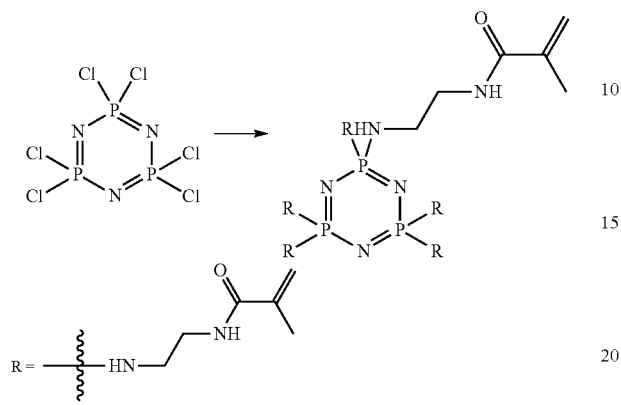

Scheme 10.2 and 10.3 demonstrate the synthesis of two polyphosphazene scaffolds for subsequent polymer attachment. Several polyphosphazene syntheses have been reported by Qiu et al., Nanotechnology, 18 (2007) 475-602 and Cheng et al., Journal of Polymer Science, Part A: Polymer Chemistry, 2013, 51, 1205-1214.

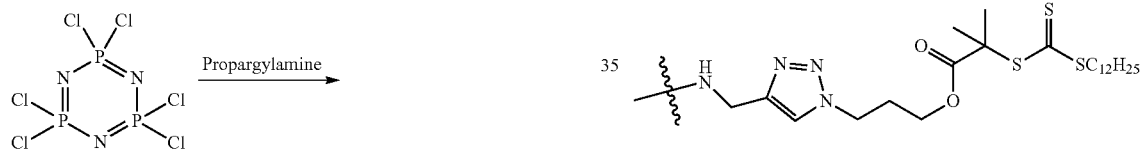

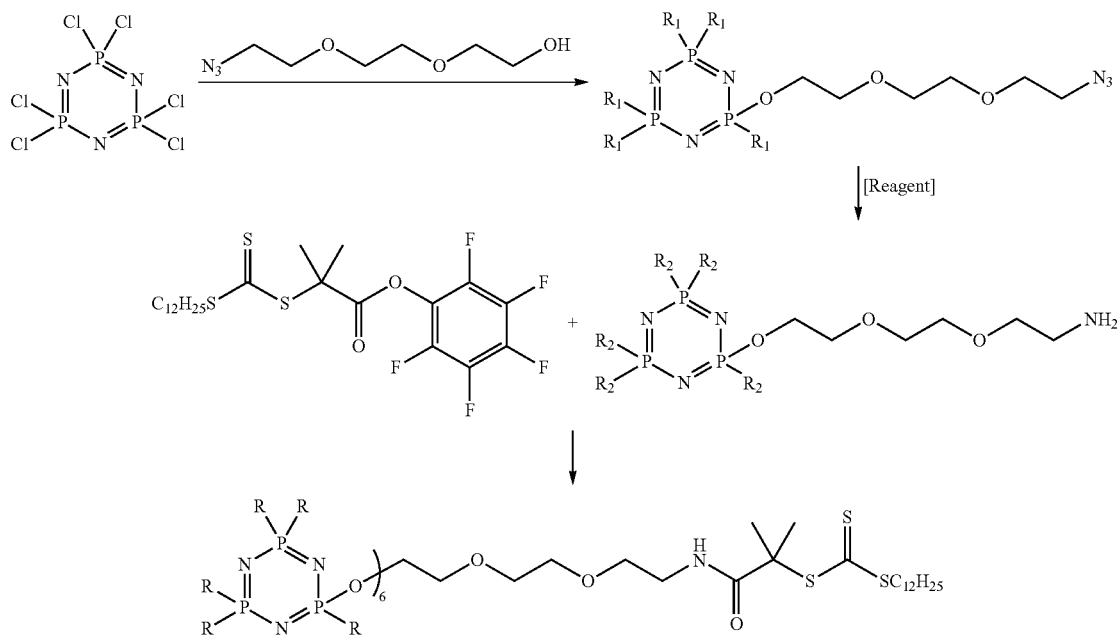

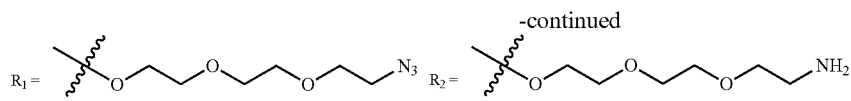

Scheme 10.4 illustrates two possible routes to prepare linear polydichlorophosphazene (PDCP) backbone. Route 1 is the anionic controlled polymerization. Route 2 is the ring opening reaction of hexachlorophosphazene. Route 1 is preferred with potential access to linear, cyclo-linear and cross-linked polymer architecture, as well as the possibility to introduce cross-linking.

Scheme 10.4.

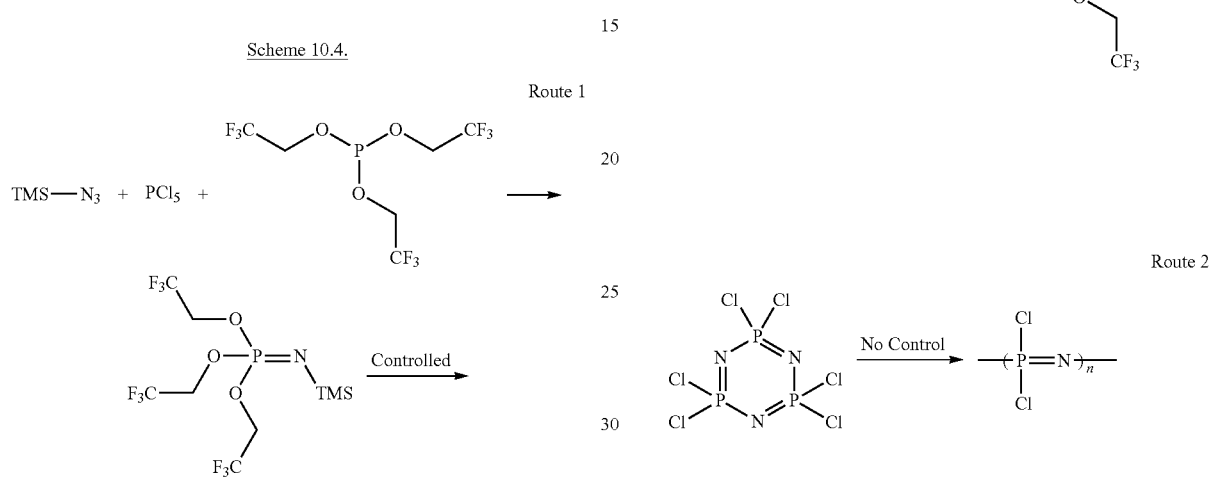

What is claimed is:

1. A substrate having a first surface comprising a polymer for surface functionalization covalently bonded thereto, wherein the polymer comprises a recurring unit of Formula (I) and a recurring unit of Formula (II):

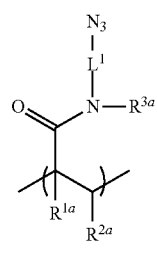

(I)

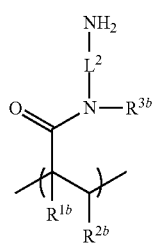

(II)

wherein:
- each of $R^{1a}$, $R^{2a}$, $R^{1b}$ and $R^{2b}$ is independently selected from the group consisting of hydrogen and optionally substituted alkyl;
- each of $R^{3a}$ and $R^{3b}$ is independently selected from the group consisting of hydrogen, optionally substituted alkyl, optionally substituted phenyl, and optionally substituted $C_{7-14}$ aralkyl; and
- each of $L^1$ and $L^2$ is independently selected from the group consisting of an optionally substituted alkylene linker and an optionally substituted heteroalkylene linker.

2. The substrate of claim 1, wherein:
each of $R^{2a}$ and $R^{3a}$ is hydrogen;
each of $R^{2b}$ and $R^{3b}$ is hydrogen;
$L^1$ is an optionally substituted alkylene; or
$L^2$ is an optionally substituted alkylene.

3. The substrate of claim 1, wherein Formula (I) is represented by Formula (Ia) and Formula (II) is represented by Formula (IIa):

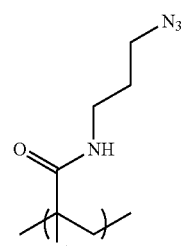

(Ia)

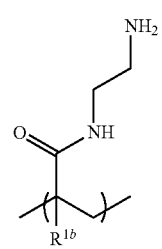

(IIa)

wherein $R^{1a}$ is hydrogen or methyl and $R^{1b}$ is hydrogen or methyl.

4. The substrate of claim 1, wherein the recurring unit of Formula (I) is represented by Formula (Ib):

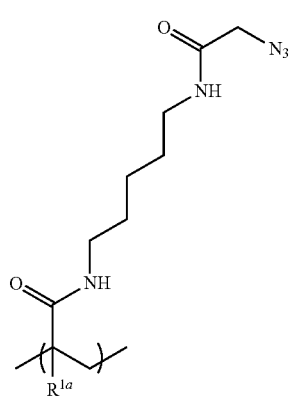

(Ib)

wherein $R^{1a}$ is hydrogen or methyl.

5. The substrate of claim 1, further comprising one or more recurring units selected from the group consisting of polyacrylamides, polyacrylates, polyurethanes, polysiloxanes, silicones, polyacroleins, polyphosphazenes, polyisocyanates, poly-ols, and polysaccharides, and combinations thereof.

6. The substrate of claim 1, further comprising one or more recurring units of Formula (IIIa) or (IIIb) or both:

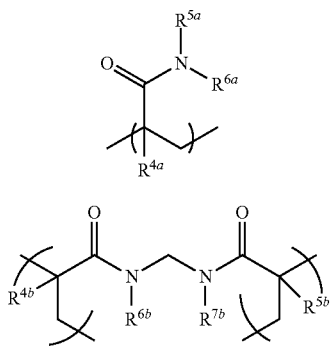

wherein
each of $R^{4a}$, $R^{4b}$, and $R^{5b}$ is independently hydrogen or $C_{1-3}$ alkyl; and
each of $R^{5a}$, $R^{6a}$, $R^{6b}$ and $R^{7b}$ is independently hydrogen, optionally substituted $C_{1-6}$ alkyl, or optionally substituted phenyl.

7. The substrate of claim 6, wherein:
each of $R^{4a}$, $R^{4b}$, and $R^{5b}$ is independently hydrogen or methyl;
$R^{6b}$ and $R^{7b}$ are each hydrogen;
at least one of $R^{5a}$ or $R^{6a}$ is hydrogen or methyl.

8. The substrate of claim 6, wherein the one or more recurring units of Formula (IIIa) are represented by Formula (IIIa1), (IIIa2), or (IIIa3):

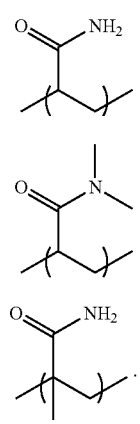

9. The substrate of claim 6, wherein the one or more recurring units of Formula (IIIb) are represented by Formula (IIIb1):

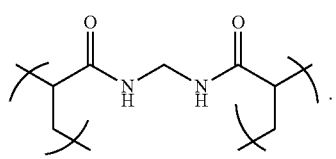

10. The substrate of claim 1, wherein the substrate surface comprises functionalized silane comprising unsaturated moieties selected from the group consisting of cycloalkenes, cycloalkynes, heterocycloalkenes, and heterocycloalkynes.

11. The substrate of claim 1, further comprising functionalized oligonucleotides covalently bonded to the polymer.

12. The substrate of claim 11, wherein the covalent bonding between the functionalized oligonucleotide and the polymer comprises the structural moiety:

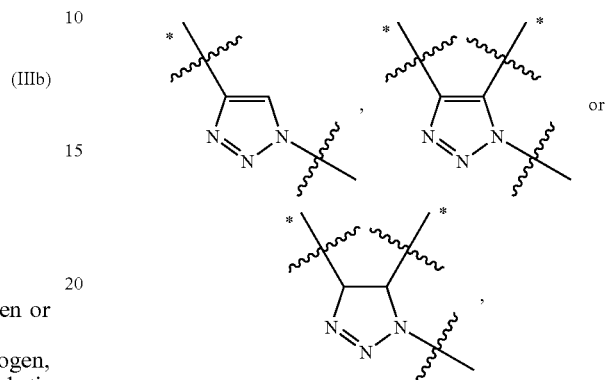

or combinations thereof,
wherein * indicates the point of connection with the functionalized oligonucleotide.

13. The substrate of claim 11, wherein the polymer comprises modified recurring units of the structure:

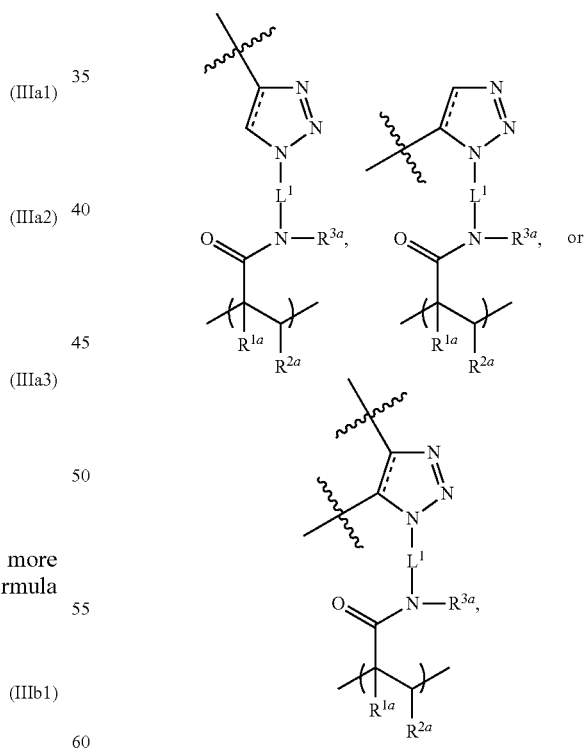

wherein the covalent bonding position with the functionalized nucleotide is shown by a bond with a wavy line, and wherein ----- is a single or double bond.

14. The substrate of claim 11, wherein the functionalized oligonucleotides are covalently bonded to the polymer through reaction of one or more functional moieties on the functional oligonucleotides, which are selected from the group consisting of alkynes, cycloalkenes, cycloalkynes, heterocycloalkenes, and heterocycloalkynes, and optionally substituted variants thereof, and combinations thereof.

15. The substrate of claim 14, wherein the functional moieties comprise alkynes or substituted variants thereof.

16. The substrate of claim 11, wherein the covalent bond between the functionalized oligonucleotide and the polymer is the product of an azide click chemistry reaction.

17. The substrate of claim 16, wherein the functionalized oligonucleotides are covalently bonded to the polymer through reaction of one or more functionalized moieties of the functionalized oligonucleotides with azido groups of the polymer, wherein the one or more functional moieties are selected from the group consisting of alkynes, cycloalkenes, cycloalkynes, heterocycloalkenes, and heterocycloalkynes, and optionally substituted variants thereof, and combinations thereof.

18. The substrate of claim 1, comprising both polymer-coated regions and inert regions.

19. The substrate of claim 18, wherein the polymer-coated regions are wells and the inert regions are interstitial regions.

20. A method of immobilizing a polymer to a first surface of a substrate comprising:
contacting a polymer comprising a recurring unit of Formula (I) and a recurring unit of Formula (II) with the first surface of the substrate, said first surface comprising a first plurality of functional groups covalently attached thereto; and
reacting the first plurality of functional groups of the first surface with the polymer, thereby covalently bonding the polymer to the first surface of the substrate;

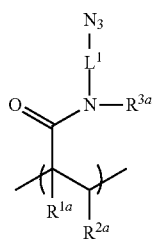

(I)

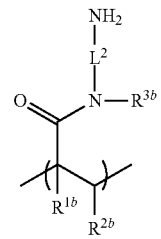

(II)

wherein:
each of $R^{1a}$, $R^{2a}$, $R^{1b}$ and $R^{2b}$ is independently selected from the group consisting of hydrogen and optionally substituted alkyl;

each of $R^{3a}$ and $R^{3b}$ is independently selected from the group consisting of hydrogen, optionally substituted alkyl, optionally substituted phenyl, and optionally substituted $C_{7-14}$ aralkyl; and each of $L^1$ and $L^2$ is independently selected from the group consisting of an optionally substituted alkylene linker and an optionally substituted heteroalkylene linker.

21. The method of claim 20, wherein the first plurality of functional groups comprise vinyl, acryloyl, alkenyl, cycloalkenyl, heterocycloalkenyl, alkynyl, cycloalkynyl, heterocycloalkynyl, nitrene, aldehyde, hydrazinyl, glycidyl ether, epoxy, carbene, isocyanate, and maleimide, or optionally substituted variants or combinations thereof.

22. The method of claim 20, wherein the first plurality of functional groups comprise epoxy or norbornene groups, or a combination thereof.

* * * * *

UNITED STATES PATENT AND TRADEMARK OFFICE
CERTIFICATE OF CORRECTION

PATENT NO. : 10,208,142 B2
APPLICATION NO. : 15/809656
DATED : February 19, 2019
INVENTOR(S) : Andrew A. Brown et al.

Page 1 of 3

It is certified that error appears in the above-identified patent and that said Letters Patent is hereby corrected as shown below:

On the Title Page

Item (73), Line 1, under Assignee, change "Illumnia Cambridge Limited," to --Illumina Cambridge Limited,--.

In the Specification

In Column 2, Lines 9-28 (Approx.), change " 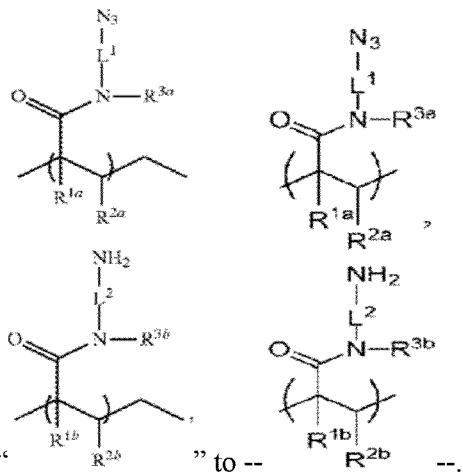 " to -- --.

In Column 10, Line 65, change "aUV-Vis" to --a UV-Vis--.

In Column 12, Line 66, change "azidobenoate" to --azidobenzoate--.

In Column 16, Line 45, change "isoquinlinyl," to --isoquinolinyl,--.

In Column 16, Line 56, change "isoxazollylalkyl," to --isoxazolylalkyl,--.

In Column 17, Line 10, change "bicycle" to --bicyclo--.

Signed and Sealed this
Thirtieth Day of July, 2019

Andrei Iancu
*Director of the United States Patent and Trademark Office*

CERTIFICATE OF CORRECTION (continued)

In Column 18, Line 4, change "1,4-oxathiinyl" to --1,4-oxathianyl--.

In Column 18, Lines 9-10 (Approx.), change "tetrahydrothi ophenyl," to --tetrahydrothiophenyl,--.

In Column 20, Line 39 (Approx.), change "sub stituent" to --substituent--.

In Column 24, Lines 15-16 (Approx.), change "—(CH₂)m-NH—(CH₂)n-optionally substituted" to -- –(CH₂)ₘ–NH– (CH₂)ₙ– optionally substituted--.

In Column 24, Lines 55-64 (Approx.), change " 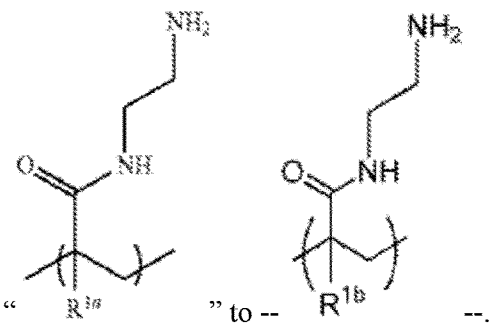 " to -- --.

In Column 30, Line 36, change "eR$^{2d}$" to --R$^{2d}$--.

In Column 30, Line 42 (Approx.), change "embodiments" to --embodiments,--.

In Column 38, Lines 3-9 (Approx.), after " 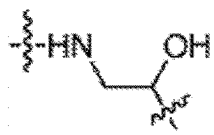 " insert --.--.

In Column 43, Line 32, change "aresnide," to --arsenide,--.

In Column 44, Lines 12-13, change "SPECTRASIL™." to --SPECTROSIL™.--.

In Column 45, Line 63 (Approx.), change "concatameric" to --concatemeric--.

In Column 59, Lines 55-64 (Approx.), change " 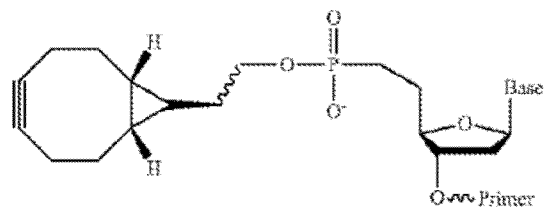 " to

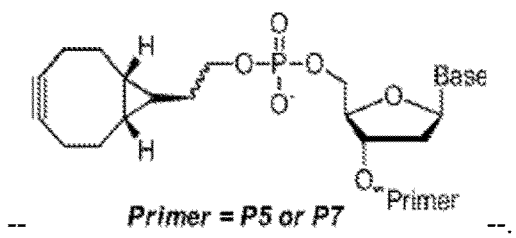
In Column 61, Lines 27-54 (Approx.),
change " 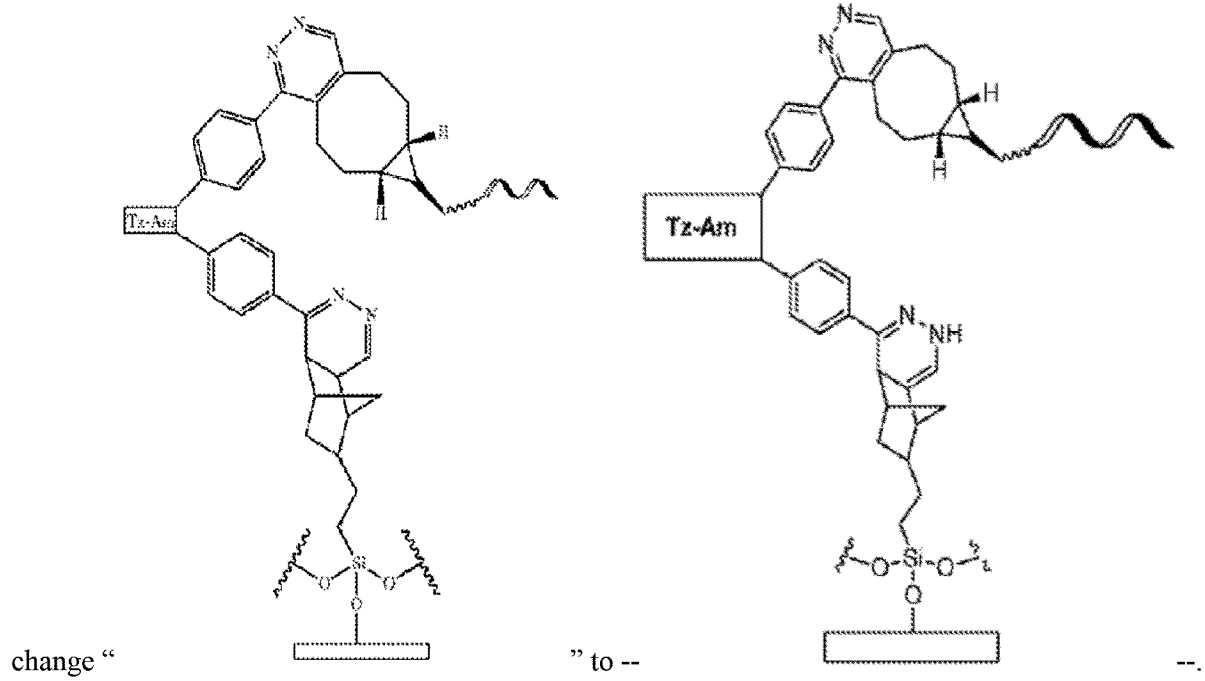 " to -- --.
In Columns 67-68, Line 38 (Approx.), change "Artifically" to --Artificially--.
In Columns 67-68, Line 45 (Approx.), change "Artifically" to --Artificially--.
In Columns 67-68, Line 53 (Approx.), change "Artifically" to --Artificially--.
In Columns 69-70, Line 7 (Approx.), change "Artifically" to --Artificially--.